(12) United States Patent (10) Patent No.: US 8,318,776 B2
Mizuno (45) Date of Patent: Nov. 27, 2012

(54) PYRIDINE COMPOUND, PESTICIDAL COMPOSITION AND METHOD OF CONTROLLING PESTS

(75) Inventor: Hajime Mizuno, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 72 days.

(21) Appl. No.: 12/743,771

(22) PCT Filed: Nov. 18, 2008

(86) PCT No.: PCT/JP2008/071283
§ 371 (c)(1),
(2), (4) Date: May 19, 2010

(87) PCT Pub. No.: WO2009/066786
PCT Pub. Date: May 28, 2009

(65) Prior Publication Data
US 2010/0286148 A1 Nov. 11, 2010

(30) Foreign Application Priority Data

Nov. 20, 2007 (JP) ................................. 2007-300138

(51) Int. Cl.
*C07D 413/04* (2006.01)
(52) U.S. Cl. ........ 514/340; 514/336; 514/277; 514/183; 546/269.4; 546/269.1; 546/268.4; 546/268.1
(58) Field of Classification Search .................. None
See application file for complete search history.

(56) References Cited

U.S. PATENT DOCUMENTS

| 5,985,904 A | 11/1999 | Jeschke et al. |
| 6,090,831 A | 7/2000 | Assmann et al. |
| 6,239,160 B1 | 5/2001 | Tiebes et al. |

FOREIGN PATENT DOCUMENTS

| CA | 2005658 | 6/1990 |
| CA | 2 294 888 A1 | 12/1998 |
| CL | 80-95 | 1/1995 |
| CL | 2221-2005 | 1/2005 |
| CL | 2628-2006 | 1/2006 |
| EP | 0353191 A2 | 1/1990 |
| EP | 0374753 A2 | 6/1990 |
| EP | 0392225 A2 | 10/1990 |
| EP | 0427529 A1 | 5/1991 |
| EP | 0451878 A1 | 10/1991 |
| JP | 2001-520666 A | 10/2001 |
| JP | 2002-205991 A | 7/2002 |
| WO | WO 93/07278 A1 | 4/1993 |
| WO | WO 95/33818 A2 | 12/1995 |
| WO | WO 95/34656 A1 | 12/1995 |
| WO | WO 98/47369 A1 | 10/1998 |
| WO | WO 98/57969 A1 | 12/1998 |
| WO | WO 02/068417 A2 | 9/2002 |
| WO | WO 03/000906 A2 | 1/2003 |
| WO | WO 03/052073 A2 | 6/2003 |
| WO | WO 2007/039176 A1 | 4/2007 |

OTHER PUBLICATIONS

Machine Translation of Japanese Patent Publication No. 2002-205991-A (published Jul. 23, 2002).*
Chilean Office Action issued on Mar. 14, 2011 in Chilean Patent Application No. 3454-08 with English translation.
Biao Jiang et al. "alpha-(Trifluoromethyl)ethenyl boronic acid as a Useful Trifluoromethyl Containing Buiding Block. Preparation and Palladium-catalysed Coupling with Aryl Halides." Tetrahedron Letters, 2001, 42, 4083-4085.
Charles C. Price et al. "Free-Radical Chlorination of Methyl Cyclohexanecarboxylates." Journal of the American Chemical Society, 1970, 5916-5921.
Christophe Délye. "Weed Resistance to Acetyl Coenzyme a Carboxylase Inhibitors: an Update." Weed Science, 2005, 53, 728-746.
Christopher Bieniarz et al. "An Efficient and Environmentally Friendly Synthesis of the Inhalation Anesthetic Sevoflurane." Journal of Fluorine Chemistry, 2000, 106, 99-102. Clifford D. Bedford et al. "Quaternary Salts of 2-[(Hydroxyimino)methyl]imidazole. 2. Preparation and in Vitro and in Vivo Evaluation of 1-(Alkoxymethyl)-2-[(hydroxyimino)methyl]-3-methylimidazolium Halides for Reactivation of Organophosphorus-Inhibited Acetylcholinesterases." Journal of Medicinal Chemistry, 1989, 32, 493-503.
E. T. McBee et al. "Alcohols and Olefins Containing the Pentafluoroethyol Group." Journal of the American Chemical Society, 1952, 74, 1387-1390.
Takashi Mori et al. "4-Difluoromethylated Quinoline Synthesis via Intramolecular SN2' Reaction of alpha-Trifluoromethylstyrenes Bearing Imine Moieties." Chemistry Letters, 2004, 33, 1206-1207.
Trisha Gura. "Repairing the Genome's Spelling Mistakes." Science, 1999, 285, 316-318.
Viacheslav A. Petrov. "A Simple Procedure for Nucleophilic Perfluoroalkylation of Organic and Inorganic Substrates." Tetrahedron Letters, 2001, 42, 3267-3269.
William B. Parker et al. "Dominant Mutations Causing Alterations in Acetyl-coenzyme A Carboxylase Confer Tolerance to Cyclohexanedione and Aryloxyphenoxypropionate Herbicides in Maize." Proc. Natl. Acad. Sci. USA, 1990, 87, 7175-7179.

\* cited by examiner

*Primary Examiner* — Anish Gupta
*Assistant Examiner* — Theodore R West
(74) *Attorney, Agent, or Firm* — Birch, Stewart, Kolasch & Birch, LLP

(57) ABSTRACT

A pyridine compound represented by the following general formula (1); the pyridine compound in which $R^1$ is a C1-C3 fluoroalkyl group or a C1-C3 fluoroalkoxy group; the pyridine compound in which $R^2$ is a hydrogen atom; the pyridine compound in which $R^2$ is a group represented by $Q^1$; a pesticidal composition containing the pyridine compound as an active ingredient; and a method of controlling a pest including applying an effective amount of the pyridine compound to the pest or a place where the pest inhabits, are provided.

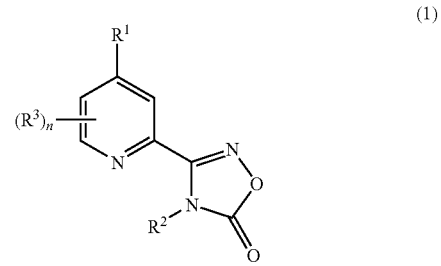

(1)

13 Claims, No Drawings

PYRIDINE COMPOUND, PESTICIDAL COMPOSITION AND METHOD OF CONTROLLING PESTS

TECHNICAL FIELD

The present invention relates to a pyridine compound, a pesticidal composition and a method of controlling a pest.

BACKGROUND ART

Previously, for controlling pests, many compounds have been developed and used. For example, a certain pyridine compound is known to be effective in controlling a pest (see Japanese National Patent Publication No. 2001-520666 and Japanese Patent Laying-Open No. 2002-205991).

DISCLOSURE OF THE INVENTION

However, since these pyridine compounds may not necessarily have sufficient effect in controlling a pest, development of a compound having excellent effect in controlling a pest has been desired.

The present inventors intensively studied in order to find out a compound having excellent effect in controlling a pest and, as a result, found out that a compound of the following general formula (1) has excellent effect in controlling a pest, completing the present invention.

The present application includes;

[Invention 1]

A pyridine compound represented by the general formula (1):

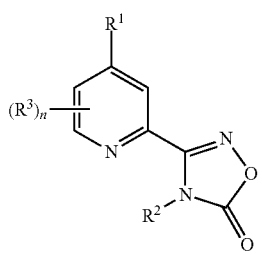

(1)

wherein $R^1$ represents a C1-C7 haloalkyl group, or a C1-C7 haloalkoxy group, the C1-C7 haloalkyl group and the C1-C7 haloalkoxy group being optionally substituted with a group selected from the group consisting of C1-C3 alkoxy groups, C1-C3 haloalkoxy groups, C3-C7 alkenyloxy groups, C3-C7 haloalkenyloxy groups, C3-C7 alkynyloxy groups, C3-C7 haloalkynyloxy groups, tri(C1-C4 alkyl)silyloxy groups and a hydroxyl group;

$R^2$ represents a cyanomethyl group; a hydrogen atom; a C1-C7 chain hydrocarbon group optionally substituted with a halogen atom; a (C3-C7 cycloalkyl)methyl group optionally substituted with a group selected from the group consisting of halogen atoms, C1-C3 alkyl groups and C1-C3 haloalkyl groups; a benzyl group optionally substituted with a group selected from the group consisting of halogen atoms, a cyano group, a nitro group, C1-C3 alkyl groups, C1-C3 haloalkyl groups and C1-C3 alkoxy groups; or a group represented by any one of the formulae $Q^1$ to $Q^5$:

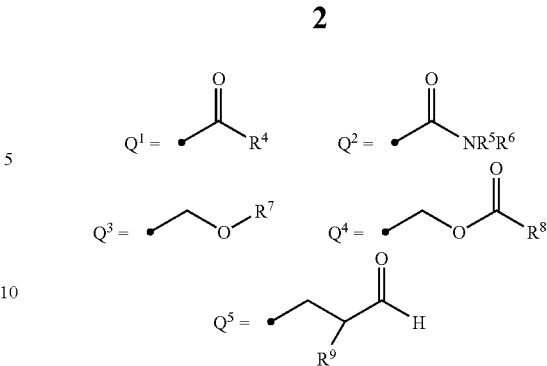

wherein $R^4$ represents a hydrogen atom; a C1-C7 chain hydrocarbon group optionally substituted with a halogen atom; or a C3-C7 cycloalkyl group optionally substituted with a group selected from the group consisting of halogen atoms, C1-C3 alkyl groups and C1-C3 haloalkyl groups;

$R^5$ and $R^6$ may be the same or different, and each represents a C1-C7 chain hydrocarbon group optionally substituted with a halogen atom; a C1-C7 alkoxy group; or a C3-C7 cycloalkyl group optionally substituted with a group selected from the group consisting of halogen atoms, C1-C3 alkyl groups and C1-C3 haloalkyl groups, or $R^5$ and $R^6$ may be taken together with a nitrogen atom constituting —$NR^5R^6$ to represent a pyrrolidin-1-yl group, a piperidino group, a hexamethyleneimin-1-yl group, a morpholino group or a thiomorpholin-4-yl group, where the pyrrolidin-1-yl group, the piperidino group, the hexamethyleneimin-1-yl group, the morpholino group and the thiomorpholin-4-yl group may be each substituted with a group selected from the group consisting of halogen atoms, C1-C3 alkyl groups and C1-C3 haloalkyl groups;

$R^7$ represents a C1-C7 chain hydrocarbon group optionally substituted with a halogen atom; a phenyl group optionally substituted with a group selected from the group consisting of halogen atoms, a cyano group, a nitro group, C1-C3 alkyl groups, C1-C3 haloalkyl groups and C1-C3 alkoxy groups; a benzyl group optionally substituted with a group selected from the group consisting of halogen atoms, a cyano group, a nitro group, C1-C3 alkyl groups, C1-C3 haloalkyl groups and C1-C3 alkoxy groups; or a C3-C7 cycloalkyl group optionally substituted with a group selected from the group consisting of halogen atoms, C1-C3 alkyl groups and C1-C3 haloalkyl groups;

$R^8$ represents a C1-C7 chain hydrocarbon group optionally substituted with a halogen atom; a phenyl group optionally substituted with a group selected from the group consisting of halogen atoms, a cyano group, a nitro group, C1-C3 alkyl groups, C1-C3 haloalkyl groups, C1-C3 alkoxy groups and C1-C3 haloalkoxy groups; or a C3-C7 cycloalkyl group optionally substituted with a group selected from the group consisting of halogen atoms, C1-C3 alkyl groups and C1-C3 haloalkyl groups;

$R^9$ represents a hydrogen atom, or a C1-C7 chain hydrocarbon group optionally substituted with a halogen atom; and $R^3$ represents a C1-C7 chain hydrocarbon group optionally substituted with a halogen atom; a C1-C7 alkoxy group; a C1-C3 haloalkoxy group; a halogen atom; a C3-C7 cycloalkyl group optionally substituted with a group selected from the group consisting of halogen atoms, C1-C3 alkyl groups and C1-C3 haloalkyl groups; or a C3-C7 cycloalkoxy group optionally substituted with a group selected from the group consisting of halogen atoms, C1-C3 alkyl groups and C1-C3 haloalkyl groups; and n represents an integer of 0 to 3 (hereinafter referred to as present compound).

[Invention 2]

The pyridine compound according to the invention 1, wherein $R^1$ is a C1-C3 haloalkyl group optionally substituted with a group selected from the group consisting of C1-C3 alkoxy groups, C3-C7 alkenyloxy groups, tri(C1-C4 alkyl)silyloxy groups and a hydroxyl group, or a C1-C3 haloalkoxy group optionally substituted with a group selected from the group consisting of C1-C3 alkoxy groups, C3-C7 alkenyloxy groups, tri(C1-C4 alkyl)silyloxy groups and a hydroxyl group.

[Invention 3]

The pyridine compound according to the invention 1, wherein $R^1$ is a C1-C3 haloalkyl group optionally substituted with a C1-C3 alkoxy group, or a C1-C3 haloalkoxy group.

[Invention 4]

The pyridine compound according to the invention 1, wherein $R^1$ is a C1-C3 fluoroalkyl group optionally substituted with a C1-C3 alkoxy group, or a C1-C3 fluoroalkoxy group.

[Invention 5]

The pyridine compound according to the invention 1, wherein $R^1$ is a C1-C3 fluoroalkyl group or a C1-C3 fluoroalkoxy group, $R^7$ is a C1-C7 chain hydrocarbon group optionally substituted with a halogen atom; a benzyl group optionally substituted with a group selected from the group consisting of halogen atoms, a cyano group, a nitro group, C1-C3 alkyl groups, C1-C3 haloalkyl groups and C1-C3 alkoxy groups; or a C3-C7 cycloalkyl group optionally substituted with a group selected from the group consisting of halogen atoms, C1-C3 alkyl groups and C1-C3 haloalkyl groups.

[Invention 6]

The pyridine compound according to the invention 1, 2, 3, 4 or 5, wherein $R^2$ is a cyclopropylmethyl group optionally substituted with a C1-C3 alkyl group; a cyanomethyl group; a C1-C7 alkyl group; a hydrogen atom; a benzyl group optionally substituted with a group selected from the group consisting of halogen atoms, a cyano group, a nitro group, C1-C3 alkyl groups, C1-C3 haloalkyl groups and C1-C3 alkoxy groups; or a group represented by any one of the formulae $Q^{1a}$ to $Q^{5a}$:

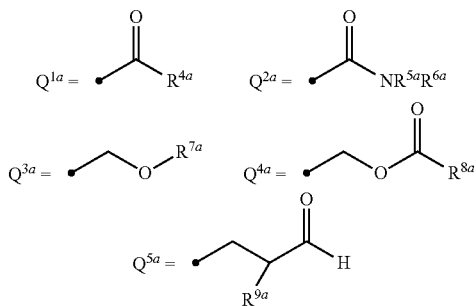

wherein $R^{4a}$ represents a C1-C7 alkyl group, a C1-C7 haloalkyl group, or a C3-C7 cycloalkyl group optionally substituted with a group selected from the group consisting of halogen atoms, C1-C3 alkyl groups and C1-C3 haloalkyl groups;

$R^{5a}$ and $R^{6a}$ may be the same or different, and each represents a C1-C7 alkyl group, a C1-C7 haloalkyl group, a C3-C7 alkenyl group or a C1-C7 alkoxy group, or $R^{5a}$ and $R^{6a}$ may be taken together with a nitrogen atom constituting —$NR^{5a}R^{6a}$ to represent a pyrrolidin-1-yl group, a piperidino group, a hexamethyleneimin-1-yl group, a morpholino group or a thiomorpholin-4-yl group, where the pyrrolidin-1-yl group, the piperidino group, the hexamethyleneimin-1-yl group, the morpholino group and the thiomorpholin-4-yl group may be each substituted with a group selected from the group consisting of halogen atoms, C1-C3 alkyl groups and C1-C3 haloalkyl groups;

$R^{7a}$ represents a phenyl group optionally substituted with a group selected from the group consisting of halogen atoms, a cyano group, a nitro group, C1-C3 alkyl groups, C1-C3 haloalkyl groups and C1-C3 alkoxy groups; a benzyl group optionally substituted with a group selected from the group consisting of halogen atoms, a cyano group, a nitro group, C1-C3 alkyl groups, C1-C3 haloalkyl groups and C1-C3 alkoxy groups; or a C3-C7 cycloalkyl group optionally substituted with a group selected from the group consisting of halogen atoms, C1-C3 alkyl groups and C1-C3 haloalkyl groups;

$R^{8a}$ represents a phenyl group optionally substituted with a group selected from the group consisting of halogen atoms, a cyano group, a nitro group, C1-C3 alkyl groups, C1-C3 haloalkyl groups, C1-C3 alkoxy groups and C1-C3 haloalkoxy groups; or a C3-C7 cycloalkyl group optionally substituted with a group selected from the group consisting of halogen atoms, C1-C3 alkyl groups and C1-C3 haloalkyl groups; and $R^{9a}$ represents a hydrogen atom or a C1-C3 alkyl group; and $R^3$ is a C3-C7 cycloalkyl group optionally substituted with a group selected from the group consisting of halogen atoms, C1-C3 alkyl groups and C1-C3 haloalkyl groups; a C3-C7 cycloalkoxy group optionally substituted with a group selected from the group consisting of halogen atoms, C1-C3 alkyl groups and C1-C3 haloalkyl groups; a halogen atom; a C1-C7 alkyl group; a C1-C7 haloalkyl group; a C1-C7 alkoxy group; or a C1-C3 haloalkoxy group.

[Invention 7]

The pyridine compound according to the invention 1, 2, 3, 4 or 5, wherein $R^2$ is a hydrogen atom.

[Invention 8]

The pyridine compound according to the invention 1, 2, 3, 4 or 5, wherein $R^2$ is a group represented by $Q^1$.

[Invention 9]

The pyridine compound according to the invention 1, 2, 3, 4 or 5, wherein $R^2$ is a group represented by $Q^2$.

[Invention 10]

The pyridine compound according to the invention 1, 2, 3, 4 or 5, wherein $R^2$ is a group represented by $Q^3$.

[Invention 11]

The pyridine compound according to the invention 1, 2, 3, 4 or 5, wherein $R^2$ is a group represented by $Q^4$.

[Invention 12]

A pesticidal composition containing the pyridine compound according to the invention 1, 2, 3, 4, 5, 6, 7, 8, 9, 10 or 11 as an active ingredient.

[Invention 13]

A method of controlling a pest including applying an effective amount of the pyridine compound according to the invention 1, 2, 3, 4, 5, 6, 7, 8, 9, 10 or 11 to the pest or a place where the pest inhabits.

BEST MODES FOR CARRYING OUT THE INVENTION

In the present invention, a halogen atom means a fluorine atom, a chlorine atom, a bromine atom or an iodine atom.

Examples of the "C1-C7 haloalkyl group" include a fluoromethyl group, a chloromethyl group, a bromomethyl group, a difluoromethyl group, a dichloromethyl group, a dibromomethyl group, a trifluoromethyl group, a trichloromethyl group, a dichlorofluoromethyl group, a chlorodifluoromethyl group, a bromodifluoromethyl group, a 2,2,2-trifluoroethyl group, a 1,1,2,2,2-pentafluoroethyl group, a 3,3,3-trifluoropropyl group, a 2,2,3,3,3-pentafluoropropyl group, a heptafluoropropyl group, a 2,2,2-trifluoro-1-methylethyl group, a 2,2,2-trifluoro-1-ethylethyl group, a 2,2,3,3,3-pentafluoro-1-methylpropyl group, a 2,2,3,3,3-pentafluoro-1-ethylpropyl group, a 2,2,2-trifluoro-1-(trifluoromethyl)ethyl group, and a heptafluoroisopropyl group.

The C1-C7 haloalkyl group may be substituted with a group selected from the group consisting of C1-C3 alkoxy groups, C1-C3 haloalkoxy groups, C3-C7 alkenyloxy groups, C3-C7 haloalkenyloxy groups, C3-C7 alkynyloxy groups, C3-C7 haloalkynyloxy groups, tri(C1-C4 alkyl)silyloxy groups and a hydroxyl group. Examples of the C1-C7 haloalkyl group substituted with the substituent include a 2,2,2-trifluoro-1-hydroxyethyl group, a 2,2,2,3,3-pentafluoro-1-hydroxypropyl group, a 2,2,2-trifluoro-1-hydroxy-1-methylethyl group, a 2,2,2-trifluoro-1,1-dihydroxyethyl group, a 2,2,2-trifluoro-1-methoxyethyl group, a 2,2,2-trifluoro-1-ethoxyethyl group, a 2,2,2-trifluoro-1-propoxyethyl group, a 2,2,2,3,3-pentafluoro-1-methoxypropyl group, a 2,2,2,3,3-pentafluoro-1-ethoxypropyl group, a 2,2,2-trifluoro-1-(2-propynyloxy)ethyl group, a 2,2,2-trifluoro-1-(2-propenyloxy)ethyl group, and a 2,2,2-trifluoro-1-methyl-1-(trimethylsilyloxy)ethyl group.

Examples of the "C1-C7 haloalkoxy group" include a fluoromethoxy group, a chloromethoxy group, a bromomethoxy group, a dichloromethoxy group, a dibromomethoxy group, a trifluoromethoxy group, a trichloromethoxy group, a dichlorofluoromethoxy group, a chlorodifluoromethoxy group, a trifluoromethoxy group, a difluoromethoxy group, a difluorobromomethoxy group, a 2,2,2-trifluoroethoxy group, a pentafluoroethoxy group, a 3,3,3,2,2-pentafluoropropoxy group, a 2,2,2-trifluoro-1-methylethoxy group and a 2,2,2-trifluoro-1-(trifluoromethyl)ethoxy group.

The "C1-C7 haloalkoxy group" may be substituted with a group selected from the group consisting of C1-C3 alkoxy groups, C1-C3 haloalkoxy groups, C3-C7 alkenyloxy groups, C3-C7 haloalkenyloxy groups, C3-C7 alkynyloxy groups, C3-C7 haloalkynyloxy groups, tri(C1-C4 alkyl)silyloxy groups and a hydroxyl group. Examples of the C1-C3 haloalkoxy group substituted with the substituent include a 2,2,2-trifluoro-1-methoxyethoxy group, a 2,2,2-trifluoro-1-(2-propenyloxy)ethoxy group, and a 2,2,2-trifluoro-1-methyl-1-(trimethylsilyloxy)ethoxy group.

In the present invention, examples of the "C1-C7 chain hydrocarbon group optionally substituted with a halogen atom" include a C1-C7 alkyl group, a C1-C7 haloalkyl group, a C3-C7 alkenyl group, a C3-C7 haloalkenyl group, a C3-C7 alkynyl group and a C3-C7 haloalkynyl group.

Examples of the "C1-C7 alkyl group" include a methyl group, an ethyl group, a propyl group, a 2-methylpropyl group, a 1-methylpropyl group, a 1,1-dimethylethyl group, a 3-methylbutyl group, a 2,2-dimethylpropyl group, a 1,1-dimethylpropyl group, a hexyl group, a 4-methylpentyl group, a 3-methylpentyl group, a 1,3-dimethylbutyl group, a heptyl group and a 1-ethyl-1-methylbutyl group.

Examples of the "C1-C7 haloalkyl group" include a trifluoromethyl group, a trichloromethyl group, a difluoromethyl group, a 2,2,2-trifluoroethyl group, a 1,1,2,2,2-pentafluoroethyl group, a 3,3,3-trifluoropropyl group, a 2,2,3,3,3-pentafluoropropyl group, a heptafluoropropyl group, a 1-methyl-2,2,2-trifluoroethyl group, a 1-trifluoromethyl-2,2,2-trifluoroethyl group and a heptafluoroisopropyl group.

Examples of the "C3-C7 alkenyl group" include a 2-propenyl group, a 3-butenyl group, a 1-methyl-2-propenyl group, a 2-methyl-2-propenyl group, a 2-pentenyl group, a 1-methyl-2-butenyl group, a 3-methyl-3-butenyl group, a 1-ethyl-2-propenyl group, a 2-hexenyl group, a 2-methyl-2-pentenyl group, a 3-methyl-2-pentenyl group, a 4-methyl-2-pentenyl group, a 1-methyl-3-pentenyl group, a 4-methyl-3-pentenyl group, a 1-methyl-4-pentenyl group and a 4-methyl-4-pentenyl group.

Examples of the "C3-C7 haloalkenyl group" include a 3-chloro-2-propenyl group, a 3,3-dichloro-2-propenyl group, a 4,4-dichloro-3-butenyl group and a 2-chloro-2-propenyl group.

Examples of the "C3-C7 alkynyl group" include a 2-propynyl group, a 2-butynyl group, and a 3-butynyl group.

Examples of the "C3-C7 haloalkynyl group" include a 4-chlorobutynyl group.

In the present invention, examples of the "(C3-C7 cycloalkyl)methyl group optionally substituted with a group selected from the group consisting of halogen atoms, C1-C3 alkyl groups and C1-C3 haloalkyl groups" include a (cyclopropyl)methyl group, a (1-methylcyclopropyl)methyl group, a (2,2-dimethylcyclopropyl)methyl group, a (cyclopentyl)methyl group and a cyclohexylmethyl group.

Examples of the "benzyl group optionally substituted with a group selected from the group consisting of halogen atoms, a cyano group, a nitro group, C1-C3 alkyl groups, C1-C3 haloalkyl groups and C1-C3 alkoxy groups" include a benzyl group, a 1-phenylethyl group, a 2-chlorobenzyl group, a 3-chlorobenzyl group, a 4-chlorobenzyl group, a 3-bromobenzyl group, a 4-bromobenzyl group, a 2-fluorobenzyl group, a 3-fluorobenzyl group, a 2-cyanobenzyl group, a 3-cyanobenzyl group, a 4-cyanobenzyl group, a 2-nitrobenzyl group, a 3-nitrobenzyl group, a 4-nitrobenzyl group, a 2-methylbenzyl group, a 3-methylbenzyl group, a 4-methylbenzyl group, a 2-(trifluoromethyl)benzyl group, a 3-(trifluoromethyl)benzyl group, a 4-(trifluoromethyl)benzyl group, a 2-methoxybenzyl group, a 3-methoxybenzyl group and a 4-methoxybenzyl group.

Examples of the "C3-C7 cycloalkyl group optionally substituted with a group selected from the group consisting of halogen atoms, C1-C3 alkyl groups and C1-C3 haloalkyl groups" include a cyclopropyl group, a 1-methylcyclopropyl group, a 2-methylcyclopropyl group, a 2,2-dimethylcyclopropyl group, a 2-fluorocyclopropyl group, a cyclobutyl group, a 1-trifluoromethylcyclobutyl group, a cyclopentyl group, a 2-methylcyclopentyl group, a cyclohexyl group, a 1-methylcyclohexyl group, a 2-methylcyclohexyl group, a 3-methylcyclohexyl group, a 4-methylcyclohexyl group, a 4-trifluoromethylcyclohexyl group, a 2-fluorocyclohexyl group, a 3-fluorocyclohexyl group, a 4-fluorocyclohexyl group, and a cycloheptyl group.

Examples of the "C1-C7 alkoxy group" include a methoxy group, an ethoxy group, a propoxy group, an isopropoxy group, a hexyloxy group, a 5-methylpentyloxy group, a 3-methylpentyloxy group, a 1,3-dimethylbutyloxy group, a heptyloxy group, and a 1-ethyl-1-methylbutyloxy group.

In the present invention, the pyrrolidin-1-yl group, the piperidino group, the hexamethyleneimin-1-yl group, the morpholino group and the thiomorpholin-4-yl group may be each substituted with a group selected from the group consisting of halogen atoms, C1-C3 alkyl groups and C1-C3 haloalkyl groups.

Examples of such a substituted pyrrolidin-1-yl group include a 2-methylpyrrolidin-1-yl group and a 3,5-dimethylpyrrolidin-1-yl group.

Examples of such a substituted piperidino group include a 2-methylpiperidino group, a 3-methylpiperidino group, a 3,5-dimethylpiperidino group and a 4-tert-butylpiperidino group.

Examples of such a substituted morpholino group include a 3,5-dimethylmorpholino group.

Examples of the "phenyl group optionally substituted with a group selected from the group consisting of halogen atoms, a cyano group, a nitro group, C1-C3 alkyl groups, C1-C3 haloalkyl groups, C1-C3 alkoxy groups and C1-C3 haloalkoxy groups" include a phenyl group, a 2-chlorophenyl group, a 3-chlorophenyl group, a 4-chlorophenyl group, a 3-fluorophenyl group, a 4-fluorophenyl group, a 3-bromophenyl group, a 3-iodophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-(trifluoromethyl)phenyl group, a 3-(trifluoromethyl)phenyl group, a 4-(trifluoromethyl)phenyl group, a 2-methoxyphenyl group, a 3-methoxyphenyl group, a 4-methoxyphenyl group, a 3-(trifluoromethoxy)phenyl group, a 4-(trifluoromethoxy)phenyl group, a 3-t-butylphenyl group, a 2,4-dichlorophenyl group, a 2,4-difluorophenyl group, a 2,3-dichlorophenyl group, a 2,3-difluorophenyl group, a 3,4-dichlorophenyl group, a 3,4-difluorophenyl group, a 2,4,6-trifluorophenyl group and a 2,4,6-trichlorophenyl group.

Examples of the "C3-C7 cycloalkoxy group optionally substituted with a group selected from the group consisting of halogen atoms, C1-C3 alkyl groups and C1-C3 haloalkyl groups" include a cyclopropoxy group, a cyclobutoxy group, a cyclopentyloxy group and a cyclohexyloxy group.

Examples of the present compound include the pyridine compounds as follows.

The pyridine compounds of the general formula (1) wherein $R^1$ is a C1-C3 haloalkyl group optionally substituted with a group selected from the group consisting of C1-C3 alkoxy groups, C3-C7 alkenyloxy groups, tri(C1-C4 alkyl)silyloxy groups and a hydroxyl group, or a C1-C3 haloalkoxy group optionally substituted with a group selected from the group consisting of C1-C3 alkoxy groups, C3-C7 alkenyloxy groups, tri(C1-C4 alkyl)silyloxy groups and a hydroxyl group;

The pyridine compounds of the general formula (1) wherein $R^1$ is a C1-C3 haloalkyl group optionally substituted with a C1-C3 alkoxy group or a C1-C3 haloalkoxy group;

The pyridine compounds of the general formula (1) wherein $R^1$ is a C1-C3 fluoroalkyl group optionally substituted with a C1-C3 alkoxy group or a C1-C3 fluoroalkoxy group;

The pyridine compounds of the general formula (1) wherein $R^1$ is a C1-C3 fluoroalkyl group or a C1-C3 fluoroalkoxy group, and $R^7$ is a C1-C7 chain hydrocarbon group optionally substituted with a halogen atom; a benzyl group optionally substituted with a group selected from the group consisting of halogen atoms, a cyano group, a nitro group, C1-C3 alkyl groups, C1-C3 haloalkyl groups and C1-C3 alkoxy groups; or a C3-C7 cycloalkyl group optionally substituted with a group consisting of halogen atoms, C1-C3 alkyl groups and C1-C3 haloalkyl groups;

The pyridine compounds of the general formula (1) wherein $R^2$ is a C1-C7 alkyl group; a cyanomethyl group; a hydrogen atom; a cyclopropylmethyl group optionally substituted with a C1-C3 alkyl group; a benzyl group optionally substituted with a group selected from the group consisting of halogen atoms, a cyano group, a nitro group, C1-C3 alkyl groups, C1-C3 haloalkyl groups and C1-C3 alkoxy groups, or a group

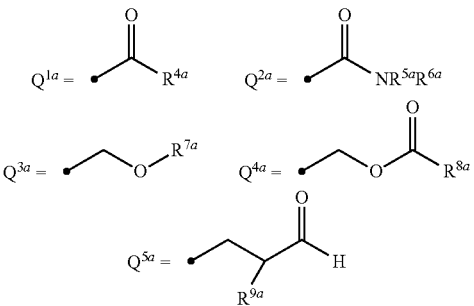

represented by any one of the formulae $Q^{1a}$ to $Q^{5a}$:
wherein $R^{4a}$ is a C1-C7 alkyl group, a C1-C7 haloalkyl group, or a C3-C7 cycloalkyl group optionally substituted with a group selected from the group consisting of halogen atoms, C1-C3 alkyl groups and C1-C3 haloalkyl groups, $R^{5a}$ and $R^{6a}$ may be the same or different, and each represents a C1-C7 alkyl group, a C1-C7 haloalkyl group, a C3-C7 alkenyl group or a C1-C7 alkoxy group, or $R^{5a}$ and $R^{6a}$ may be taken together with a nitrogen atom constituting —$NR^{5a}R^{6a}$ to form a pyrrolidin-1-yl group, a piperidino group, a hexamethyleneimin-1-yl group, a morpholino group or a thiomorpholin-4-yl group, where the pyrrolidin-1-yl group, the piperidino group, the hexamethyleneimin-1-yl group, the morpholino group and the thiomorpholin-4-yl group may be each substituted with a group selected from the group consisting of halogen atoms, C1-C3 alkyl groups and C1-C3 haloalkyl groups, $R^{7a}$ is a benzyl group optionally substituted with a group selected from the group consisting of halogen atoms, a cyano group, a nitro group, C1-C3 alkyl groups, C1-C3 haloalkyl groups and C1-C3 alkoxy groups; a C3-C7 cycloalkyl group optionally substituted with a group selected from the group consisting of halogen atoms, C1-C3 alkyl groups and C1-C3 haloalkyl groups; a C1-C7 alkyl group; or a C1-C7 haloalkyl group, $R^{8a}$ is a phenyl group optionally substituted with a group selected from the group consisting of halogen atoms, a cyano group, a nitro group, C1-C3 alkyl groups, C1-C3 haloalkyl groups, C1-C3 alkoxy groups and C1-C3 haloalkoxy groups; a C3-C7 cycloalkyl group optionally substituted with a group selected from the group consisting of halogen atoms, C1-C3 alkyl groups and C1-C3 haloalkyl groups; a C1-C7 alkyl group; or a C1-C7 haloalkyl group, $R^{9a}$ is a hydrogen atom or a C1-C3 alkyl group, and $R^3$ is a C3-C7 cycloalkyl group optionally substituted with a group selected from the group consisting of halogen atoms, C1-C3 alkyl groups and C1-C3 haloalkyl groups; a C3-C7 cycloalkoxy group optionally substituted with a group selected from the group consisting of halogen atoms, C1-C3 alkyl groups and C1-C3 haloalkyl groups; a halogen atom; a C1-C7 alkyl group; a C1-C3 haloalkyl group; a C1-C7 alkoxy group; or a C1-C3 haloalkoxy group;

The pyridine compounds of the general formula (1) wherein $R^2$ is a cyclopropylmethyl group optionally substituted with a C1-C3 alkyl group; a cyanomethyl group; a C1-C7 alkyl group; a hydrogen atom; a benzyl group optionally substituted with a group selected from the group consisting of halogen atoms, a cyano group, a nitro group, C1-C3 alkyl groups, C1-C3 haloalkyl groups and C1-C3 alkoxy groups; or a group represented by any one of the formulae $Q^{1a}$ to $Q^{5a}$, and $R^3$ is a C3-C7 cycloalkyl group optionally substituted with a group selected from the group consisting of halogen atoms, C1-C3 alkyl groups and C1-C3 haloalkyl groups; a C3-C7 cycloalkoxy group optionally substituted with a group selected from the group consisting of halogen atoms, C1-C3 alkyl groups and C1-C3 haloalkyl groups; a halogen atom; a C1-C7 alkyl group; a C1-C3 haloalkyl group; a C1-C7 alkoxy group; or a C1-C3 haloalkoxy group;

The pyridine compounds of the general formula (1) wherein $R^1$ is a C1-C3 haloalkyl group optionally substituted with a group selected from the group consisting of C1-C3 alkoxy groups, C3-C7 alkenyloxy groups, tri(C1-C4 alkyl) silyloxy groups and a hydroxyl group, or a C1-C3 haloalkoxy group, $R^2$ is a cyclopropylmethyl group optionally substituted with a C1-C3 alkyl group; a cyanomethyl group; a C1-C7 alkyl group; a hydrogen atom; a benzyl group; or a group represented by any one of the formulae $Q^{1a}$ to $Q^{4a}$, wherein $R^{4a}$ represents a C3-C7 cycloalkyl group or a C1-C7 alkyl group, $R^{5a}$ and $R^{6a}$ may be the same or different, and each represents a C1-C7 alkyl group, a C2-C5 alkenyl group or a C1-C7 alkoxy group, or $R^{5a}$ and $R^{6a}$ may be taken together with a nitrogen atom constituting $-NR^{5a}R^{6a}$ to represent a pyrrolidin-1-yl group, a piperidino group, a haxamethylene-imin-1-yl group, a morpholino group or a thiomorpholin-4-yl group, $R^{7a}$ represents a phenyl group or a benzyl group, $R^{8a}$ represents a C1-C3 alkyl group; or a phenyl group optionally substituted with a group selected from the group consisting of halogen atoms, C1-C3 alkyl groups, C1-C3 haloalkyl groups, C1-C3 alkoxy groups and C1-C3 haloalkoxy groups, and $R^3$ is a C3-C7 cycloalkyl group, a halogen atom or a C1-C7 alkyl group;

The pyridine compounds of the general formula (1) wherein $R^1$ is a C1-C3 haloalkyl group;

The pyridine compounds of the general formula (1) wherein $R^1$ is a C1-C3 haloalkoxy group;

The pyridine compounds of the general formula (1) wherein $R^2$ is a hydrogen atom;

The pyridine compounds of the general formula (1) wherein $R^2$ is a group represented by $Q^1$;

The pyridine compounds of the general formula (1) wherein $R^2$ is a group represented by $Q^2$;

The pyridine compounds of the general formula (1) wherein $R^2$ is a group represented by $Q^3$;

The pyridine compounds of the general formula (1) wherein $R^2$ is a group represented by $Q^4$;

The pyridine compounds of the general formula (1) wherein $R^2$ is a group represented by $Q^{2a}$;

The pyridine compounds of the general formula (1) wherein $R^2$ is a group represented by $Q^{3a}$;

The pyridine compounds of the general formula (1) wherein $R^2$ is a group represented by $Q^{4a}$;

The pyridine compounds of the general formula (1) wherein $R^3$ is a hydrogen atom;

The pyridine compounds of the general formula (1) wherein $R^1$ is a C1-C3 fluoroalkyl group;

The pyridine compounds of the general formula (1) wherein $R^1$ is a trifluoromethyl group;

The pyridine compounds of the general formula (1) wherein $R^1$ is a pentafluoroethyl group;

The pyridine compounds of the general formula (1) wherein $R^1$ is a C1-C3 fluoroalkoxy group;

The pyridine compounds of the general formula (1) wherein $R^1$ is a C1-C3 fluoroalkyl group, and $R^2$ is a hydrogen atom;

The pyridine compounds of the general formula (1) wherein $R^1$ is a C1-C3 fluoroalkyl group, and $R^2$ is a group represented by $Q^1$;

The pyridine compounds of the general formula (1) wherein $R^1$ is a C1-C3 fluoroalkyl group, and $R^2$ is a group represented by $Q^2$;

The pyridine compounds of the general formula (1) wherein $R^1$ is a C1-C3 fluoroalkyl group, and $R^2$ is a group represented by $Q^3$;

The pyridine compounds of the general formula (1) wherein $R^1$ is a C1-C3 fluoroalkyl group, and $R^2$ is a group represented by $Q^4$;

The pyridine compounds of the general formula (1) wherein $R^1$ is a C1-C3 fluoroalkyl group, and $R^2$ is a group represented by $Q^5$;

The pyridine compounds of the general formula (1) wherein $R^1$ is a C1-C3 fluoroalkyl group, and $R^2$ is a group represented by $Q^{1a}$;

The pyridine compounds of the general formula (1) wherein $R^1$ is a C1-C3 fluoroalkyl group, and $R^2$ is a group represented by $Q^{2a}$;

The pyridine compounds of the general formula (1) wherein $R^1$ is a C1-C3 fluoroalkyl group, and $R^2$ is a group represented by $Q^{3a}$;

The pyridine compounds of the general formula (1) wherein $R^1$ is a C1-C3 fluoroalkyl group, and $R^2$ is a group represented by $Q^{4a}$;

The pyridine compounds of the general formula (1) wherein $R^1$ is a C1-C3 fluoroalkyl group, and $R^2$ is a group represented by $Q^{5a}$;

The pyridine compounds of the general formula (1) wherein $R^1$ is a C1-C3 fluoroalkyl group, and $R^3$ is a hydrogen atom;

The pyridine compounds of the general formula (1) wherein $R^1$ is a C1-C3 fluoroalkoxy group, and $R^2$ is a hydrogen atom;

The pyridine compounds of the general formula (1) wherein $R^1$ is a C1-C3 fluoroalkoxy group, and $R^2$ is a group represented by $Q^1$;

The pyridine compounds of the general formula (1) wherein $R^1$ is a C1-C3 fluoroalkoxy group, and $R^2$ is a group represented by $Q^2$;

The pyridine compounds of the general formula (1) wherein $R^1$ is a C1-C3 fluoroalkoxy group, and $R^2$ is a group represented by $Q^3$;

The pyridine compounds of the general formula (1) wherein $R^1$ is a C1-C3 fluoroalkoxy group, and $R^2$ is a group represented by $Q^4$;

The pyridine compounds of the general formula (1) wherein $R^1$ is a C1-C3 fluoroalkoxy group, and $R^2$ is a group represented by $Q^5$;

The pyridine compounds of the general formula (1) wherein $R^1$ is a C1-C3 fluoroalkoxy group, and $R^2$ is a group represented by $Q^{1a}$;

The pyridine compounds of the general formula (1) wherein $R^1$ is a C1-C3 fluoroalkoxy group, and $R^2$ is a group represented by $Q^{2a}$;

The pyridine compounds of the general formula (1) wherein $R^1$ is a C1-C3 fluoroalkoxy group, and $R^2$ is a group represented by $Q^{3a}$;

The pyridine compounds of the general formula (1) wherein $R^1$ is a C1-C3 fluoroalkoxy group, and $R^2$ is a group represented by $Q^{4a}$;

The pyridine compounds of the general formula (1) wherein $R^1$ is a C1-C3 fluoroalkoxy group, and $R^2$ is a group represented by $Q^{5a}$;

The pyridine compounds of the general formula (1) wherein $R^1$ is a C1-C3 fluoroalkoxy group, and $R^3$ is a hydrogen atom;

The pyridine compounds of the general formula (1) wherein $R^1$ is a trifluoromethyl group, and $R^2$ is a hydrogen atom;

The pyridine compounds of the general formula (1) wherein $R^1$ is a trifluoromethyl group, and $R^2$ is a group represented by $Q^1$;

The pyridine compounds of the general formula (1) wherein $R^1$ is a trifluoromethyl group, and $R^2$ is a group represented by $Q^2$;

The pyridine compounds of the general formula (1) wherein $R^1$ is a trifluoromethyl group, and $R^2$ is a group represented by $Q^3$;

The pyridine compounds of the general formula (1) wherein $R^1$ is a trifluoromethyl group, and $R^2$ is a group represented by $Q^4$;

The pyridine compounds of the general formula (1) wherein $R^1$ is a trifluoromethyl group, and $R^2$ is a group represented by $Q^5$;

The pyridine compounds of the general formula (1) wherein $R^1$ is a pentafluoroethyl group, and $R^2$ is a hydrogen atom;

The pyridine compounds of the general formula (1) wherein $R^1$ is a pentafluoroethyl group, and $R^2$ is a group represented by $Q^1$;

The pyridine compounds of the general formula (1) wherein $R^1$ is a pentafluoroethyl group, and $R^2$ is a group represented by $Q^2$;

The pyridine compounds of the general formula (1) wherein $R^1$ is a pentafluoroethyl group, and $R^2$ is a group represented by $Q^3$;

The pyridine compounds of the general formula (1) wherein $R^1$ is a pentafluoroethyl group, and $R^2$ is a group represented by $Q^4$;

The pyridine compounds of the general formula (1) wherein $R^1$ is a pentafluoroethyl group, and $R^2$ is a group represented by $Q^5$;

The pyridine compounds of the general formula (1) wherein $R^1$ is a trifluoromethyl group, and $R^2$ is a group represented by $Q^{1a}$;

The pyridine compounds of the general formula (1) wherein $R^1$ is a trifluoromethyl group, and $R^2$ is a group represented by $Q^{2a}$;

The pyridine compounds of the general formula (1) wherein $R^1$ is a trifluoromethyl group, and $R^2$ is a group represented by $Q^{3a}$;

The pyridine compounds of the general formula (1) wherein $R^1$ is a trifluoromethyl group, and $R^2$ is a group represented by $Q^{4a}$;

The pyridine compounds of the general formula (1) wherein $R^1$ is a trifluoromethyl group, and $R^2$ is a group represented by $Q^{5a}$;

The pyridine compounds of the general formula (1) wherein $R^1$ is a pentafluoroethyl group, and n is 0;

The pyridine compounds of the general formula (1) wherein $R^1$ is a C1-C3 fluoroalkyl group, $R^2$ is a hydrogen atom, and n is 0;

The pyridine compounds of the general formula (1) wherein $R^1$ is a C1-C3 fluoroalkyl group, $R^2$ is a group represented by $Q^1$, and n is 0;

The pyridine compounds of the general formula (1) wherein $R^1$ is a C1-C3 fluoroalkyl group, $R^2$ is a group represented by $Q^2$, and n is 0;

The pyridine compounds of the general formula (1) wherein $R^1$ is a C1-C3 fluoroalkyl group, $R^2$ is a group represented by $Q^3$, and n is 0;

The pyridine compounds of the general formula (1) wherein $R^1$ is a C1-C3 fluoroalkyl group, $R^2$ is a group represented by $Q^4$, and n is 0;

The pyridine compounds of the general formula (1) wherein $R^1$ is a C1-C3 fluoroalkyl group, $R^2$ is a group represented by $Q^5$, and n is 0;

The pyridine compounds of the general formula (1) wherein $R^1$ is a C1-C3 fluoroalkoxy group, $R^2$ is a hydrogen atom, and n is 0;

The pyridine compounds of the general formula (1) wherein $R^1$ is a C1-C3 fluoroalkoxy group, $R^2$ is a group represented by $Q^1$, and n is 0;

The pyridine compounds of the general formula (1) wherein $R^1$ is a C1-C3 fluoroalkoxy group, $R^2$ is a group represented by $Q^2$, and n is 0;

The pyridine compounds of the general formula (1) wherein $R^1$ is a C1-C3 fluoroalkoxy group, $R^2$ is a group represented by $Q^3$, and n is 0;

The pyridine compounds of the general formula (1) wherein $R^1$ is a C1-C3 fluoroalkoxy group, $R^2$ is a group represented by $Q^4$, and n is 0;

The pyridine compounds of the general formula (1) wherein $R^1$ is a C1-C3 fluoroalkoxy group, $R^2$ is a group represented by $Q^5$, and n is 0;

The pyridine compounds of the general formula (1) wherein $R^1$ is a pentafluoroethyl group, $R^2$ is a hydrogen atom, and n is 0;

The pyridine compounds of the general formula (1) wherein $R^1$ is a pentafluoroethyl group, $R^2$ is a group represented by $Q^1$, and n is 0;

The pyridine compounds of the general formula (1) wherein $R^1$ is a pentafluoroethyl group, $R^2$ is a group represented by $Q^2$, and n is 0;

The pyridine compounds of the general formula (1) wherein $R^1$ is a pentafluoroethyl group, $R^2$ is a group represented by $Q^3$, and n is 0;

The pyridine compounds of the general formula (1) wherein $R^1$ is a pentafluoroethyl group, $R^2$ is a group represented by $Q^4$, and n is 0;

The pyridine compounds of the general formula (1) wherein $R^1$ is a pentafluoroethyl group, $R^2$ is a group represented by $Q^5$, and n is 0.

Then, a method of producing the present compound will be described.

The present compound can be produced, for example, according to the following Production Methods 1 to 3.

<Production Method 1>

A method of producing the present compounds in which $R^2$ is a group other than a hydrogen atom.

The present compound represented by the general formula (1-1) can be produced by the following process (I):

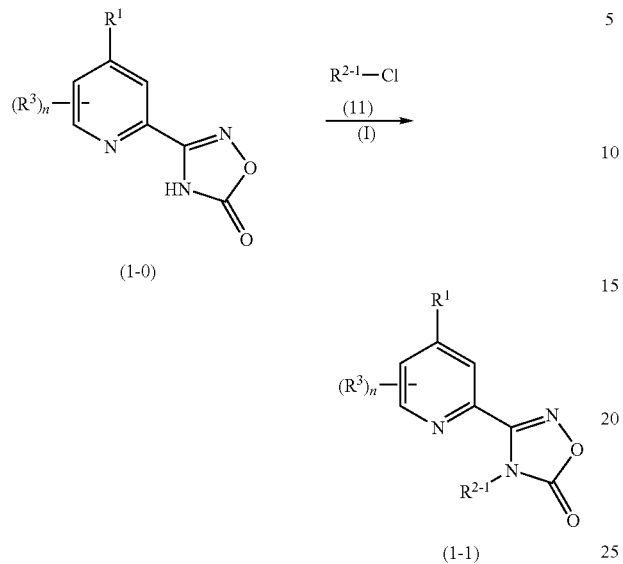

wherein $R^1$, $R^3$ and n are as defined above, and $R^{2-1}$ represents a group other than a hydrogen atom among groups represented by $R^2$.

In the process (I), the compound represented by the general formula (1-0) and the compound of the general formula (11) are reacted in the presence of a base.

The reaction is usually performed in a solvent. Examples of the solvent include ethers such as 1,4-dioxane, diethyl ether, tetrahydrofuran, and tert-butyl=methyl=ether; hydrocarbons such as toluene, benzene, and xylene; nitriles such as acetonitrile; aprotic polar solvents such as N,N-dimethylformamide, N-methylpyrrolidone, and dimethyl sulfoxide; nitrogen-containing heterocyclic compounds such as pyridine, picoline, and 2,6-lutidine; a mixture thereof.

The base can be arbitrarily selected depending on the solvent used in the reaction. Examples of the base include inorganic bases such as sodium hydride, carbonates such as potassium carbonate, nitrogen-containing heterocyclic compounds such as 1,8-diazabicyclo[5,4,0]7-undecene, and 1,5-diazabicyclo[4,3,0]5-nonene, and tertiary amines such as triethylamine, and N,N-diisopropylethylamine. The amount of the base in the reaction is usually 1 to 3 moles per mole of the compound of the general formula (1-0). The amount of the compound of the general formula (11) in the reaction is usually 1 to 3 moles per mole of the compound of the general formula (1-0). The reaction temperature of the reaction is usually in the range of 0 to 120° C. The reaction time is usually in the range of 0.1 to 36 hours.

By subjecting the reaction mixture after completion of the reaction to conventional workup such as organic solvent extraction and concentration, a compound of the general formula (1-1) can be isolated. The isolated compound of the general formula (1-1) may be further purified by recrystallization, chromatography or the like.

<Production Method 2>

A method of producing the present compounds in which $R^2$ is a hydrogen atom.

The compound of the general formula (1-0) can be produced from the compound of the general formula (4) via the process (II-1) and the process (II-2) as described in the following scheme:

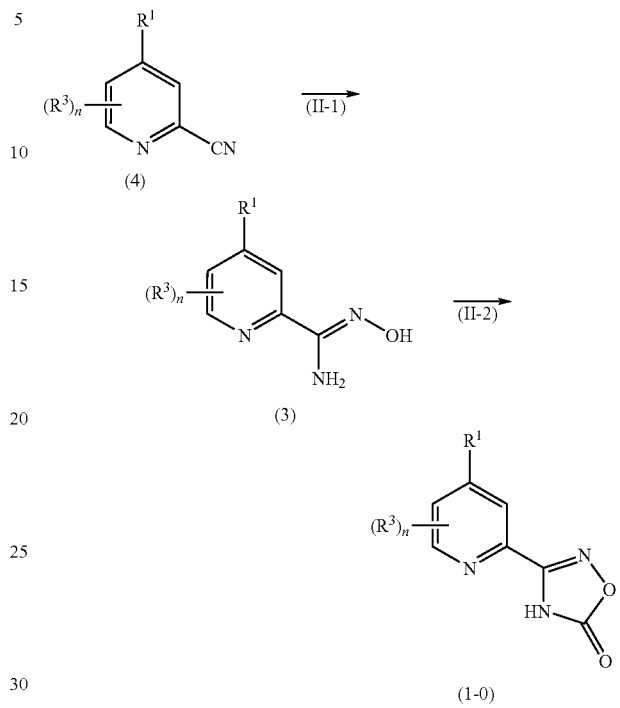

wherein $R^1$, $R^3$ and n are as defined above.

Process (II-1)

The compound of the general formula (3) can be produced by reacting the compound of the general formula (4) with hydroxylamine in the presence of a base.

The reaction is usually performed in a solvent. Examples of the solvent include alcohols such as methanol, ethanol and 2-propanol, water and a mixture thereof.

Examples of the base include inorganic bases such as sodium hydride, carbonates such as potassium carbonate. The amount of the base in the reaction is usually 1 to 4 moles per mole of the compound of the general formula (4).

Examples of the hydroxylamine include hydroxylamine, hydroxylamine hydrochloride, hydroxylamine sulfate. The amount of hydroxylamine in the reaction is usually 1 to 3 moles per mole of the compound of the general formula (4). The reaction temperature of the reaction is usually in the range of 0 to 120° C. The reaction time is usually in the range of 0.1 to 48 hours.

By subjecting the reaction mixture after completion of the reaction to conventional workup such as organic solvent extraction and concentration, the compound of the general formula (3) can be isolated. The isolated compound of the general formula (3) may be further purified by recrystallization, chromatography or the like.

Process (II-2)

The compound of the general formula (1-0) can be produced by reacting the compound of the general formula (3) and a carbonylating agent in the presence of a base.

The reaction is usually performed in a solvent. Examples of the solvent include ethers such as 1,4-dioxane, diethyl ether, tetrahydrofuran and tert-butyl=methyl=ether; halogenated hydrocarbons such as dichloromethane, chloroform, carbon tetrachloride, 1,2-dichloroethane and chlorobenzene; hydrocarbons such as toluene, benzene and xylene; nitriles such as acetonitrile; aprotic polar solvents such as N,N-dimethylformamide, N-methylpyrrolidone and dimethyl sulfoxide; and a mixture thereof.

Examples of the base include nitrogen-containing heterocyclic compounds such as pyridine, picoline, 2,6-lutidine, 1,8-diazabicyclo[5,4,0]7-undecene and 1,5-diazabicyclo[4,3,0]5-nonene, and tertiary amines such as triethylamine and N,N-diisopropylethylamine. The amount of the base in the reaction is usually 1 to 3 moles per mole of the compound of the general formula (3).

Examples of the carbonylating agent include phosgene, 1,1'-carbonyldiimidazole. The amount of the carbonylating agent in the reaction is usually 1 to 3 moles per mole of the compound of the general formula (3).

The reaction temperature of the reaction is usually in the range of 0 to 100° C. The reaction time is usually in the range of 0.1 to 48 hours.

By subjecting the reaction mixture after completion of the reaction to conventional workup such as organic solvent extraction and concentration, the compound of the general formula (1-0) can be isolated. The isolated compound of the general formula (1-0) may be further purified by recrystallization, chromatography or the like.

<Production Method 3>

A method of producing the present compounds in which $R^2$ is a group represented by $Q^5$.

The present compound of the general formula (1-3) can be produced by the following process (III):

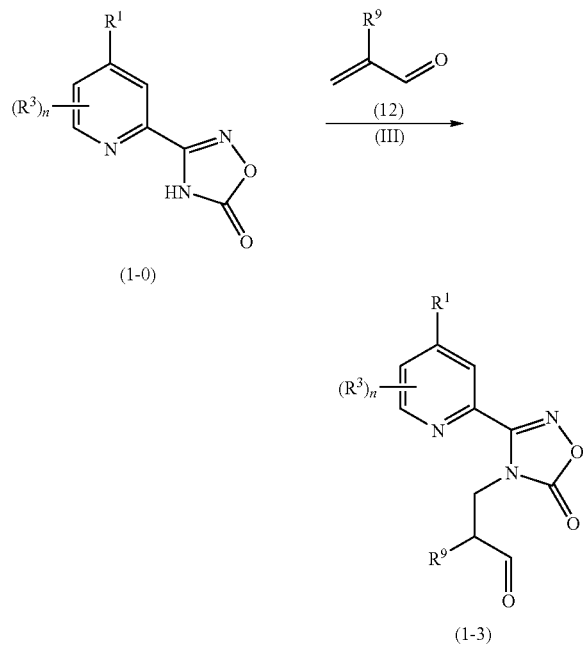

wherein $R^1$, $R^3$, $R^9$ and n are as defined above.

The process (III) is the process of reacting the compound of the general formula (1-0) with the compound of the general formula (12) in the presence of a base.

The reaction is usually performed in a solvent. Examples of the solvent include alcohols such as methanol and ethanol, halogenated hydrocarbons such as chloroform and dichloromethane, and a mixture thereof.

Examples of the base include nitrogen-containing heterocyclic compounds such as pyridine, picoline, 2,6-lutidine, 1,8-diazabicyclo[5,4,0]7-undecene and 1,5-diazabicyclo[4,3,0]5-nonene, and tertiary amines such as triethylamine and N,N-diisopropylethylamine. The amount of the base in the reaction is usually 1 to 3 moles per mole of the compound of the general formula (1-0).

The amount of the compound of the general formula (12) in the reaction is usually 1 to 3 moles per mole of the compound of the general formula (1-0).

The reaction temperature of the reaction is usually in the range of 0 to 100° C. The reaction time is usually in the range of 0.1 to 48 hours.

By subjecting the reaction mixture after completion of the reaction to conventional workup such as organic solvent extraction and concentration, the compound of the general formula (1-3) can be isolated. The isolated compound of the general formula (1-3) may be further purified by recrystallization, chromatography or the like.

Then, a method of producing an intermediate for producing the present compound will be described.

<Reference Production Method A>

The compound of the general formula (4) can be produced from the compound of the general formula (6) via the process (A-1) and the process (A-2) as shown in the following scheme:

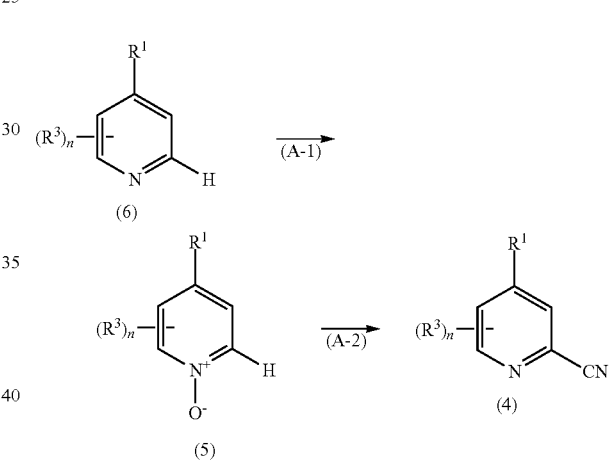

wherein $R^1$, $R^3$ and n are as defined above.

Process (A-1)

The compound of the general formula (5) can be produced by reacting the compound of the general formula (6) with peroxide.

The reaction is usually performed in a solvent. Examples of the solvent include halogenated hydrocarbons such as dichloromethane, chloroform, carbon tetrachloride, 1,2-dichloroethane and chlorobenzene, and a mixture thereof.

Examples of the peroxide include m-chloroperbenzoic acid, aqueous hydrogen peroxide, peracetic acid. The amount of the peroxide in the reaction is usually 1 to 3 moles per mole of the compound of the general formula (6).

The reaction temperature of the reaction is usually in the range of 0 to 100° C. The reaction time is usually in the range of 0.1 to 72 hours.

By subjecting the reaction mixture after completion of the reaction to conventional workup such as organic solvent extraction and concentration, the compound of the general formula (5) can be isolated. The isolated compound of the general formula (5) may be further purified by chromatography or the like.

Process (A-2)

The compound of the general formula (4) can be produced by reacting the compound of the general formula (5) with a cyanizing agent in the presence of a base.

The reaction is usually performed in a solvent. Examples of the solvent include ethers such as 1,4-dioxane, diethyl ether, tetrahydrofuran and tert-butyl=methyl=ether; hydrocarbons such as toluene, benzene and xylene; nitriles such as acetonitrile; aprotic polar solvents such as N,N-dimethylformamide, N-methylpyrrolidone and dimethyl sulfoxide; and a mixture thereof.

Examples of the base include nitrogen-containing heterocyclic compounds such as pyridine, picoline, 2,6-lutidine, 1,8-diazabicyclo[5,4,0]7-undecene and 1,5-diazabicyclo[4,3,0]5-nonene, and tertiary amines such as triethylamine and N,N-diisopropylethylamine. The amount of the base in the reaction is usually 2 to 6 moles per mole of the compound of the general formula (5).

Examples of the cyanizing agent include trimethylsilyl cyanide. The amount of the cyanizing agent in the reaction is usually 2 to 6 moles per mole of the compound of the general formula (5).

The reaction temperature of the reaction is usually in the range of 0 to 120° C. The reaction time is usually in the range of 0.1 to 72 hours.

By subjecting the reaction mixture after completion of the reaction to conventional workup such as organic solvent extraction and concentration, the compound of the general formula (4) can be isolated. The isolated compound of the general formula (4) may be further purified by chromatography or the like.

<Reference Production Method B>

The compound of the general formula (4-B) can be produced from the compound of the general formula (7) via the process (B):

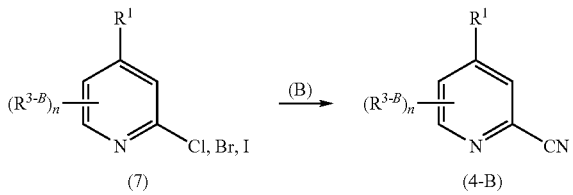

wherein $R^1$, and n are as defined above, $R^{3-B}$ represents a C3-C7 cycloalkyl group optionally substituted with a C1-C3 alkyl group; a C3-C7 cycloalkoxy group optionally substituted with a C1-C3 alkyl group; a C1-C7 chain hydrocarbon group; a C1-C7 alkoxy group; or a fluorine atom.

Process (B)

The compound of the general formula (4-B) can be produced by reacting the compound of the general formula (7) with zinc cyanide in the presence of a transition metal compound.

The reaction is usually performed in a solvent. Examples of the solvent include ethers such as 1,4-dioxane, diethyl ether, tetrahydrofuran and tert-butyl=methyl=ether; hydrocarbons such as toluene, benzene and xylene; nitriles such as acetonitrile; aprotic polar solvents such as N,N-dimethylformamide, N-methylpyrrolidone and dimethyl sulfoxide; and a mixture thereof.

Examples of the transition metal compound include a palladium compound, specifically, palladium acetate, tetrakis(triphenylphosphine)palladium, {1,1'-bis(diphenylphosphino)ferrocene}dichloropalladium (II) methylene chloride complex, bis(triphenylphosphine)palladium (II) chloride. The amount of the transition metal compound in the reaction can be changed as long as the reaction can proceed, and is usually 0.01 to 0.1 mole per mole of the compound of the general formula (7).

The amount of zinc cyanide in the reaction is usually 0.5 to 2 moles per mole of the compound of the general formula (7).

The reaction temperature of the reaction is usually in the range of 0 to 150° C. The reaction time is usually in the range of 0.1 to 72 hours.

By subjecting the reaction mixture after completion of the reaction to conventional workup such as organic solvent extraction and concentration, the compound of the general formula (4-B) can be isolated. The isolated compound of the general formula (4-B) may be further purified by chromatography or the like.

<Reference Production Method C>

The compound of the general formula (4-C) can be produced from the compound of the general formula (8) via the process (C):

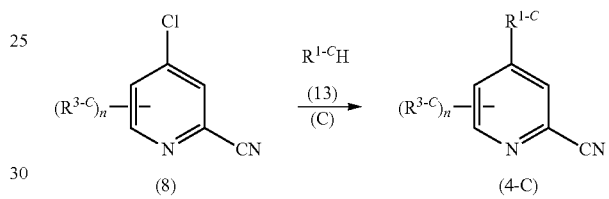

wherein n is as defined above, $R^{1-C}$ represents a C1-C7 haloalkoxy group optionally substituted with a group selected from the group consisting of C1-C3 alkoxy groups, C1-C3 haloalkoxy groups, C3-C7 alkenyloxy groups, C3-C7 haloalkenyloxy groups, C3-C7 alkynyloxy groups, C3-C7 haloalkynyloxy groups, tri(C1-C4 alkyl)silyloxy groups and a hydroxy group, $R^{3-C}$ represents a C3-C7 cycloalkyl group optionally substituted with a C1-C3 alkyl group; a C3-C7 cycloalkoxy group optionally substituted with a C1-C3 alkyl group; a C1-C7 chain hydrocarbon group; or a C1-C7 alkoxy group.

Process (C)

The compound of the general formula (4-C) can be produced by reacting the compound of the general formula (8) with the compound of the general formula (13) in the presence of a base.

The reaction is usually performed in a solvent. Examples of the solvent include ethers such as 1,4-dioxane, diethyl ether, tetrahydrofuran and tert-butyl=methyl=ether; hydrocarbons such as toluene, benzene and xylene; nitriles such as acetonitrile; aprotic polar solvents such as N,N-dimethylformamide, N-methylpyrrolidone and dimethyl sulfoxide; and a mixture thereof.

Examples of the base include inorganic bases such as sodium hydride, carbonates such as potassium carbonate. The amount of the base in the reaction is usually 1 to 3 moles per mole of the compound of the general formula (8).

The amount of the compound of the general formula (13) in the reaction is usually 1 to 3 moles per mole of the compound of the general formula (8).

The reaction temperature of the reaction is usually in the range of 0 to 100° C. The reaction time is usually in the range of 0.1 to 12 hours.

By subjecting the reaction mixture after completion of the reaction to conventional workup such as organic solvent extraction and concentration, the compound of the general formula (4-C) can be isolated. The isolated compound of the general formula (4-C) may be further purified by chromatography or the like.

<Reference Production Method D>

The compound of the general formula (6) or the general formula (7) can be produced from the compound of the general formula (9).

The compound of the general formula (9) can be produced from the compound of the general formula (10) via the process (D):

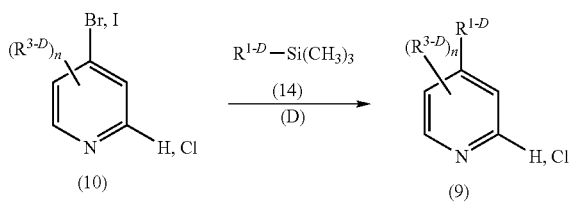

wherein n is as defined above, $R^{1-D}$ represents a C1-C7 perfluoroalkyl group, $R^{3-D}$ represents a C3-C7 cycloalkyl group optionally substituted with a group selected from the group consisting of halogen atoms, C1-C3 alkyl groups and C1-C3 haloalkyl groups; a C3-C7 cycloalkoxy group optionally substituted with a group selected from the group consisting of halogen atoms, C1-C3 alkyl groups and C1-C3 haloalkyl groups; a C1-C7 chain hydrocarbon group optionally substituted with a halogen atom; a chlorine atom; a fluorine atom; a C1-C7 alkoxy group; or a C1-C3 haloalkoxy group.

Process (D)

The compound of the general formula (9) can be produced by reacting the compound of the general formula (10) with potassium fluoride, copper iodide, and perfluoroalkyltrimethylsilane represented by the general formula (14).

The reaction is usually performed in a solvent. Examples of the solvent include ethers such as 1,4-dioxane, diethyl ether, tetrahydrofuran and tert-butyl=methyl=ether; hydrocarbons such as toluene, benzene and, xylene; aprotic polar solvents such as N,N-dimethylformamide, N-methylpyrrolidone and dimethyl sulfoxide; and a mixture thereof.

The amount of potassium fluoride in the reaction is usually 1 to 3 moles per mole of the compound of the general formula (10).

The amount of copper iodide in the reaction is usually 1 to 3 moles per mole of the compound of the general formula (10).

The amount of the compound of the general formula (14) is usually 1 to 3 moles per mole of the compound of the general formula (10).

The reaction temperature of the reaction is usually in the range of 0 to 180° C. The reaction time is usually in the range of 0.1 to 72 hours.

By subjecting the reaction mixture after completion of the reaction to conventional workup such as organic solvent extraction and concentration, the compound of the general formula (9) can be isolated. The isolated compound of the general formula (9) may be further purified by chromatography or the like.

<Reference Production Method E>

The compound of the general formula (13) can be produced, for example, from the compound of the general formula (15).

The compound of the general formula (15) can be produced from the compound of the general formula (16) via the process (E) under the atmosphere of a gas which is inert to a reaction, such as nitrogen and argon.

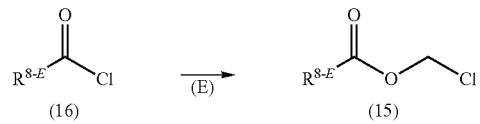

wherein $R^{8-E}$ represents a phenyl group optionally substituted with a group selected from the group consisting of halogen atoms, a cyano group, a nitro group, C1-C3 alkyl groups, C1-C3 haloalkyl groups, C1-C3 alkoxy groups and C1-C3 haloalkoxy groups.

Process (E)

The compound of the general formula (15) can be produced by reacting the compound of the general formula (16) with zirconium tetrachloride and trioxane.

The reaction is usually performed in a solvent. Examples of the solvent include ethers such as 1,4-dioxane, diethyl ether, tetrahydrofuran and tert-butyl=methyl=ether; halogenated hydrocarbons such as dichloromethane, chloroform, carbon tetrachloride, 1,2-dichloroethane and chlorobenzene; and a mixture thereof.

The amount of zirconium tetrachloride in the reaction is usually 0.9 to 2 moles per mole of the compound of the general formula (16).

The amount of trioxane in the reaction is usually 0.3 to 1 mole per mole of the compound of the general formula (16).

The reaction temperature of the reaction is usually in the range of –20 to 80° C. The reaction time is usually in the range of 0.1 to 72 hours.

By subjecting the reaction mixture after completion of the reaction to conventional workup such as organic solvent extraction and concentration, the compound of the general formula (15) can be isolated. The isolated compound of the general formula (15) may be further purified by chromatography or the like.

<Reference Production Method F>

Among the compound of the general formula (4), the compound represented by the general formula (17-6) can be produced from the aldehyde compound of the general formula (17) via the processes (F-1) to (F-6):

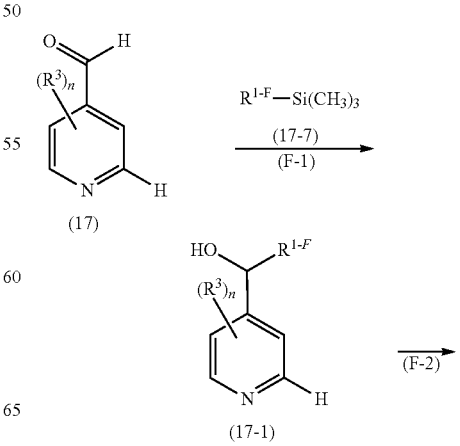

-continued (17-2)

(17-3)

(17-4)

(17-5)    (F-6)    (17-6)

wherein R³ and n are as defined above,

R¹⁻ᶠ represents a C1-C6 perfluoroalkyl group,

Rᶠ represents a C1-C3 alkyl group, a C1-C3 haloalkyl group, a C3-C7 alkenyl group, a C3-C7 haloalkenyl group, a C3-C7 alkynyl group, a C3-C7 haloalkynyl group or a tri(C1-C4 alkyl)silyl group, X represents a leaving group, for example, a chlorine atom, a bromine atom, or an iodine atom.

Process (F-1)

The alcohol compound of the general formula (17-1) can be produced by reacting the aldehyde compound of the general formula (17) with the silane compound of the general formula (17-7) in the presence of an ammonium salt.

The reaction is usually perfumed in a solvent. Examples of the solvent include halogenated hydrocarbons such as chloroform and dichloromethane; ethers such as 1,4-dioxane, diethyl ether, tetrahydrofuran and tert-butyl=methyl=ether; hydrocarbons such as toluene, benzene and xylene; aprotic polar solvents such as N,N-dimethylformamide, N-methylpyrrolidone and dimethyl sulfoxide; and a mixture thereof.

Examples of the ammonium salt include tetrabutylammonium acetate, tetrabutylammonium fluoride. The amount of the ammonium salt in the reaction is usually 0.01 to 0.5 mole per mole of the compound of the general formula (17).

The amount of the silane compound of the general formula (17-7) in the reaction is usually 1 to 3 moles per mole of the compound of the general formula (17).

The reaction temperature of the reaction is usually in the range of 0 to 180° C. The reaction time is usually in the range of 0.1 to 72 hours.

By subjecting the reaction mixture after completion of the reaction to conventional workup such as organic solvent extraction and concentration, the compound of the general formula (17-1) can be isolated. The isolated compound of the general formula (17-1) may be further purified by chromatography or the like.

Process (F-2)

The compound of the general formula (17-2) can be produced by reacting the alcohol compound of the general formula (17-1) with triethylchlorosilane in the presence of a base.

The reaction is usually performed in a solvent. Examples of the solvent include halogenated hydrocarbons such as chloroform and dichloromethane; ethers such as 1,4-dioxane, diethyl ether, tetrahydrofuran and tert-butyl=methyl=ether; aprotic polar solvents such as N,N-dimethylformamide, N-methylpyrrolidone and dimethyl sulfoxide; and a mixture thereof.

Examples of the base include nitrogen-containing heterocyclic compounds such as pyridine, picoline, 2,6-lutidine, 1,8-diazabicyclo[5,4,0]7-undecene and 1,5-diazabicyclo[4,3,0]5-nonene, and tertiary amines such as triethylamine and N,N-diisopropylethylamine. The amount of the base in the reaction is usually 1 to 3 moles per mole of the compound (17-1).

The amount of triethylchlorosilane in the reaction is usually 1 to 3 moles per mole of the compound (17-1).

The reaction temperature of the reaction is usually in the range of 0 to 180° C. The reaction time is usually in the range of 0.1 to 72 hours.

By subjecting the reaction mixture after completion of the reaction to conventional workup such as organic solvent extraction and concentration, the compound of the general formula (17-2) can be isolated. The isolated compound of the general formula (17-2) may be further purified by chromatography or the like.

Process (F-3)

The compound of the general formula (17-3) can be produced by reacting the compound of the general formula (17-2) with a peroxide.

The reaction is usually performed in a solvent. Examples of the solvent include halogenated hydrocarbons such as dichloromethane, chloroform, carbon tetrachloride, 1,2-dichloroethane and chlorobenzene and a mixture thereof.

Examples of the peroxide include m-chloroperbenzoic acid, aqueous hydrogen peroxide, peracetic acid. The amount of the peroxide in the reaction is usually 1 to 3 moles per mole of the compound (17-2).

The reaction temperature of the reaction is usually in the range of 0 to 100° C. The reaction time is usually in the range of 0.1 to 72 hours.

By subjecting the reaction mixture after completion of the reaction to conventional workup such as organic solvent extraction and concentration, the compound of the general formula (17-3) can be isolated. The isolated compound of the general formula (17-3) may be further purified by chromatography or the like.

Process (F-4)

The nitrile compound of the general formula (17-4) can be produced by reacting the compound of the general formula (17-3) with a cyanizing agent in the presence of a base.

The reaction is usually performed in a solvent. Examples of the solvent include ethers such as 1,4-dioxane, diethyl ether, tetrahydrofuran and tert-butyl=methyl=ether; hydrocarbons such as toluene, benzene and xylene; nitriles such as acetonitrile; aprotic polar solvents such as N,N-dimethylformamide, N-methylpyrrolidone and dimethyl sulfoxide; and a mixture thereof.

Examples of the base include nitrogen-containing heterocyclic compounds such as pyridine, picoline, 2,6-lutidine, 1,8-diazabicyclo[5,4,0]7-undecene and 1,5-diazabicyclo[4,3,0]5-nonene, tertiary amines such as triethylamine and N,N-diisopropylethylamine. The amount of the base in the reaction is usually 2 to 6 moles per mole of the compound (17-3).

Examples of the cyanizing agent include trimethylsilyl cyanide. The amount of the cyanizing agent in the reaction is usually 2 to 6 moles per mole of the compound (17-3).

The reaction temperature of the reaction is usually in the range of 0 to 120° C. The reaction time is usually in the range of 0.1 to 72 hours.

By subjecting the reaction mixture after completion of the reaction to conventional workup such as organic solvent extraction and concentration, the compound of the general formula (17-4) can be isolated. The isolated compound of the general formula (17-4) may be further purified by chromatography or the like.

Process (F-5)

The alcohol compound of the general formula (17-5) can be produced by reacting the compound of the general formula (17-4) with a fluorinating agent.

The reaction is usually performed in a solvent. Examples of the solvent include ethers such as 1,4-dioxane, diethyl ether, tetrahydrofuran and tert-butyl=methyl=ether; hydrocarbons such as toluene, benzene and xylene; nitriles such as acetonitriles; aprotic polar solvents such as N,N-dimethylformamide, N-methylpyrrolidone and dimethyl sulfoxide; and a mixture thereof.

Examples of the fluorinating agent include tetrabutylammonium fluoride, hydrogen fluoride. The amount of the fluorinating agent in the reaction is usually 0.1 to 3 moles per mole of the compound (17-4).

The reaction temperature of the reaction is usually in the range of 0 to 120° C. The reaction time is usually in the range of 0.1 to 72 hours.

By subjecting the reaction mixture after completion of the reaction to conventional workup such as organic solvent extraction and concentration. The compound of the general formula (17-5) can be isolated. The isolated compound of the general formula (17-5) may further purified by chromatography or the like.

Process (F-6)

The compound of the general formula (17-6) can be produced by reacting the alcohol compound of the general formula (17-5) with $R^f$—X in the presence of a base.

The reaction is usually performed in a solvent. Examples of the solvent include ethers such as 1,4-dioxane, diethyl ether, tetrahydrofuran and tert-butyl=methyl=ether: hydrocarbons such as toluene, benzene and xylene; nitriles such as acetonitrile; aprotic polar solvents such as N,N-dimethylformamide, N-methylpyrrolidone and dimethyl sulfoxide; and a mixture thereof.

Examples of the base include inorganic bases such as sodium hydride, carbonates such as potassium carbonate, nitrogen-containing heterocyclic compounds such as 1,8-diazabicyclo[5,4,0]7-undecene and 1,5-diazabicyclo[4,3,0]5-nonene, tertiary amines such as triethylamine and N,N-diisopropylethylamine, and the base can be arbitrarily selected depending on the solvent in the reaction. The amount of the base in the reaction is usually 1 to 3 moles per mole of the alcohol compound of the general formula (17-5). The amount of the compound of $R^f$—X in the reaction is usually in the range of 1 to 3 moles per mole of the alcohol compound of the general formula (17-5). The reaction temperature of the reaction is usually in the range of 0 to 120° C. The reaction time is usually in the range of 0.1 to 36 hours.

By subjecting the reaction mixture after completion of the reaction to conventional workup such as organic solvent extraction and concentration, the compound of the general formula (17-6) can be isolated. The isolated compound of the general formula (17-6) may be further purified by recrystallization, chromatography or the like.

<Reference Production Method G>

The compound of the general formula (6) can be produced from the compound of the general formula (18-1).

The compound of the general formula (18-1) can be produced by reacting the ketone compound of the general formula (18) with the silane compound of the general formula (18-2) in the presence of an ammonium salt.

wherein $R^3$ and n are as defined above, $R^{1-G}$ represents a C1-C3 perfluoroalkyl group, $R^g$ represents a C1-C3 alkyl group or a C1-C3 haloalkyl group.

Process (G)

The compound of the general formula (18-1) can be produced by reacting the ketone compound of the general formula (18) with the silane compound of the general formula (18-2) in the presence of an ammonium salt.

The reaction is usually performed in a solvent. Examples of the solvent include halogenated hydrocarbons such as chloroform and dichloromethane; ethers such as 1,4-dioxane, diethyl ether, tetrahydrofuran and tert-butyl=methyl=ether; hydrocarbons such as toluene, benzene and xylene: aprotic polar solvents such as N,N-dimethylformamide, N-methylpyrrolidone and dimethyl sulfoxide; and a mixture thereof.

Examples of the ammonium salt include tetrabutylammonium acetate, tetrabutylammonium fluoride. The amount of the ammonium salt in the reaction is usually 0.01 to 0.5 mole per mole of the compound of the general formula (18).

The amount of the silane compound of the general formula (18-2) in the reaction is usually 1 to 3 moles per mole of the compound of the general formula (18).

The reaction temperature of the reaction is usually in the range of 0 to 180° C. The reaction time is usually in the range of 0.1 to 72 hours.

By subjecting the reaction mixture after completion of the reaction to conventional workup such as organic solvent extraction and concentration, the compound of the general formula (18-1) can be isolated. The isolated compound of the general formula (18-1) may be further purified by chromatography or the like.

<Reference Production Method H>

The compound of the general formula (6) can be produced from the compound of the general formula (19-2).

The pyridine compound of the general formula (19-2) can be produced from the compound of the general formula (19) via the processes (H-1) and (H-2).

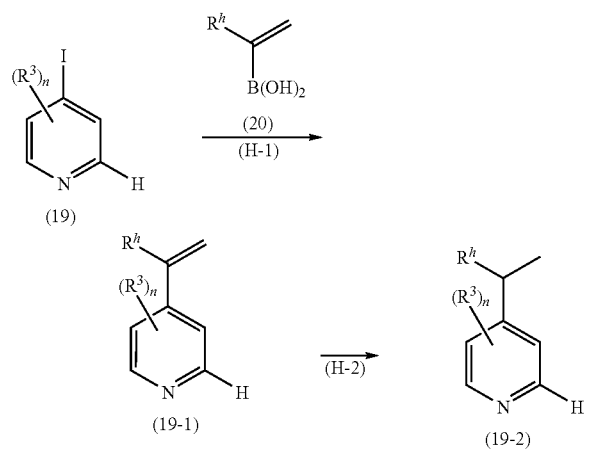

wherein $R^3$ and n are as defined above, and
$R^h$ represents a C1-C5 haloalkyl group.

Process (H-1)

The compound of the general formula (19-1) can be produced by reacting the compound of the general formula (19) with the borane compound of the general formula (20) in the presence of a transition metal compound and a base.

The reaction is usually performed in a solvent. Examples of the solvent include water; ethers such as 1,4-dioxane, diethyl ether, tetrahydrofuran and tert-butyl=methyl=ether; hydrocarbons such as toluene, benzene and xylene; nitriles such as acetonitrile; aprotic polar solvents such as N,N-dimethylformamide, N-methylpyrrolidone and dimethyl sulfoxide; and a mixture thereof.

Examples of the transition metal compound include a palladium compound, specifically, palladium acetate, tetrakis (triphenyl phosphine)palladium, {1,1'-bis(diphenylphosphino)ferrocene}dichloropalladium(II) methylene chloride complex and bis(triphenylphosphine)palladium(II) chloride. The amount of the transition metal compound in the reaction can be changed as long as the reaction can proceed, and is usually 0.01 to 0.1 mole per mole of the compound of the general formula (19).

The amount of the borane compound of the general formula (20) in the reaction is usually 1 to 2 moles per mole of the compound of the general formula (19).

Examples of the base include carbonates such as potassium carbonate, and alkali metal hydroxides such as sodium hydroxide and potassium hydroxide.

The reaction temperature of the reaction is usually in the range of 0 to 150° C. The reaction time is usually in the range of 0.1 to 96 hours.

By subjecting the reaction mixture after completion of the reaction to conventional workup such as organic solvent extraction and concentration, the compound of the general formula (19-1) can be isolated. The isolated compound of the general formula (19-1) may be further purified by chromatography or the like.

Process (H-2)

The compound of the general formula (19-2) can be produced by reacting the compound of the general formula (19-1) with palladium carbon under a hydrogen atmosphere.

The reaction is usually performed in a solvent. Examples of the solvent include water; ethers such as 1,4-dioxane, diethyl ether, tetrahydrofuran and tert-butyl=methyl=ether; hydrocarbons such as toluene, benzene and xylene; nitriles such as acetonitrile; alcohols such as methanol and ethanol; esters such as ethyl acetate; and a mixture thereof.

The amount of palladium carbon in the reaction is usually 0.01 to 0.1 mole per mole of the compound of the general formula (19-1).

A pressure of hydrogen in the reaction is in the range of normal pressure to 10 atm.

The reaction temperature of the reaction is usually in the range of 0 to 150° C. The reaction time is usually in the range of 0.1 to 96 hours.

By subjecting the reaction mixture after completion of the reaction to conventional workup such as celite filtration, organic solvent extraction and concentration, the compound of the general formula (19-2) can be isolated. The isolated compound of the general formula (19-2) may be further purified by chromatography or the like.

The compound of the general formula (II) is the known compound, or can be produced from the known compound according to the known method (e.g. Journal of American Chemical Society, 1970, 5916-5921, Journal of Medicinal Chemistry, 1989, 32, 493-503 or Journal of Fluorine Chemistry, 2000, 106, 99-102).

The compound of the general formula (13) is the known compound, or can be produced from the known compound according to the known method (e.g. Journal of the American Chemical Society, 1952, 74, 1387-1390).

The compounds of the general formulas (14), (17-7) and (18-2), as well as perfluoroalkyltrimethylsilane are the known compounds, or can be produced from the known compounds according to the known method (e.g. Tetrahedron Letters, 2001, 42, 3267-3269).

The compound of the general formula (20) is the known compound, or can be produced from the known compound according to the known method (e.g. Tetrahedron Letters, 2001, 42, 4083-4085 or Chemistry Letters, 2004, 33, 1206-1207).

Then, specific examples of the present compounds will be shown below.

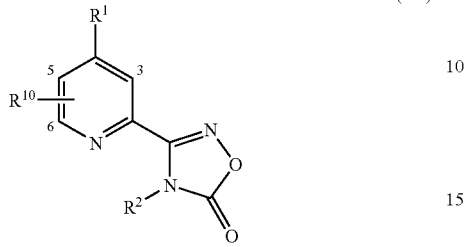

(1-a)

The compounds of the general formula (1-a) wherein $R^1$ is a trifluoromethyl group, $R^2$ is a hydrogen atom, and $R^{10}$ is any group shown in the following Table 1:

TABLE 1

| H | 3-F | 3-Cl | 3-Br |
| --- | --- | --- | --- |
| 3-CH$_3$ | 3-CH$_2$CH$_3$ | 3-CH(CH$_3$)$_2$ | 3-CH(CH$_3$)CH$_2$CH$_3$ |
| 3-OCH$_3$ | 3-OCH$_2$CH$_3$ | 3-OCH(CH$_3$)$_2$ | 3-OCH(CH$_3$)CH$_2$CH$_3$ |
| 3-OCH$_2$F$_3$ | 3-OCF$_3$ | 3-cyclopropyl | 3-cyclobutyl |
| 3-cyclopentyl | 3-CF$_3$ | 3-CF$_2$CF$_3$ | 3-CF(CF$_3$)$_2$ |
| 3-OCH(CH$_3$)CF$_3$ | 5-F | 5-Cl | 5-Br |
| 5-CH$_3$ | 5-CH$_2$CH$_3$ | 5-CH(CH$_3$)$_2$ | 5-CH(CH$_3$)CH$_2$CH$_3$ |
| 5-OCH$_3$ | 5-OCH$_2$CH$_3$ | 5-OCH(CH$_3$)$_2$ | 5-OCH(CH$_3$)CH$_2$CH$_3$ |
| 5-OCH$_2$CF$_3$ | 5-OCF$_3$ | 5-OCH(CH$_3$)CF$_3$ | 5-CF$_3$ |
| 5-CF$_2$CF$_3$ | 5-CF(CF$_3$)$_2$ | 5-cyclopropyl | 5-cyclobutyl |
| 6-F | 6-I | 6-Cl | 6-Br |
| 6-CH$_3$ | 6-CH$_2$CH$_3$ | 6-CH(CH$_3$)$_2$ | 6-CH(CH$_3$)CH$_2$CH$_3$ |
| 6-OCH$_3$ | 6-OCH$_2$CH$_3$ | 6-OCH(CH$_3$)$_2$ | 6-OCH(CH$_3$)CH$_2$CH$_3$ |
| 6-OCH$_2$CF$_3$ | 6-OCF$_3$ | 6-OCF$_2$CF$_3$ | 6-OCH(CH$_3$)CF$_3$ |
| 6-CF$_3$ | 6-CF$_2$CF$_3$ | 6-CF(CF$_3$)$_2$ | 6-cyclopropyl |
| 6-cyclobutyl | 6-cyclopentyl | 6-(1-CH$_3$-cyclopropyl) | 6-cyclopropyloxy |
| 6-cyclobutyloxy | | | |

The compounds of the general formula (1-a) wherein $R^1$ is a pentafluoroethyl group, $R^2$ is a hydrogen atom, and $R^{10}$ is any group shown in the Table 1;

The compounds of the general formula (1-a) wherein $R^1$ is a 2,2,2-trifluoroethoxy group, $R^2$ is a hydrogen atom, and $R^{10}$ is any group shown in the Table 1;

The compounds of the general formula (1-a) wherein $R^1$ is a 2,2,2-trifluoro-1-methylethoxy group, $R^2$ is a hydrogen atom, and $R^{10}$ is any group shown in the Table 1;

The compounds of the general formula (1-a) wherein $R^1$ is a 2,2,2-trifluoro-1-methylethyl group, $R^2$ is a hydrogen atom, and $R^{10}$ is any group shown in the Table 1;

The compounds of the general formula (1-a) wherein $R^1$ is a 2,2,2-trifluororo-1-methoxyethyl group, $R^2$ is a hydrogen atom, and $R^{10}$ is any group shown in the Table 1;

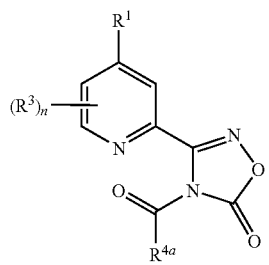

(1-b)

The compounds of the general formula (1-b) wherein $R^1$ is a trifluoromethyl group, n is 0, and $R^{4a}$ is any group shown in the following Table 2;

TABLE 2

| CH$_3$ | CH$_2$CH$_3$ | CH(CH$_3$)$_2$ | C(CH$_3$)$_3$ |
| --- | --- | --- | --- |
| CH$_2$C(CH$_3$)$_3$ | CH(CH$_3$)CH$_2$CH$_3$ | CH$_2$CH(CH$_3$)$_2$ | CH$_2$CH$_2$C(CH$_3$)$_3$ |
| C(CH$_3$)$_2$CH$_2$CH$_3$ | cyclohexyl | 1-CH$_3$cyclohexyl | 2-CH$_3$cyclohexyl |
| 3-CH$_3$cyclohexyl | 4-CH$_3$cyclohexyl | 1-CH$_3$cyclopentyl | cyclopentyl |
| cycloheptyl | cyclopropyl | 1-CH$_3$cyclopropyl | CF$_3$ |
| N(CH$_3$)$_2$ | N(CH$_2$CH$_3$)$_2$ | N(CH$_2$CH$_2$CH$_3$)$_2$ | N(CH$_3$)CH$_2$CH$_3$ |
| N[CH$_2$CH(CH$_3$)$_2$]$_2$ | N(CH$_3$)OCH$_3$ | N(CH$_2$CH=CH$_2$)$_2$ | N(CH$_2$CCH)$_2$ |
| 1-pyrrolidinyl | 2-CH$_3$pyrrolidin-1-yl | piperidino | 2-CH$_3$piperidin-1-yl |
| morpholino | | | |

The compounds of the general formula (1-b) wherein $R^1$ is a pentafluoroethyl group, n is 0, and $R^{4a}$ is any group shown in the Table 2;

The compounds of the general formula (1-b) wherein $R^1$ is a 2,2,2-trifluoroethoxy group, n is 0, and $R^{4a}$ is any group shown in the Table 2;

The compounds of the general formula (1-b) wherein $R^1$ is a 2,2,2-trifluoro-1-methylethoxy group, n is 0, and $R^{4a}$ is any group shown in the Table 2;

The compounds of the general formula (1-b) wherein $R^1$ is a 2,2,2-trifluoro-1-methylethyl group, n is 0, and $R^{4a}$ is any group shown in the Table 2;

The compounds of the general formula (1-b) wherein $R^1$ is a 2,2,2-trifluoro-1-methoxyethyl group, n is 0, and $R^{4a}$ is any group shown in the Table 2;

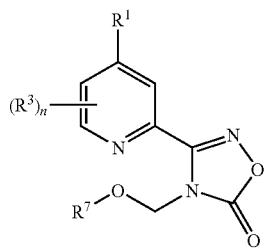

(1-c)

The compounds of the general formula (1-c) wherein $R^1$ is a trifluoromethyl group, n is 0, and $R^7$ is any group shown in the following Table 3;

The compounds of the general formula (1-c) wherein $R^1$ is a 2,2,2-trifluoro-1-methylethyl group, n is 0, and $R^7$ is any group shown in the Table 3;

The compounds of the general formula (1-c) wherein $R^1$ is a 2,2,2-trifluoro-1-methoxyethyl group, n is 0, and $R^7$ is any group shown in Table 3;

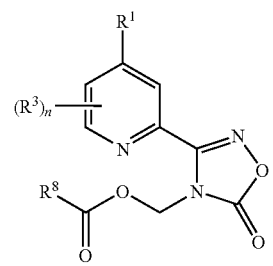

(1-d)

The compounds of the general formula (1-d) wherein $R^1$ is a trifluoromethyl group, n is 0, and $R^8$ is any group shown in the following Table 4;

TABLE 4

| | | | |
|---|---|---|---|
| CH₃ | CH₂CH₃ | CH(CH₃)₂ | C(CH₃)₃ |
| CH₂C(CH₃)₃ | C(CH₃)₂CH₂CH₃ | CF₃ | CF₂CF₃ |
| cyclopropyl | 1-CH₃cyclopropyl | cyclopentyl | 1-CH₃cyclopentyl |
| 1-CH₃cyclohexyl | cyclohexyl | Ph | 2-CH₃-Ph |
| 2-CH₃CH₂-Ph | 2-CH₃O-Ph | 2-F-Ph | 2-Cl-Ph |

TABLE 3

| | | | |
|---|---|---|---|
| CH₃ | CH₂CH₃ | CH(CH₃)₂ | C(CH₃)₃ |
| CH₂C(CH₃)₃ | C(CH₃)₂CH₂CH₃ | CF₃ | CF₂CF₃ |
| cyclopropyl | 1-CH₃cyclopropyl | cyclopentyl | 1-CH₃cyclopentyl |
| 1-CH₃cyclohexyl | cyclohexyl | Ph | 2-CH₃-Ph |
| 2-CH₃CH₂-Ph | 2-CH₃O-Ph | 2-F-Ph | 2-Cl-Ph |
| 2-Br-Ph | 2-CF₃O-Ph | 2-CF₃CH₂O-Ph | 2-CN-Ph |
| 2-NO₂Ph | 2-CF₃-Ph | 2-CF₃CF₂-Ph | 3-F-Ph |
| 3-Cl-Ph | 3-Br-Ph | 3-CH₃-Ph | 3-CH₃CH₂-Ph |
| 3-CH₃O-Ph | 3-CF₃-Ph | 3-CF₃O-Ph | 2-CF₃CH₂O-Ph |
| 3-CN-Ph | 3-NO₂Ph | 4-F-Ph | 4-Cl-Ph |
| 4-CF₃O-Ph | 4-(CH₃)₃C-Ph | 4-CH₃-Ph | 4-CN-Ph |
| 3,5-diF-Ph | 2,4-diF-Ph | 2,5-diFPh | 2,4-diCl-Ph |
| 3,5-diCl-Ph | 2,5-diCl-Ph | 2,6-diCl-Ph | 3,5-diCH₃-Ph |
| 2,5-diCH₃-Ph | 2,4-diCH₃-Ph | 2,6-diCH₃-Ph | 2-Cl-4-CH₃-Ph |
| 2-Cl-4-CN-Ph | 2-CH₃-4-CN-Ph | benzyl | 2-CH₃benzyl |
| 2-CH₃CH₂-benzyl | 2-CH₃O-benzyl | 2-F-benzyl | 2-Cl-benzyl |
| 2-Br-benzyl | 2-CF₃O-benzyl | 2-CF₃CH₂O-benzyl | 2-CN-benzyl |
| 2-NO₂benzyl | 2-CF₃-benzyl | 2-CF₃CF₂-benzyl | 3-F-benzyl |
| 3-Cl-benzyl | 3-Br-benzyl | 3-CH₃-benzyl | 3-CH₃CH₂-benzyl |
| 3-CH₃O-benzyl | 3-CF₃-benzyl | 3-CF₃O-benzyl | 2-CF₃CH₂O-benzyl |
| 3-CN-benzyl | 3-NO₂benzyl | 4-F-benzyl | 4-Cl-benzyl |
| 4-CF₃O-benzyl | 4-(CH₃)₃C-benzyl | 4-CH₃-benzyl | 4-CN-benzyl |
| 3,5-diF-benzyl | 2,4-diF-benzyl | 2,5-diF-benzyl | 2,4-diCl-benzyl |
| 3,5-diCl-benzyl | 2,5-diCl-benzyl | 2,6-diCl-benzyl | 3,5-diCH₃-benzyl |
| 2,5-diCH₃-benzyl | 2,4-diCH₃-benzyl | 2,6-diCH₃-benzyl | 2-Cl-4-CH₃-benzyl |

The compounds of the general formula (1-c) wherein $R^1$ is a pentafluoroethyl group, n is 0, and $R^7$ is any group shown in the Table 3;

The compounds of the general formula (1-c) wherein $R^1$ is a 2,2,2-trifluoroethoxy group, n is 0, and $R^7$ is any group shown in the Table 3;

The compounds of the general formula (1-c) wherein $R^1$ is a 2,2,2-trifluoro-1-methylethoxy group, n is 0, and $R^7$ is any group shown in the Table 3;

TABLE 4-continued

| | | | |
|---|---|---|---|
| 2-Br-Ph | 2-CF₃O-Ph | 2-CF₃CH₂O-Ph | 2-CN-Ph |
| 2-NO₂Ph | 2-CF₃-Ph | 2-CF₃CF₂-Ph | 3-F-Ph |
| 3-Cl-Ph | 3-Br-Ph | 3-CH₃-Ph | 3-CH₃CH₂-Ph |
| 3-CH₃O-Ph | 3-CF₃-Ph | 3-CF₃O-Ph | 2-CF₃CH₂O-Ph |
| 3-CN-Ph | 3-NO₂Ph | 4-F-Ph | 4-Cl-Ph |
| 4-CF₃O-Ph | 4-(CH₃)₃C-Ph | 4-CH₃-Ph | 4-CN-Ph |
| 3,5-diF-Ph | 2,4-diF-Ph | 2,5-diFPh | 2,4-diCl-Ph |
| 3,5-diCl-Ph | 2,5-diCl-Ph | 2,6-diCl-Ph | 3,5-diCH₃-Ph |
| 2,5-diCH₃-Ph | 2,4-diCH₃-Ph | 2,6-diCH₃-Ph | 2-Cl-4-CH₃-Ph |
| 2-Cl-4-CN-Ph | 2-CH₃-4-CN-Ph | 3,4,5-triF-Ph | 2,4,6-triF-Ph |

TABLE 4-continued

| 3,4,5-triCl-Ph | 2,4,6-triCl-Ph | 3,4,5-triCH$_3$-Ph | 2,4,6-triCH$_3$-Ph |
|---|---|---|---|

The compounds of the general formula (1-d) wherein $R^1$ is a pentafluoroethyl group, n is 0, and $R^8$ is any group shown in the Table 4;

The compounds of the general formula (1-d) wherein $R^1$ is a 2,2,2-trifluoroethoxy group, n is 0, and $R^8$ is any group shown in the Table 4;

The compounds of the general formula (1-d) wherein $R^1$ is a 1-methyl-2,2,2-trifluoroethoxy group, n is 0, and $R^8$ is any group represented by the Table 4;

The compounds of the general formula (1-d) wherein $R^1$ is a 2,2,2-trifluoro-1-methylethyl group, n is 0, and $R^8$ is any group shown in the Table 4;

The compounds of the general formula (1-d) wherein $R^1$ is a 2,2,2-trifluoro-1-methoxyethyl group, n is 0, and $R^8$ is any group shown in the Table 4;

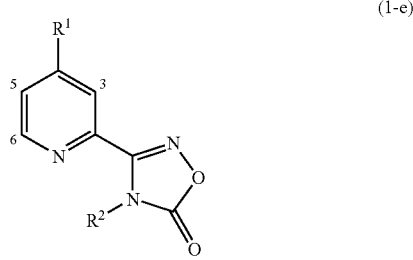

(1-e)

The compounds of the general formula (1-e) wherein $R^2$ is a hydrogen atom, and $R^1$ is any group shown in the following Table 5.

TABLE 5

| | | | |
|---|---|---|---|
| C$_3$F$_7$ | OCF$_3$ | CF(CF$_3$)$_2$ | CH$_2$CF$_3$ |
| CHCF$_2$ | CClCF$_2$ | CBrF$_2$ | OC(CH$_3$)$_2$CF$_3$ |
| OCClF$_2$ | OCH$_2$CF$_2$CF$_3$ | OCH$_2$CCl$_2$CF$_3$ | OCH$_2$ClF2 |
| CH(OH)CF$_3$ | C(OH)$_2$CF$_3$ | C(CH$_3$)(OH)CF$_3$ | C(CH$_3$)(SiMe$_3$)CF$_3$ |
| CF(OCH$_3$)CF$_3$ | CH(OC$_2$H$_5$)CF$_3$ | CH(OC$_2$H$_5$)C$_2$F$_5$ | CH(OC$_2$H$_5$)CF$_3$ |
| C(OH)(CF$_3$)$_2$ | C(OCH$_3$)(CF$_3$)$_2$ | CH(OC$_3$H$_7$)CF$_3$ | CH(OCH$_2$CH=CH)CF$_3$ |
| CH(OCH$_2$CCH)CF$_3$ | CH(OCH$_3$)C$_2$F$_5$ | CH(C$_2$H$_5$)CF$_3$ | CH(C$_2$H$_5$)C$_2$F$_5$ |
| CH(C$_2$H$_5$)CF$_3$ | | | |

The present compound has the excellent controlling effect on a pest.

Examples of the pest on which the present compound has an effect include arthropod such as insect and mite; nemathelminth such as nematode, specifically, the following organisms.

Hemiptera: Delphacidae such as *Laodelphax striatellus*, *Nilaparvata lugens*, and *Sogatella furcifera*, Cicadelloidea such as *Nephotettix cincticeps*, and *Nephotettix virescens*, Aphidoidea such as *Aphis gossypii*, and *Myzus persicae*, Pentatomidae such as *Nesuczara antennata*, *Riptortus clavetus*, *Eysarcoris lewisi*, *Eysarcoris parvus*, *Plautia stali*, *Halyomorpha mista*, *Stenotus rubrovittatus*, and *Trigonotylus ruficornis*, Aleyrodoidae such as *Trialeurodes vaporariorum*, and *Bemisia argentifolii*, Coccoidea such as *Aonidiella aurantii*, *Comstockaspis perniciosa*, *Unaspis citri*, *Ceroplastes rubens*, and *Icerya purchasi*, Tingoidea, Cimicoidea such as *Cimex lectularius*, Psylloidea;

Lepidoptera: Pyraloidea such as *Chilo suppressalis*, *Cnaphalocrocis medinalis*, *Notarcha derogata*, and *Plodia interpunctella*, Noctuoidea such as *Spodoptera litura*, *Pseudaletia separata*, *Trichoplusia*, *Heliothis*, and *Helicoverpa*, Pieridae such as *Pieris rapae*, Tortricoidae such as *Adoxophyes*, *Grapholita molesta*, and *Cydia pomonella*, Copromorphoidea such as *Carposina niponensis*, Lyonetiidae such as *Lyonetia*, Lymantriidae such as *Lymantria*, and *Euproctis*, Yponomeutoidea such as *Plutella xylostella*, Gelechioidea such as *Pectinophora gossypiella*, Arctiidae such as *Hyphantria cunea*, Tineoidea such as *Tinea translucens*, and *Tineola bisselliella*;

Diptera: *Culex* such as *Culex pipiens pallens*, *Culex tritaeniorhynchus*, and *Culex quinquefasciatus*, *Aedes* such as *Aedes aegypti*, and *Aedes albopictus*, *Anopheles* such as *Anopheles sinensis*, *Chironomoidea*, Muscoidea such as *Musca domestica*, and *Muscina stabulans*, Calliphoridae, Sarcophagidae, Fanniidae, Anthomyiidae such as *Delia platura*, and *Delia antiqua*, Agromyzidae such as *Liriomyza trifolii*, Tephritidae Drosophilidae, Phoroidea such as *Megaselia spiracularis*, Psychodidae such as *Clogmia albipunctata*, Simuliidae, Tabanoidea, Stomoxyinae;

Coleoptera: *Diabrotica* such as *Diabrotica virgifera virgifera*, and *Diabrotica undecimpunctata howardi*, Scarabaeoidea such as *Anomala cuprea*, and *Anomala rufocuprea*, Curculionoidea such as *Sitophilus zeamais*, *Lissorhoptrus oryzophilus*, and *Callosobruchuys chienensis*, Tenebrionoidea such as *Tenebrio molitor*, and *Tribolium castaneum*, Chrysomelidae such as *Oulema oryzae*, *Aulacophora femoralis*, *Phyllotreta striolata*, and *Leptinotarsa decemlineata*, Dermestidae such as *Dermestes maculates*, Anobiidae, *Epilachna* such as *Epilachna vigintioctopunctata*, Lyctinae, Bostrichoidea, Ptimidae, Cerambycidae, *Paederus fuscipes*;

Blattodea: *Blattella germanica*, *Periplaneta fuliginosa*, *Periplaneta americana*, *Periplaneta brunnea*, *Blatta orientalis*;

Thysanoptera: *Thrips palmi*, *Thrips tabaci*, *Frankliniella occidentalis*, *Frankliniella intonsa*;

Hymenoptera: Formicidae such as *Monomorium pharaosis*, *Formica fusca japonica*, *Ochetellus glaber*, *Pristomyrmex pungens*, and *Pheidole noda*, Vespidae, Bethylidae, Tenthredinoidea such as *Athalia japonica*;

Orthopetera: Gryllotalpidae, Acrididae, Gryllidae;

Siphonaptera: *Ctenocephalides felis*, *Ctenocephalides canis*, *Pulex irritans*, *Xenopsylla cheopis*;

Phthiraptera: *Pediculus humanus corporis*, *Phthirus pubis*, *Haematopinus eurysternus*, *Dalmalinia ovis*, *Haematopinus suis*;

Isoptera: Subterranean termite such as *Reticulitermes speratus*, *Coptotermes formosanus*, *Reticulitermes flavipes*, *Reticulitermes hesperus*, *Reticulitermes virginicus*, *Reticulitermes tibialis*, and *Heterotermes aureus*, Drywood termite such as *Incisitermes minor*, Dampwood termite such as *Zootermopsis nevadensis*;

Acari: Tetranychidae such as *Tetranychus urticae*, *Tetranychus kanzawai*, *Panonychus citri*, *Panonychus ulmi*, and *Oligonychus*, Eriophyidae such as *Aculops lycopers*, *Aculops*

*pelekassi*, and *Aculus schlechtendali*, Tarsonemidae such as *Polyphagotarsonemus latus*, Tenuipalpidae, Tuckerellidae, Ixodoidea such as *Haemaphysalis longicornis, Haemaphysalis flava, Dermacentor variabilis, Haemaphysalis flava, Dermacentor taiwanicus, Ixodes ovatus, Ixodes persulcatus, Ixodes scapularis, Boophilus microplus, Amblyomma americanum*, and *Rhipicephalus sanguineus*, Acaridae such as *Tyrophagus putrescentiae*, Pyroglyphidae such as *Dermatophagoides farinae*, and *Dermatophagoides ptrenyssnus*, Cheyletidae such as *Cheyletus eruditus, Cheyletus malaccensis*, and *Cheyletus moorei, Ornithonyssus bacoti, Ornithonyssus sylvairum*, Dermanyssidae such as *Dermanyssus gallinae*, Trombiculidae such as *Leptotrombidium akamushi*;

Araneae: *Chiracanthium japonicum, Latrodectus hasseltii*;

Chilopoda: *Thereuonema hilgendorfi, Scolopendra subspinipes*;

Diplopoda: *Oxidus gracilis, Nedyopus tambanus*;

Isopoda: *Armadillidium vulgare*;

Gastropoda: *Limax marginatus, Limax flavus*; and

Nematoda: *Pratylenchus coffeae, Pratylenchus fallax, Heterodera glycines, Globodera rostochiensis, Meloidogyne hapla, Meloidogyne incognita*.

A pesticidal composition containing the present compound as an active ingredient is also one of the present inventions.

The pesticidal composition of the present invention may be the present compound itself, or may be an agent formulated into preparations such as oil solutions, emulsifiable concentrates, flowables, granules, dusts, bait poisons, microcapsules and resin preparations.

The pesticidal composition of the present invention, when formulated into preparations, usually contains the present compound in the amount of 0.01 to 95%.

The present compound can be formulated into preparations, for example, by mixing a solid carrier, a liquid carrier, a gaseous carrier and/or a feed and, if necessary, adding a surfactant and other adjuvant.

Examples of the solid carrier include fine powders or particles of clays (kaolin clay, diatomaceous earth, synthetic hydrous silicon oxide, bentonite, fubasami clay, acid clay, etc.), talcs, ceramics, other inorganic minerals (sericite, quartz, sulfur, active carbon, calcium carbonate, hydrated silica, etc.), chemical fertilizers (ammonium sulfate, ammonium phosphate, ammonium nitrate, urea, ammonium chloride, etc.), and examples of the liquid carrier include water, alcohols (methanol, ethanol etc.), ketones (acetone, methyl ethyl ketone, etc.), aromatic hydrocarbons (benzene, toluene, xylene, ethylbenzene, methylnaphthalene, etc.), aliphatic hydrocarbons (hexane, cyclohexane, kerosene, gas oil, etc.), esters (ethyl acetate, butyl acetate, etc.), nitriles (acetonitrile, isobutyronitrile, etc.), ethers (diisopropyl ether, dioxane, etc.), acid amides (N,N-dimethylformamide, N,N-dimethylacetamide, etc.), halogenated hydrocarbons (dichloromethane, trichloroethane, carbon tetrachloride, etc.), dimethyl sulfoxide and vegetable oils (soybean oil, cotton seed oil, etc.).

Examples of the gaseous carrier include fluorocarbon, butane gas, LPG (liquefied petroleum gas), dimethyl ether and carbonic acid gas.

Examples of the surfactant include alkyl sulfate ester salts, alkyl sulfonate, alkylaryl sulfonate, allyl=aryl=ethers and polyoxyethylene adducts thereof, polyethylene glycol ethers, polyhydric alcohol esters, and sugar alcohol derivatives.

Examples of other adjuvants for preparations include binders, dispersants and stabilizers, for example, casein, keratin, polysaccharides (starch powder, gum arabic, cellulose derivative, alginic acid, etc.), lignin derivatives, bentonite, sugars, synthetic water-soluble polymers (polyvinyl alcohol, polyvinylpyrrolidone, polyacrylic acids, etc.), PAP (acidic isopropyl phosphate), BHT (2,6-di-tertiarybutyl-4-methylphenol), BHA (mixture of 2-tertiarybutyl-4-methoxyphenol and 3-tertiarybutyl-4-methoxyphenol), vegetable oils, mineral oils, and fatty acid or ester thereof.

Examples of a base material of the bait poison include bait components such as cereal powders, vegetable oils, sugars and crystalline cellulose, antioxidants such as dibutylhydroxytoluene and nordihydroguaiuretic acid, preservatives such as dehydroacetic acid, agents for preventing erroneous eating of children or pets such as pepper powder, pest attractive perfumes such as cheese perfumes, onion perfumes and peanut oil.

The pesticidal composition of the present invention can be used together with or in combination with other insecticides, nematicides, miticides, fungicides, herbicides, plant growth regulating substances, plant hormones, drug disaster relieving agents, synergist, fertilizers, soil improving agents, feeds for animal.

Examples of the Insecticides Include:

(1) Organic Phosphorus Compounds acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion;

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur: PHC, XMC, thiodicarb, xylylcarb;

(3) Synthetic Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, 2,3,5,6-tetrafluoro-4-(methoxymethyl)benzyl (EZ)-(1RS,3RS; 1RS,3SR)-2,2-dimethyl-3-prop-1-enylcyclopropanecarboxylate, 2,3,5,6-tetrafluoro-4-methylbenzyl (EZ)-(1RS,3RS; 1RS,3SR)-2,2-dimethyl-3-prop-1-enylcyclopropanecarboxylate, 2,3,5,6-tetrafluoro-4-(methoxymethyl)benzyl (1RS,3RS; 1R,3SR)-2,2-dimethyl-3-(2-methyl-1-propenyl) cyclopropanecarboxylate:

(4) Nereistoxin Compounds cartap, bensultap, thiocyclam, monosultap, bisultap;

(5) Neonicotinoid Compounds imidacloprid, nitenpyram, acetamiprid, thiamethoxam, thiacloprid, dinotefuran, clothianidin;

(6) Benzoylurea Compounds chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron;

(7) Phenylpyrazole Compounds acetoprole, ethiprole, fipronil, vaniliprole, pyriprole, pyrafluprole;

(8) Bt Toxin Insecticides

*Bacillus thuringiensis*-derived alive spores and produced crystalline toxins, as well as mixture thereof;

(9) Hydrazine Compounds chromafenozide, halofenozide, methoxyfenozide, tebufenozide;

(10) Organic Chlorine Compounds aldrin, dieldrin, dienochlor, endosulfan, methoxychlor;

(11) Natural Insecticides machine oil, and nicotine-sulfate;

(12) Other Insecticides avermectin-B, bromopropylate, buprofezin, chlorphenapyr, cyromazine, D-D (1,3-Dichloropropene), emamectin-benzoate, fenazaquin, flupyrazofos, hydroprene, indoxacarb, metoxadiazone, milbemycin-A, pymetrozine, pyridalyl, pyriproxyfen, spinosad, sulfluramid, tolfenpyrad, triazamate, flubendiamide, lepimectin, cyflumetofen, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, nidinotefuran, potassium oleate, protrifenbute, spiromesifen, sulfur, metaflumizone, spirotetramat, pyrifluquinazon, chlorantraniliprole.

Examples of miticides (miticidal active ingredients) include acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, pyrimidifen, tebufenpyrad, tetradifon, spirodiclofen, amidoflumet, cyenopyrafen.

Examples of nematicides (nematicidal active ingredients) include DCIP, fosthiazate, levamisol, methylsothiocyanate, morantel tartarate.

Examples of fungicides include acibenzolar-S-methyl, amobam, ampropylfos, anilazine, azoxystrobin, benalaxyl, benodanil, benomyl, benthiavalicarb, benthiazole, bethoxazin, bitertanol, blasticidin-S, Bordeaux mixture, boscalid, bromuconazole, buthiobate, calcium hypochlorite, calcium polysulfide, captan, carbendazol, carboxin, carpropamid, chlobenthiazone, chloroneb, chloropicrin, chlorothalonil: TPN, chlorthiophos, cinnamaldehyde, clozylacon, CAN (2,6-Dichloro-4-nitroaniline), copper hydroxide, copper sulfate, cyazofamid, cyfluphenamid, cymoxanil, cyproconazole, cyprodinil, cyprofuram, dazomet, debacarb, dichlofluanid, D-D (1,3-Dichloropropene), diclocymet, diclomezine, diethofencarb, difenoconazole, diflumetorim, dimefluazole, dimethirimol, dimethomorph, diniconazole-M, dinocap, edifenphos, epoxiconazole, nickel dimethyldutguicarbanate, etaconazole, ethaboxam, ethirimol, etridiazole, famoxadone, fenamidone, fenarimol, fenbuconazole, Fendazosulam, fenhexamid, fenoxanil, fenpiclonil, fenpropidin, fenpropimorph, fentiazon, fentin hydroxide, ferimzone, fluazinam, fludioxonil, flumetover, flumorph, fluoroimide, fluotrimazole, fluoxastrobin, fluquinconazole, flusilazole, flusulfamide, flutolanil, flutriafol, fosetyl-Al, fthalide, fuberidazole, furalaxyl, furametpyr, furcarbanil, furconazole-cis, hexaconazole, hymexazol, IBP, imazalil, imibenconazole, iminoctadine-albesilate, iminoctadine-triacetate, iodocarb, ipconazole, iprodione, iprovalicarb, isoprothiolane, kasugamycin, kresoxim-methyl, mancozeb, maneb, mepanipyrim, mepronil, metalaxyl, metalaxyl-M, metam-sodium, methasulfocarb, methyl bromide, metconazole, methfuroxam, metominostrobin, metrafenone, metsulfovax, mildiomycin, milneb, myclobutanil, myclozolin, nabam, orysastrobin, ofurace, oxadixyl, oxolinic acid, oxpoconazole, oxycarboxin, oxytetracycline, pefurazoate, penconazole, pencycuron, picoxystrobin, polycarbamate, polyoxin, potassium hydrogen carbonate, probenazole, prochloraz, procymidone, propamocarb-hydrochloride, propiconaole, propineb, proquinazid, prothiocarb, prothioconazole, pyracarbolid, pyraclostrobin, pyrazophos, pyributicarb, pyrifenox, pyrimethanil, pyroquilon, quinoxyfen, quintozene: PCNB, silthiopham, simeconazole, sipconazole, sodium bibarbonate, sodium hypochlorite, spiroxamine, SSF-129((E)-2[2-(2, 5-dimethylphenoxymethyl)phenyl]-2-methoxyimino-N-methylacetamide), streptomycin, sulfur, tebuconazole, tecloftalam, tetraconazole, thiabendazole, thiadinil, thiram: TMTD, thifluzamide, thiophanate-methyl, tolclofos-methyl, TPN, triadimefon, triadimenol, triazoxide, triclamide, tricyclazole, tridemorph, triflumizole, trifloxystrobin, triforine, triticonazole, validamycin, vinclozolin, viniconazole, zineb, ziram, and zoxamide.

Examples of herbicides, plant hormones, and plant growth regulating substances include abscisic acid, acetochlor, acifluorfen-sodium, alachlor, alloxydim, ametryn, amicarbazone, amidosulfuron, aminoethoxyvinylglycine, aminopyralid, AC94, 377, amiprofos-methyl, ancymidol, asulam, atrazine, aviglycine, azimsulfuron, beflubutamid, benfluralin, benfuresate, bensulfuron-methyl, bensulide:SAP, bentazone, benthiocarb, benzamizole, benzfendizone, benzobicyclon, benzofenap, benzyl adenine, benzylaminopurine, bialaphos, bifenox, brassinolide, bromacil, bromobutide, butachlor, butafenacil, butamifos, butylate, cafenstrole, calcium carbonate, calcium peroxide, carbaryl, chlomethoxynil, chloridazon, chlorimuron-ethyl, chlorphthalim, chlorpropham, chlorsulfuron, chlorthal-dimethyl, chlorthiamid: DCBN, choline chloride, cinidon-ethyl, cinmethylin, cinosulfuron, clethodim, clomeprop, cloxyfonac-sodium, chlormequat chloride, 4-CPA (4-chlorophenoxyacetic acid, cliprop, clofencet, cumyluron, cyanazine, cyclanilide, cyclosulfamron, cyhalofop-butyl, 2,4-dichlorophenoxyacetic acid salts, dichlorprop: 2,4-DP, daimuron, dalapon: DPA, dimethenamid-P, daminozide, dazomet, n-decyl alcohol, dicamba-sodium: MDBA, dichlobenil: DBN, diflufenican, dikegulac, dimepiperate, dimethametryn, dimethenamid, diquat, dithiopyr, diuron, endothal, epocholeone, esprocarb, ethephon, ethidimuron, ethoxysulfuron, ethychlozate, etobenzanid, fenarimol, fenoxaprop-ethyl, fentrazamide, flazasulfuron, florasulam, fluazifop-butyl, fluazolate, flucarbazone, flufenacet, flufenpyr, flumetralin, flumioxazin, flupropanate-sodium, flupyrsulfuron-methyl-sodium, flurprimidol, fluthiacet-methyl, foramsulfuron, forchlorfenuron, fonnesafen, gibberellin, glufosinate, glyphosate, halosulfuron-methyl, hexazinone, imazamox, imazapic, imazapyr, imazaquin, imazosulfuron, inabenfide, indole acetic acid: IAA, indole butyric acid, iodosulfuron, ioxynil-octanoate, isouron, isoxachlortole, isoxadifen, karbutilate, lactofen, lenacil, linuron, LGC-42153, maleic hydrazide, mecoprop: MCPP, 2-Methyl-4-chlorophenoxyacetic acid salts, MCPA-thioethyl, MCPB (2-Methyl-4-chlorophenoxybutanoic acid ethyl ester), mefenacet, mefluidide, mepiquat, mesosulfuron, mesotrione, methyl daimuron, metamifop, metolachlor, metribuzin, metsulfuron-methyl, molinate, naphthylacetic acid, NAD (1-naphthaleneacetamide), naproanilide, napropamide, n-decyl alcohol, nicosulfuron, n-phenylphthalamic acid, orbencarb, oxadiazon, oxaziclomefone, oxine-sulfate, paclobutrazol, paraquat, pelargonic acid, pendimethalin, penoxsulam, pentoxazone, pethoxamide, phenmedipham, picloram, picolinafen, piperonyl butoxide, piperophos, pretilachlor, primisulfuron-methyl, procarbazone, prodiamine, profluazol, profoxydim, prohexadione-calcium, prohydrojasmon, prometryn, propanil, propoxycarbazone, propyzamide, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac, quiclorac, quinoclamine, quizalofop-ethyl, rimsulfuron, sethoxydim, siduron, simazine, simetryn, sodium chlorate, sulfosulfuron, swep: MCC, tebuthiuron, tepraloxydim, terbacil, terbucarb: MBPMC, thenylchlor, thiazafluoron, thidiazuron, thifensulfuron-methyl, triaziflam, tribufos, triclopyr, tridiphane, trifloxysulfuron, trifluralin, trinexapac-ethyl, tritosulfuron, uniconazole-P, vemolate: PPTC.

Examples of synergists include piperonyl butoxide, sesamex, N-(2-ethylhexyl)-8,9,10-trinorborn-5-ene-2,3-dicarboxylmide (MGK-264), WARF-antiresistant, diethyl maleate etc.

Examples of drug disaster relieving agents include benoxacor, cloquintocet-mexyl, cyometrinil, daimuron, dichlormid, fenchlorazole-ethyl, fenclorim, flurazole, fluxofenim, furilazole, mefenpyr-diethyl, MG191, naphthalic anhydride, oxabetrinil.

A method of controlling a pest including applying an effective amount of the present compound to the pest or a place where the pest inhabits is also one of the present inventions.

The method of controlling a pest of the present invention may comprise applying the present compound as it is or the pesticidal composition as the present compound to the pest or a place where the pest inhabits.

Examples of the place where a pest inhabits in the present invention include cropland such as field of rice, cultivated land, orchard, non-cropland such as forest for agriculture, land for construction, garden, and house.

In the controlling method of the present invention, the pesticidal composition of the present invention can be applied by known methods.

Examples of the method of application include spray treatment, soil treatment, seed treatment, and submerged treatment.

The spray treatment is generally a method of treatment for controlling pests by treating plant surface or pest themselves with an active ingredient (the present compound in the present invention), for example, foliage application, spraying to tree trunk.

The soil treatment is generally a method of treatment for protecting crops from damages by pests, which method comprises adding an active ingredient to soil or irrigation solution for cultivation and penetrating the ingredient from the root of the target plant into the inside of that via the soil or irrigation solution. Specific examples of the soil treatment include a planting hole treatment (planting hole spraying, soil-incorporation after planting hole treatment), a plant foot treatment (plant foot spraying, plant foot soil-incorporation, plant foot irrigation, plant foot treatment at later half of raising seeding period), planting furrow treatment (planting furrow spraying, planting furrow soil-incorporation), planting row treatment (planting row spraying, planting raw soil-incorporation, planting row spraying at growing period), planting row treatment at sowing (planting row spraying at sowing, planting row soil-incorporation at sowing), overall treatment (overall spraying, overall soil-incorporation), other spray treatment (foliar granule spraying at growing period, spraying under tree crown or around main stem, soil surface spraying, soil surface incorporation, sowing hole spraying, spraying on the ribbing ground, inter-plant spraying), other irrigation treatment (irrigation into soil, irrigation during raising seedling, injection treatment of pesticide solution, irrigation on plant foot, pesticide drip irrigation, chemigation), nursery box treatment (nursery box surface spraying, nursery box irrigation), nursery tray treatment (nursery tray spraying, nursery tray irrigation), nursery bed treatment (nursery bed spraying, nursery bed irrigation, nursery bed spraying for paddy field, immersion of nursery plant), seed bed soil-incorporation treatment (seed bed soil-incorporation, seed bed soil-incorporation before sowing), other treatments (growing media incorporation, plowing, surface soil-incorporation, soil incorporation into rain dropping, planting spot treatment, flower cluster granule spraying, paste fertilizer mixing).

The seed treatment is generally a treatment method of controlling a pest by giving an active ingredient directly to a seed, a seed tuber or a bulb of a crop to be protected, or to a near place. Examples of the seed treatment include blowing treatment, smearing treatment, dipping treatment, impregnating treatment, coating treatment, film coating treatment, and pellet coating treatment.

The submerged treatment is generally a treatment method of protecting the plant from a damage by pests, which method comprises adding an active ingredient to water culture medium and penetrating the ingredient from the root of the target plant into the inside of that via the water culture medium. Examples of the water culture medium treatment include water culture medium kneading, and water culture medium mixing.

The pesticidal composition of the present invention can be further used in foliage treatment, or treatment of seedbed before planting of seedling of a prop, or a planting hole or a plant foot at planting. The pesticidal composition may be used in treating a soil of a cultivated land for the purpose of controlling a pest which inhabits in the soil. The pesticidal composition processed into a sheet or string of resin preparation can be also used for a method comprising winding it on a crop, a method comprising tacking across a vicinity of a crop, or a method comprising spreading it on a soil surface of a plant foot.

In the application method, the application amount of the present compound can be generally changed depending on an application term, an application place, an application method or the like.

When the present compound is used for agriculture and forestry, the application amount is usually 0.1 to 10000 g in terms of the amount of the present compound per 1000 $m^2$. In case where the present compound is used for agriculture and forestry, the present compounds formulated into preparations of emulsifiable concentrates, wettable powders, flowables or microcapsules are sprayed after diluting it with water usually by 10 to 1000 ppm, while the present compounds formulated into preparations of granules or dusts are applied as they are.

In case where the present compound is used in controlling a pest inhabiting in a house (e.g. fly, mosquito, cockroach), its application amount is usually 0.01 to 1000 mg per 1 $m^2$ treatment area when a plane is treated, and is usually 0.01 to 500 mg per 1 $m^3$ treatment area when a space is treated. In case where the present compound is used in controlling a pest inhabiting in a house, the present compounds formulated into preparations of emulsifiable concentrates, wettable powders or flowables are sprayed after diluting it with water usually by 0.1 to 1000 ppm, while the present compounds formulated into preparations of oil solutions, aerosols, smoking agents or bait poisons are applied as they are.

The present compound can be further used as an insecticide for cropland or non-cropland such as cultivated land, field of rice, lawn and orchard. For example, the present compound can control pests of cropland in which the following "crops" and the like are cultivated, without giving drug disaster to the crops or the like.

Agricultural crops; corn, rice, wheat, barley, rye, oat, sorghum, cotton, soybean, peanut, buckwheat, sugar beet, rapeseed, sunflower, sugar cane, tobacco, etc.;

Vegetables; Solanum vegetables (eggplant, tomato, green pepper, red pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, Chinese mustard, broccoli, cauliflower, etc.), Compositae vegetables (burdock, garland chrysanthemum, artichoke, lettuce, etc.), Liliaceae vegetables (Welsh onion, onion, garlic, asparagus), Apiaceae vegetables (carrot, parsley, celery, parsnip, etc.), Chenopodiaceae vegetables (spinach, Swiss chard, etc.), Lamiaceae vegetables (beefsteak plant, mint, basil, etc.), strawberry, sweet potato, Japanese yam, aroid, etc., Flowering plants (rose, carnation, chrysanthemum, showy prairie gentian, gypsophila, gerbera, marigold, salvia, petunia, verbena, tulip, aster, gentian, lily, pansy, cyclamen, orchid, lily of the valley, lavender, stock, ornamental kale, primula, poinsettia, gladiolus, cattleya, daisy, cymbidium, begonia, etc.), Foliage plants, Fruit trees; pome fleshy fruits (apple, pear, Japanese pear, quince, marmelo, etc.), stone fleshy fruits (peach, Japanese plum, nectarine, plum, cherry fruit, apricot, prune etc.), citruses (citrus reticulate, orange, lemon, lime, grapefruit, etc.), nuts (chestnut, walnut, hazel, almond, pistachio, cashew nut, macadamian nut, etc.), berry fruits (blueberry, cranberry, blackberry, raspberry, etc), vine, Japanese persimmon, olive, Japanese medlar, banana, coffee, date palm, coconut palm, etc., Trees other than fruit trees; tea, mulberry, flowering trees and shrubs, street trees (Japanese ash, birch, dogwood, eucalyptus, gingko, lilac, maple, oak, poplar, cercis, liquidambar, plane tree, zelkova, Japanese arborvitae, fir tree, hemlock fir, juniper, pine, spruce, Japanese yew), etc., Biofuel crops (fuel plants); bastard saffron, pellavatankio, switchgrass, tung tree, tung tree (*Jatropha curcas*), O. malayanus, lady's-laces, giant reed, ambari, cassava, willow, eucalyptus, alga, etc.

The "crop" also includes crops to which resistance to a HPPD inhibitor such as isoxaflutole, ALS inhibitor such as imazethapyr and thifensulfuron-methyl, EPSP synthase inhibitor, glutamine synthase inhibitor, herbicide such as bromoxynil is imparted by a classical breeding method or genetic recombination technique.

Examples of the "crop" to which resistance is imparted by the classical breeding method include Clearfield (registered trademark) canola resistant to an imidazolinone herbicide such as imazethapyr, STS soybean resistant to a sulfonylurea ALS inhibition-type herbicide such as thifensulfuron-methyl. Similarly, there is soybean resistant to a sulfonylurea ALS inhibition-type herbicide such as thifensulfuron-methyl by a classical breeding method, and this has come onto the market as a trade name of STS soybean. SR corn is known as an example of crops to which resistance to an acetyl CoA carboxylase inhibitor such as trioneoxime, and an aryloxyphenoxypropionic acid herbicide is imparted by the classical breeding method. A crop to which resistance to an acetyl CoA carboxylase inhibitor is imparted is described in Proc. Natl. Acad. Sci. USA, vol. 87, pp. 7175-7179 (1990). Mutant acetyl CoA carboxylase resistant to an acetyl CoA carboxylase inhibitor is reported in Weed Science, vol. 53, pp. 728-746 (2005). By introducing such a mutant acetyl CoA carboxylase gene into a crop by the genetic recombination technique, or introducing mutation involved in resistance impartation into crop acetyl CoA carboxylase, a crop resistant to an acetyl CoA carboxylase inhibitor can be produced. By introducing a nucleotide substitution mutation-introduced nucleic acid, a representative of which is the chimeraplasty technique (Gura T. 1999. Repairing the Genome's Spelling Mistakes. Science 285:316-318) into a crop cell to cause site-specific amino acid substitution mutation in a crop acetyl CoA carboxylase/herbicide target gene, a crop resistant to an acetyl CoA carboxylase inhibitor/herbicide can be produced.

An example of a crop to which resistance is imparted by the genetic recombination technique includes a corn, resistant to glyphosate and glufosinate, and this has come onto the market as a trade name such as RoundupReady (registered trade mark) and LibertyLink (registered trade mark).

The "crop" also includes crops which have become possible to synthesize a selected toxin of genus *Bacillus* by the genetic recombination technique.

Examples of a toxin expressed in such a genetic recombinant plant include insecticidal proteins derived from *Bacillus cereus* and *Bacillus popilliae*; insecticidal protein such as δ-endotoxin such as Cry1Ab, Cry1Ac, Cry1F, Cry1Fa2, Cry2Ab, Cry3A, Cry3Bb1 and Cry9C, VIP1, VIP2, VIP3 and VIP3A derived from *Bacillus thuringiensis*; insecticidal proteins derived from Nematoda; toxins produced by animals such as scorpion toxin, spider toxin, bee toxin and insect-specific nerve toxin; filamentous fungus toxin; plant lectin; agglutinin; protease inhibitors such as trypsin inhibitor, serine protease inhibitor, patatin, cystatin, papain inhibitor etc; ribosome inactivated protein (RIP) such as ricin, corn-RIP, abrin, luffin, saporin and bryodin; steroid metabolism enzymes such as 3-hydroxysteroid oxidase, ecdysteroid-UDP-glycosyltransferase and cholesterol oxidase; ecdysone inhibitor; HMG-COA reductase; ion channel inhibitor such as sodium channel inhibitor and potassium channel inhibitor; juvenile hormone estelase; diuretic hormone receptor; stilbene synthase; bibenzyl synthase; chitinase; glucanase.

A toxin expressed in such a genetic recombinant crop includes hybrid toxins, portion-deficient toxins, and modified toxins of insecticidal proteins such as δ-endotoxin proteins such as Cry1Ab, Cry1Ac, Cry1F, Cry1Fa2, Cry2Ab, Cry3A, Cry3Bb1, Cry9C, VIP1, VIP2, VIP3 and VIP3A. Hybrid toxins are made by a new combination of different domains of these proteins using the recombination technique. As the portion-deficient toxin, Cry1Ab, a portion of amino acid sequence of which is deleted, is known. As the modified toxin, one or a plurality of amino acids of a natural-toxin are substituted.

Examples of these toxins, and recombinant plants which can synthesize these toxins are described in EP-A-0 374 753, WO 93/07278, WO 95/34656, EP-A-0 427 529, EP-A-451 878, WO 03/052073.

Toxins contained in these recombinant plants impart resistance to, particularly, Coleoptera, Dipterous, and Lepidoptera to plants.

Genetic recombinant plants containing one or a plurality of insecticidal pest resistant genes and expressing one or a plurality of toxins are already known, some of which have come onto the market. Examples of these genetic recombinant plants include YieldGard (registered trade mark) (corn expressing Cry1 Ab toxin), YieldGard Rootworm (registered trade mark) (corn expressing Cry3Bb1 toxin), YieldGard Plus (registered trade mark) (corn expressing Cry1Ab and Cry3Bb1 toxins), Herculex I (registered trade mark) (corn expressing phosphinotricine N-acetyltransferase (PAT) for imparting resistance to Cry1Fa2 toxin and glufosinate), NuCOTN33B (registered trade mark) (cotton expressing Cry1Ac toxin), Bollgard I (registered trade mark) (cotton expressing Cry1Ac toxin), Bollgard II (registered trade mark) (cotton expressing Cry1Ac and Cry2Ab toxins), VIPCOT (registered trade mark) (cotton expressing VIP toxin), NewLeaf (registered trade mark) (potato expressing Cry3A toxin), NatureGard (registered trade mark) Agrisure (registered trade mark) GT Advantage (GA21 glyphosate resistant character), Agrisure (registered trade mark) CB Advantage (Bt11 Corn Borer (CB) character), Protecta (registered trade mark).

The "crop" also includes crops to which the ability to produce an anti-pathological substance having the selected activity has been imparted by the genetic recombination technique.

As an example of the anti-pathological substance, PR protein and the like are known (PRPs, EP-A-0 392 225). Such an anti-pathological substance and a genetic recombinant plant producing it are described in EP-A-0 392 225, WO 95/33818, EP-A-0 353 191.

Examples of the anti-pathological substance expressed in such a gene recombinant plant include anti-pathological substances produced by micro organisms such as ion channel inhibitors such as a sodium channel inhibitor, and a calcium channel inhibitor (KP1, KP4 and KP6 toxins, and the like, produced by viruses are known); stilbene synthase; bibenzyl synthase; chitinase; glucanase; PR protein; peptide antibiotics, antibiotics having a heterocyclic ring, protein factors involved in plant disease resistance (described in WO 03/000906).

The "crop" also includes crops in which a useful trait such as oil component or amino acid content is modified by the genetic recombination technique. Examples include VISTIVE (registered trade mark) (low linolen soybean having a reduced linolen content) and high-lysine (high-oil) corn (corn having an increased lysine or oil content).

Stuck varieties of a combination of plural of useful characters such as the aforementioned classical herbicide character or herbicide resistance gene, insecticidal pest resistance gene, anti-pathological substance production gene, and oil stuff component modification and amino acid content enhancing character are also included.

EXAMPLES

The present invention will be described in more detail below by way of Production Examples, Preparation Examples and Test Examples, but the present invention is not limited to these examples.

In Production Examples and Reference Production Examples, $^1$H-NMR show data measured using tetramethylsilane as an internal standard in a deuterated chloroform solvent unless otherwise is indicated, and $^{19}$F-NMR shows data measured using trichlorofluoromethane as an internal standard in a deuterated chloroform solvent unless otherwise is indicated.

Production Example 1

To 1 ml of tetrahydrofuran were added 0.08 g of 4-trifluoromethylpyridine-2-carboxamide=oxime and 0.076 g of 1,1'-carbonyldiimidazole, and the mixture was stirred at room temperature for 2 hours. Thereafter, 0.072 g of 1,8-diazabicyclo[5,4,0]undec-7-ene was added, and the mixture was stirred for 6 hours. To the reaction solution were added water and 10% HCl, the resultant solution was extracted with ethyl acetate three times, and organic layers were combined, dried with anhydrous magnesium sulfate, and concentrated. The residue was subjected to silica gel column chromatography to obtain 0.06 g of 3-(4-trifluoromethylpyridin-2-yl)-1,2,4-oxadiazol-5-one (present compound (2)).

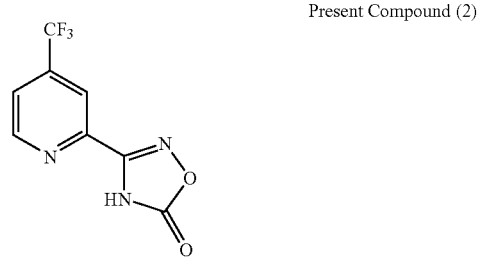

Present Compound (2)

$^1$H-NMR (DMSO-d$_6$): 8.08 (d, 1H), 8.23 (s, 1H), 9.06 (d, 1H), 13.39 (bs, 1H)

Production Example 2

To 1 ml of tetrahydrofuran were added 0.07 g of 6-chloro-4-trifluoromethylpyridine-2-carboxamide=oxime and 0.057 g of 1,1'-carbonyldiimidazole, and the mixture was stirred at room temperature for 3 hours. Thereafter, 0.053 g of 1,8-diazabicyclo[5,4,0]undec-7-ene was added, and the mixture was stirred for 6 hours. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.058 g of 3-(6-chloro-4-trifluoromethylpyridin-2-yl)-1,2,4-oxadiazol-5-one (present compound (1)).

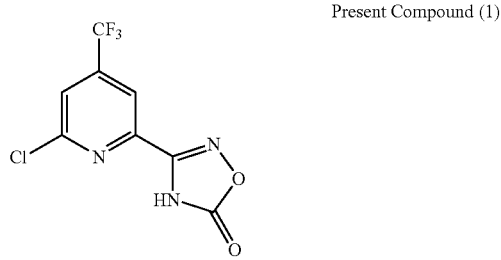

Present Compound (1)

$^1$H-NMR (DMSO-d$_6$): 8.22 (d, 1H), 8.33 (d, 1H)

Production Example 3

To 5 ml of tetrahydrofuran were added 0.6 g of 6-fluoro-4-trifluoromethylpyridine-2-carboxamide=oxime and 0.61 g of 1,1'-carbonyldiimidazole, and the mixture was stirred at room temperature for 2 hours and 30 minutes. Thereafter, 0.57 g of 1,8-diazabicyclo[5,4,0]undec-7-ene was added, and the mixture was stirred for 9 hours. To the reaction solution were added water and 10% HCl, the resultant solution was extracted with ethyl acetate three times, and the organic layers were combinedmm, dried with anhydrous magnesium sulfate, and concentrated. The residue was subjected to silica gel column chromatography to obtain 0.5 g of 3-(6-fluoro-4-trifluoromethylpyridin-2-yl)-1,2,4-oxadiazol-5-one (present compound (49)).

Present Compound (49)

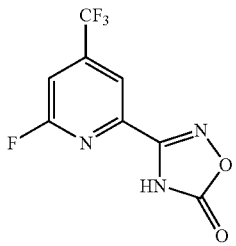

¹H-NMR (DMSO-d₆): 8.09 (d, 1H), 8.20 (d, 1H), 13.42 (bs, 1H)

Production Example 4

To 6.6 ml of tetrahydrofuran were added 0.8 g of 5-chloro-4-trifluoromethylpyridine-2-carboxamide=oxime and 0.76 g of 1,1'-carbonyldiimidazole, and the mixture was stirred at room temperature for 1 hour and 30 minutes. Thereafter, 0.71 g of 1,8-diazabicyclo[5,4,0]undec-7-ene was added, and the mixture was stirred for 3 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.68 g of 3-(5-chloro-4-trifluoromethylpyridin-2-yl)-1,2,4-oxadiazol-5-one (present compound (51)).

Present Compound (51)

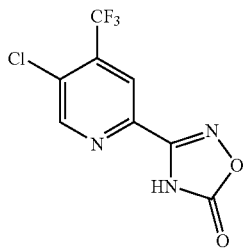

¹H-NMR (DMSO-d₆): 8.26 (s, 1H), 9.16 (s, 1H), 13.48 (bs, 1H)

Production Example 5

To 4 ml of tetrahydrofuran were added 0.4 g of 5-fluoro-4-trifluoromethylpyridine-2-carboxamide=oxime and 0.41 g of 1,1'-carbonyldiimidazole, and the mixture was stirred at room temperature for 2 hours. Thereafter, 0.38 g of 1,8-diazabicyclo[5,4,0]undec-7-ene was added, and the mixture was stirred for 9 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.35 g of 3-(5-fluoro-4-trifluoromethylpyridin-2-yl)-1,2,4-oxadiazol-5-one (present compound (52)).

Present Compound (52)

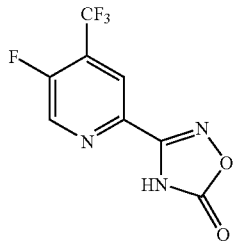

¹H-NMR (DMSO-d₆): 8.28 (d, 1H), 9.15 (s, 1H), 13.40 (bs, 1H)

Production Example 6

To 3 ml of tetrahydrofuran were added 0.3 g of 3-fluoro-4-trifluoromethylpyridine-2-carboxamide=oxime and 0.31 g of 1,1'-carbonyldiimidazole, and the mixture was stirred at room temperature for 2 hours. Thereafter, 0.29 g of 1,8-diazabicyclo[5,4,0]undec-7-ene was added, and the mixture was stirred for 4 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.19 g of 3-(3-fluoro-4-trifluoromethylpyridin-2-yl)-1,2,4-oxadiazol-5-one (present compound (50)).

Present Compound (50)

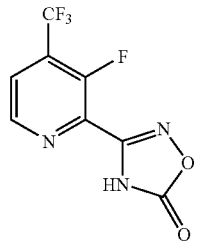

¹H-NMR (DMSO-d₆): 8.15 (t, 1H), 8.86 (d, 1H), 13.33 (bs, 1H)

Production Example 7

To 5 ml of tetrahydrofuran were added 0.6 g of 6-cyclopropyl-4-trifluoromethylpyridine-2-carboxamide=oxime and 0.56 g of 1,1'-carbonyldiimidazole, and the mixture was stirred at room temperature for 2 hours. Thereafter, 0.52 g of 1,8-diazabicyclo[5,4,0]undec-7-ene was added, and the mixture was stirred for 10 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.52 g of 3-(6-cyclopropyl-4-trifluoromethylpyridin-2-yl)-1,2,4-oxadiazol-5-one (present compound (53)).

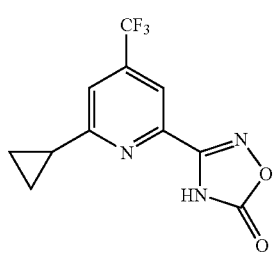

Present Compound (53)

¹H-NMR (DMSO-d₆): 1.06-1.11 (m, 2H), 1.20-1.24 (m, 2H), 2.34-2.41 (m, 1H), 7.90 (d, 1H), 8.02 (d, 2H), 13.10 (bs, 1H)

Production Example 8

To 3 ml of tetrahydrofuran were added 0.74 g of 6-methyl-4-trifluoromethylpyridine-2-carboxamide=oxime and 0.41 g of 1,1'-carbonyldiimidazole, and the mixture was stirred at room temperature for 1 hour and 30 minutes. Thereafter, 0.39 g of 1,8-diazabicyclo[5,4,0]undec-7-ene was added, and the mixture was stirred for 12 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.6 g of 3-(6-methyl-4-trifluoromethylpyridin-2-yl)-1,2,4-oxadiazol-5-one (present compound (54)).

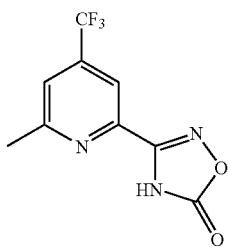

Present Compound (54)

¹H-NMR (DMSO-d₆): 2.69 (s, 3H), 7.97 (s, 1H), 8.02 (s, 1H), 13.24 (bs, 1H)

Production Example 9

Into 3 ml of tetrahydrofuran was suspended 0.06 g of sodium hydride (60% oily), and 0.3 g of 3-(4-trifluoromethylpyridin-2-yl)-1,2,4-oxadiazol-5-one was added at 0° C. The mixture was stirred at room temperature for 10 minutes, 0.22 g of iodomethane and 1 ml of dimethylformamide were added, and the mixture was stirred at 40° C. for 3 hours. Thereafter, the reaction solution was poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.26 g of 4-methyl-3-(4-trifluoromethylpyridin-2-yl)-1,2,4-oxadiazol-5-one (present compound (3)).

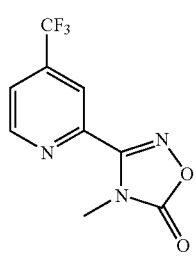

Present Compound (3)

¹H-NMR: 3.69 (s, 3H), 7.73 (d, 1H), 8.29 (s, 1H), 8.95 (d, 1H)

Production Example 10

Into 2 ml of N,N-dimethylformamide was suspended 0.04 g of sodium hydride (60% oily), and 0.2 g of 3-(4-trifluoromethylpyridin-2-yl)-1,2,4-oxadiazol-5-one was added at 0° C. After stirring for 10 minutes, 0.12 g of cyclopropanecarbonyl chloride was added, and the mixture was stirred at 50° C. for 4 hours. Thereafter, the reaction solution was poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.08 g of 4-cyclopropanecarbonyl-3-(4-trifluoromethylpyridin-2-yl)-1,2,4-oxadiazol-5-one (present compound (4)).

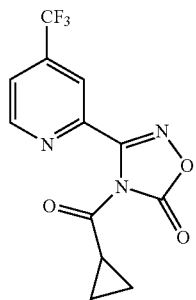

Present Compound (4)

¹H-NMR: 1.27-1.32 (m, 4H), 2.84-2.90 (m, 1H), 7.69 (d, 1H), 7.93 (s, 1H), 8.86 (d, 1H)

Production Example 11

Into 2 ml of N,N-dimethylformamide was suspended 0.04 g of sodium hydride (60% oily), and 0.2 g of 3-(4-trifluoromethylpyridin-2-yl)-1,2,4-oxadiazol-5-one was added at room temperature. After stirring for 10 minutes, 0.22 g of benzyl bromide was added, and the mixture was stirred for 3 hours. Thereafter, the reaction solution was poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.08 g of 4-benzyl-3-(4-trifluoromethylpyridin-2-yl)-1,2,4-oxadiazol-5-one (present compound (5)).

Present Compound (5)

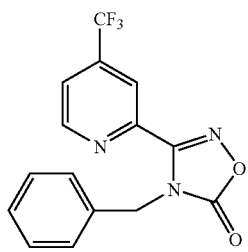

¹H-NMR: 5.44 (s, 2H), 7.25-7.27 (m, 5H), 7.69 (d, 1H), 8.22 (s, 1H), 8.92 (d, 1H)

Production Example 12

Into 2 ml of N,N-dimethylformamide was suspended 0.04 g of sodium hydride (60% oily), and 0.2 g of 3-(4-trifluoromethylpyridin-2-yl)-1,2,4-oxadiazol-5-one was added at room temperature. After stirring for 10 minutes, 0.16 g of bromoacetonitrile was added, and the mixture was stirred for 2 hours. After stirring at 60° C. for 6 hours, the reaction solution was allowed to cool to room temperature, and poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.17 g of 4-cyanomethyl-3-(4-trifluoromethylpyridin-2-yl)-1,2,4-oxadiazol-5-one (present compound (6)).

Present Compound (6)

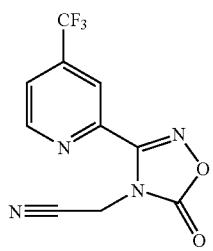

¹H-NMR: 5.20 (s, 2H), 7.80 (d, 1H), 8.36 (s, 1H), 8.99 (d, 1H)

Production Example 13

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.12 g. of chloromethyl=ethyl=ether was added at 0° C., the mixture was stirred at 60° C. for 3 hours, and the reaction solution was allowed to cool to room temperature, and poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.21 g of 4-ethoxymethyl-3-(4-trifluoromethylpyridin-2-yl)-1,2,4-oxadiazol-5-one (present compound (7)).

Present Compound (7)

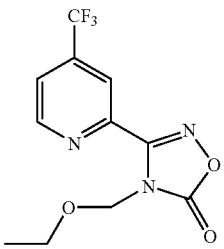

¹H-NMR: 1.15 (t, 3H), 3.63 (q, 2H), 5.68 (s, 2H), 7.74 (d, 1H), 8.29 (s, 1H), 8.96 (d, 1H)

Production Example 14

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.12 g of pivaloyl chloride was added at 0° C., the mixture was stirred at room temperature for 2 hours, and at 60° C. for 3 hours, and the reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.16 g of 4-(2,2-dimethylpropionyl)-3-(4-trifluoromethylpyridin-2-yl)-1,2,4-oxadiazol-5-one (present compound (8)).

Present Compound (8)

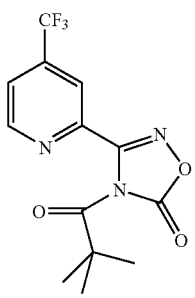

¹H-NMR: 1.45 (s, 9H), 7.70 (d, 1H), 8.22 (d, 1H), 8.79 (d, 1H)

Production Example 15

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.11 g of chloromethyl=methyl=ether was added, the mixture was stirred at room temperature for 1 hour, and at 60° C. for 4 hours, and the reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated.

The residue was subjected to silica gel column chromatography to obtain 0.21 g of 4-(methoxymethyl)-3-(4-trifluoromethylpyridin-2-yl)-1,2,4-oxadiazol-5-one (present compound (9)).

Present Compound (9)

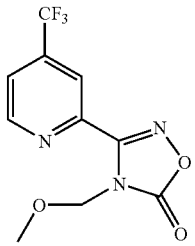

$^1$H-NMR: 3.42 (s, 3H), 5.64 (s, 3H), 7.73 (d, 1H), 8.29 (s, 1H), 8.95 (d, 1H)

Production Example 16

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.2 g of chloromethyl pivalate was added, the mixture was stirred at 60° C. for 7 hours, and the reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.18 g of 4-[(2,2-dimethyl-1-oxopropoxy)methyl]-3-(4-trifluoromethylpyridin-2-yl)-1,2,4-oxadiazol-5-one (present compound (10)).

Present Compound (10)

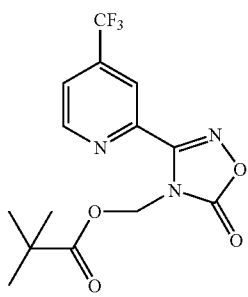

$^1$H-NMR: 1.09 (s, 9H), 6.18 (s, 2H), 7.77 (d, 1H), 8.29 (s, 1H), 8.92 (d, 1H)

Production Example 17

To 1 ml of pyridine were added 0.3 g of 1,8-diazabicyclo[5,4,0]undec-7-ene, and 0.3 g of 3-(4-trifluoromethylpyridin-2-yl)-1,2,4-oxadiazol-5-one, and 0.26 g of 2,2-dimethylbutanoyl chloride was added at room temperature. After stirring for 3 hours, the resultant solution was concentrated, and the residue was subjected to silica gel column chromatography to obtain 0.24 g of 4-(2,2-dimethylbutanoyl)-3-(4-trifluoromethylpyridin-2-yl)-1,2,4-oxadiazol-5-one (present compound (11)).

Present Compound (11)

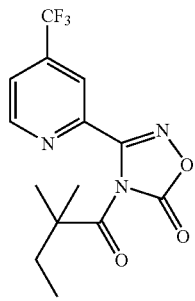

$^1$H-NMR: 1.00 (t, 3H), 1.42 (s, 6H), 1.92 (q, 2H), 7.71 (d, 1H), 8.20 (s, 1H), 8.80 (d, 1H)

Production Example 18

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.2 g of 3,3-dimethylbutanoyl chloride was added, and the mixture was stirred for 6 hours. Thereafter, the reaction solution was poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.17 g of 4-(3,3-dimethylbutanoyl)-3-(4-trifluoromethylpyridin-2-yl)-1,2,4-oxadiazol-5-one (present compound (12)).

Present Compound (12)

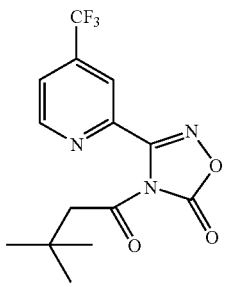

$^1$H-NMR: 1.15 (s, 9H), 3.03 (s, 2H), 7.71 (d, 1H), 7.97 (s, 1H), 8.86 (d, 1H)

Production Example 19

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.14 g of chloromethyl=acetate was added, and the mixture was stirred for 2 hours, and at 60° C. for 3 hours. This mixture was allowed to cool to room temperature, and the reaction solution was poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.13 g of 4-(acetoxy)methyl-3-(4-trifluoromethylpyridin-2-yl)-1,2,4-oxadiazol-5-one (Present compound (13)).

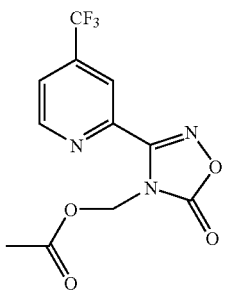

Present Compound (13)

¹H-NMR: 1.09 (s, 9H), 6.18 (s, 2H), 7.77 (d, 1H), 8.29 (s, 1H), 8.92 (d, 1H) Production Example 20

To 1 ml of pyridine were added 0.26 g of 1,8-diazabicyclo[5,4,0]undec-7-ene, and 0.3 g of 3-(4-trifluoromethylpyridin-2-yl)-1,2,4-oxadiazol-5-one, and 0.18 g of N,N-dimethylcarbamoyl chloride was added at room temperature. After stirring for 20 hours, the resultant solution was concentrated, and the residue was subjected to silica gel column chromatography to obtain 0.25 g of 3-(4-trifluoromethylpyridin-2-yl)-N,N-dimethyl-1,2,4-oxadiazol-5-one-4-carboxamide (present compound (14)).

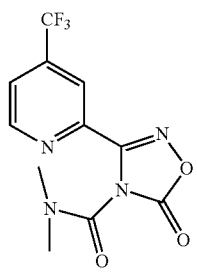

Present Compound (14)

¹H-NMR: 3.17 (s, 3H), 3.21 (s, 3H), 7.70 (d, 1H), 8.20 (s, 1H), 8.85 (d, 1H)

Production Example 21

To 1 ml of pyridine were added 0.3 g of 1,8-diazabicyclo[5,4,0]undec-7-ene, and 0.3 g of 3-(4-trifluoromethylpyridin-2-yl)-1,2,4-oxadiazol-5-one, and 0.26 g of 1-pyrrolidinecarbonyl chloride was added at room temperature. After stirring for 15 hours, the resultant solution was concentrated, and the residue was subjected to silica gel column chromatography to obtain 0.27 g of 4-(1-pyrrolidinecarbonyl)-3-(4-trifluoromethylpyridin-2-yl)-1,2,4-oxadiazol-5-one (present compound (15)).

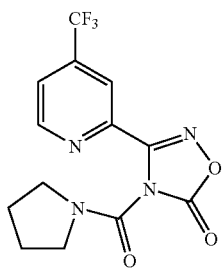

Present Compound (15)

¹H-NMR: 2.04-2.08 (m, 4H), 3.62-3.71 (m, 4H), 7.68 (d, 1H), 8.19 (s, 1H), 8.84 (d, 1H)

Production Example 22

To 1 ml of pyridine were added 0.2 g of 1,8-diazabicyclo[5,4,0]undec-7-ene, and 0.2 g of 3-(4-trifluoromethylpyridin-2-yl)-1,2,4-oxadiazol-5-one, and 0.18 g of N,N-diethylcarbamoyl chloride was added at room temperature. After stirring for 18 hours, the resultant solution was concentrated, and the residue was subjected to silica gel column chromatography to obtain 0.09 g of 3-(4-trifluoromethylpyridin-2-yl)-N,N-diethyl-1,2,4-oxadiazol-5-one-4-carboxamide (present compound (16)).

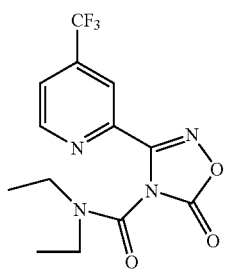

Present Compound (16)

¹H-NMR: 1.30-1.34 (m, 6H), 3.48-3.61 (m, 4H), 7.69 (d, 1H), 8.22 (s, 1H), 8.81 (d, 1H)

Production Example 23

To 1 ml of pyridine were added 0.28 g of 1,8-diazabicyclo[5,4,0]undec-7-ene, and 0.3 g of 3-(4-trifluoromethylpyridin-2-yl)-1,2,4-oxadiazol-5-one, and 0.29 g of N,N-diallylcarbamoyl chloride was added at room temperature. After stirring for 8 hours, the resultant solution was concentrated, and the residue was subjected to silica gel column chromatography to obtain 0.34 g of 3-(4-trifluoromethylpyridin-2-yl)-N,N-diallyl-1,2,4-oxadiazol-5-one-4-carboxamide (present compound (17)).

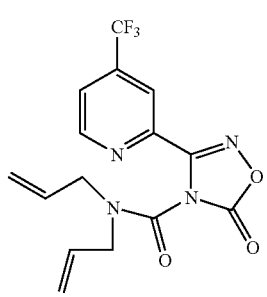

Present Compound (17)

¹H-NMR: 4.05-4.19 (m, 4H), 5.22-5.46 (m, 4H), 5.84-5.97 (m, 2H), 7.72 (d, 1H), 8.21 (s, 1H), 8.84 (d, 1H)

Production Example 24

To 1 ml of pyridine were added 0.28 g of 1,8-diazabicyclo[5,4,0]undec-7-ene, and 0.3 g of 3-(4-trifluoromethylpyridin-2-yl)-1,2,4-oxadiazol-5-one, and 0.3 g of N,N-diisopropylcarbamoyl chloride was added at room temperature. After stirring for 8 hours, the resultant solution was concentrated, and the residue was subjected to silica gel column chromatography to obtain 0.09 g of 3-(4-trifluoromethylpyridin-2-yl)-N,N-diisopropyl-1,2,4-oxadiazol-5-one-4-carboxamide (present compound (18)).

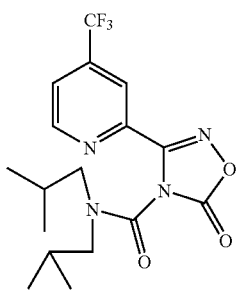

Present Compound (18)

¹H-NMR: 1.30 (d, 3H), 1.38 (d, 3H), 1.47 (d, 3H), 1.50 (d, 3H), 3.59-3.69 (m, 1H), 4.10-4.18 (m, 1H), 7.69 (d, 1H), 8.21 (s, 1H), 8.79 (d, 1H)

Production Example 25

To 1 ml of pyridine were added 0.23 g of 1,8-diazabicyclo[5,4,0]undec-7-ene, and 0.25 g of 3-(4-trifluoromethylpyridin-2-yl)-1,2,4-oxadiazol-5-one, and 0.22 g of 1-piperidinecarbonyl chloride was added at room temperature. After stirring for 5 hours, the resultant solution was concentrated, and the residue was subjected to silica gel column chromatography to obtain 0.31 g of 4-(1-piperidinecarbonyl)-3-(4-trifluoromethylpyrpidin-2-yl)-1,2,4-oxadiazol-5-one (present compound (19)).

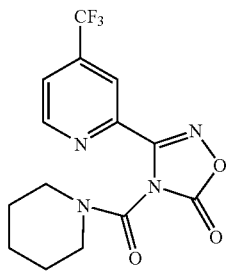

Present Compound (19)

¹H-NMR: 1.71-1.82 (m, 6H), 3.51-3.80 (m, 4H), 7.70 (d, 1H), 8.19 (s, 1H), 8.85 (d, 1H)

Production Example 26

To 1 ml of pyridine were added 0.18 g of 1,8-diazabicyclo[5,4,0]undec-7-ene, and 0.2 g of 3-(4-trifluoromethylpyridin-2-yl)-1,2,4-oxadiazol-5-one, and 0.18 g of 1-morpholinecarbonyl chloride was added at room temperature. After stirring for 5 hours, the resultant solution was concentrated, and the residue was subjected to silica gel column chromatography to obtain 0.32 g of 4-(1-morpholinecarbonyl)-3-(4-trifluoromethylpyridin-2-yl)-1,2,4-oxadiazol-5-one (present compound (20)).

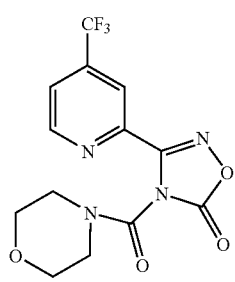

Present Compound (20)

¹H-NMR: 1.71-1.82 (m, 6H), 3.51-3.80 (m, 4H), 7.70 (d, 1H), 8.19 (s, 1H), 8.85 (d, 1H)

Production Example 27

To 1 ml of pyridine were added 0.18 g of 1,8-diazabicyclo[5,4,0]undec-7-ene, and 0.2 g of 3-(4-trifluoromethylpyridin-2-yl)-1,2,4-oxadiazol-5-one, and 0.15 g of N-methoxy-N-methylcarbamoyl chloride was added at room temperature. After stirring at 50° C. for 4 hours, the resultant solution was concentrated, and the residue was subjected to silica gel column chromatography to obtain 0.19 g of 3-(4-trifluoromethylpyridin-2-yl)-N-methoxy-N-methyl-1,2,4-oxadiazol-5-one-4-carboxamide (present compound (21))

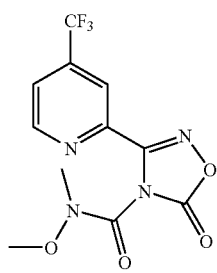

Present Compound (21)

¹H-NMR: 3.41-3.61 (bs, 3H), 3.92-3.74 (m, 3H), 7.71 (d, 1H), 8.24 (s, 1H), 8.84 (d, 1H)

Production Example 28

To 1 ml of ethanol were added 0.12 g of triethylamine, 0.2 g of 3-(4-trifluoromethylpyridin-2-yl)-1,2,4-oxadiazol-5-one, and 0.05 g of acrolein, the mixture was stirred at room temperature for 18 hours, and concentrated, and the residue was subjected to silica gel column chromatography to obtain 0.16 g of 3-[3-(4-trifluoromethylpyridin-2-yl)-1,2,4-oxadiazol-5-on-4-yl]propionaldehyde (present compound (22)).

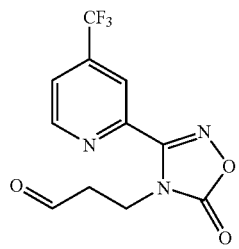

Present Compound (22)

¹H-NMR: 3.07 (t, 2H), 4.50 (t, 3H), 7.74 (d, 1H), 8.29 (s, 1H), 8.90 (d, 1H), 9.80 (s, 1H)

Production Example 29

Into 2 ml of N,N-dimethylformamide was suspended 0.07 g of sodium hydride (60% oily), and 0.2 g of 3-(4-trifluoromethylpyridin-2-yl)-1,2,4-oxadiazol-5-one was added at room temperature. After stirring for 10 minutes, 0.14 g of cyclopropylmethyl bromide was added, and the mixture was stirred at 80° C. for 6 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.13 g of 4-(cyclopropylmethyl)-3-(4-trifluoromethylpyridin-2-yl)-1,2,4-oxadiazol-5-one (present compound (23)).

Present Compound (23)

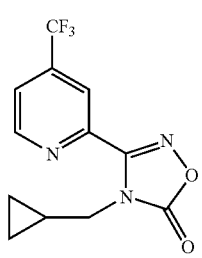

¹H-NMR: 0.38-0.42 (m, 2H), 0.48-0.53 (m, 2H), 1.19-1.28 (m, 1H), 4.09 (d, 2H), 7.73 (d, 1H), 8.31 (s, 1H), 8.95 (d, 1H)

Production Example 30

To 5 ml of tetrahydrofuran were added 0.6 g of 4-(2,2,2-trifluoroethoxy)pyridine-2-carboxamide=oxime and 0.54 g of 1,1'-carbonyldiimidazole, and the mixture was stirred at room temperature for 2 hours. Thereafter, 0.51 g of 1,8-diazabicyclo[5,4,0]undec-7-ene was added at 10° C., and the mixture was stirred for 3 hours. To the reaction solution were added water and a 10% aqueous HCl solution, this was extracted with ethyl acetate three times, and the organic layers were combined, dried with anhydrous magnesium sulfate, and concentrated. The residue was subjected to silica gel column chromatography to obtain 0.65 g of 3-[4-(2,2,2-trifluoroethoxy)pyridin-2-yl]-1,2,4-oxadiazol-5-one (present compound (24)).

Present Compound (24)

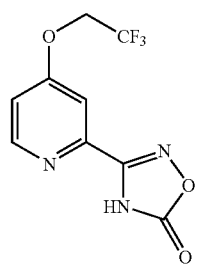

¹H-NMR (DMSO-d₆): 5.05 (q, 2H), 7.37 (dd, 1H), 7.64 (d, 1H), 8.64 (d, 1H), 13.17 (bs, 1H)

Production Example 31

To 2 ml of pyridine were added 0.25 g of 1,8-diazabicyclo[5,4,0]undec-7-ene, and 0.3 g of 3-[4-(2,2,2-trifluoroethoxy)pyridin-2-yl]-1,2,4-oxadiazol-5-one, and 0.22 g of 2,2-dimethylbutanoyl chloride was added at room temperature. After stirring for 2 hours, the mixture was further stirred at 60° C. for 2 hours. The resultant solution was concentrated, and the residue was subjected to silica gel column chromatography to obtain 0.13 g of 4-(2,2-dimethylbutanoyl)-3-[4-(2,2,2-trifluoroethoxy)pyridin-2-yl]-1,2,4-oxadiazol-5-one (present compound (25)).

Present Compound (25)

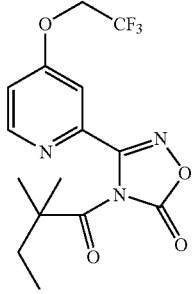

¹H-NMR: 0.99 (t, 3H), 1.39 (s, 6H), 1.91 (q, 2H), 4.48 (q, 2H), 7.02 (dd, 1H), 7.51 (d, 1H), 8.45 (d, 1H)

Production Example 32

To 4 ml of tetrahydrofuran were added 0.64 g of 4-(2,2,3,3,3-pentafluoropropoxy)pyridine-2-carboxamide=oxime and 0.47 g of 1,1'-carbonyldiimidazole, and the mixture was stirred at room temperature for 2 hours. Thereafter, 0.45 g of 1,8-diazabicyclo[5,4,0]undec-7-ene was added at 10° C., and the mixture was stirred for 8 hours. To the reaction solution were added water and a 10% aqueous HCl solution, the resultant solution was extracted with ethyl acetate three times, and the organic layers were combined, dried with anhydrous magnesium sulfate, and concentrated. The residue was washed with hexane three times to obtain 0.63 g of 3-[4-(2,2,3,3,3-pentafluoropropoxy)pyridin-2-yl]-1,2,4-oxadiazol-5-one (present compound (26)).

Present Compound (26)

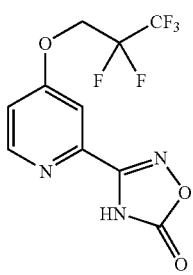

¹H-NMR (DMSO-d₆): 5.14 (t, 2H), 7.38 (dd, 1H), 7.66 (d, 1H), 8.64 (d, 1H), 13.17 (bs, 1H)

Production Example 33

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.18 g of chloromethylbenzoate, and the mixture was stirred at 70° C. for 3 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.12 g of [3-(4-trifluoromethylpyridin-2-yl)-1,2,4-oxadiazol-5-on-4-yl]methyl=benzoate (present compound (27)).

Present Compound (27)

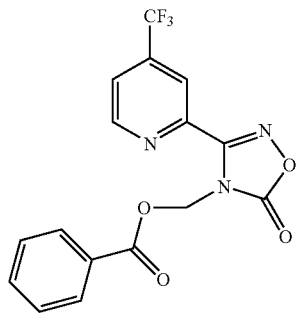

¹H-NMR: 6.44 (s, 2H), 7.38-7.42 (m, 2H), 7.53-7.59 (m, 1H), 7.71 (d, 1H), 7.79-7.92 (m, 2H), 8.30 (s, 1H), 8.87 (d, 1H)

Production Example 34

To 5 ml of tetrahydrofuran were added 0.5 g of 4-(2,2,2-trifluoro-1-methylethoxy)pyridine-2-carboxamide=oxime and 0.48 g of 1,1'-carbonyldiimidazole, and the mixture was stirred at room temperature for 2 hours. Thereafter, 0.45 g of 1,8-diazabicyclo[5,4,0]undec-7-ene was added, and the mixture was stirred for 8 hours. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.55 g of 3-[4-(2,2,2-trifluoro-1-methylethoxy)pyridin-2-yl]-1,2,4-oxadiazol-5-one (present compound (28)).

Present Compound (28)

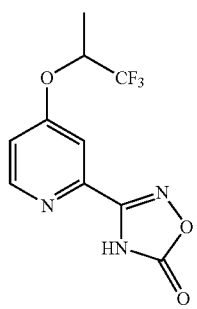

¹H-NMR (DMSO-$d_6$): 1.48 (d, 3H), 5.64-5.70 (m, 1H), 7.40 (dd, 1H), 7.66 (d, 1H), 8.63 (d, 1H), 13.15 (bs, 1H)

Production Example 35

To 5 ml of tetrahydrofuran were added 0.66 g of 6-methyl-4-(2,2,2-trifluoroethoxy)pyridine-2-carboxamide=oxime and 0.56 g of 1,1'-carbonyldiimidazole, and the mixture was stirred at room temperature for 2 hours. Thereafter, 0.52 g of 1,8-diazabicyclo[5,4,0]undec-7-ene was added at 10° C., and the mixture was stirred for 8 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.69 g of 3-[6-methyl-4-(2,2,2-trifluoroethoxy)pyridin-2-yl]-1,2,4-oxadiazol-5-one (present compound (29)).

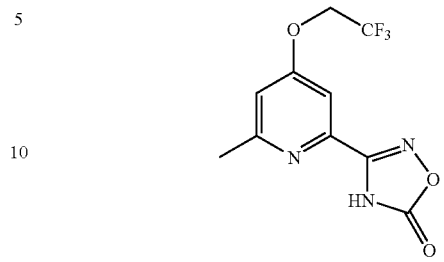

¹H-NMR (DMSO-$d_6$): 2.53 (s, 3H), 5.00 (q, 2H), 7.26 (d, 1H), 7.45 (d, 1H)

Production Example 36

To 5 ml of tetrahydrofuran were added 0.63 g of 6-methyl-4-(2,2,2-trifluoro-1-methylethoxy)pyridine-2-carboxamide=oxime and 0.51 g of 1,1'-carbonylimidazole, and the mixture was stirred at room temperature for 2 hours. Thereafter, 0.47 g of 1,8-diazabicyclo[5,4,0]undec-7-ene was added, and the mixture was stirred. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.64 g of 3-[6-methyl-4-(2,2,2-trifluoro-1-methylethoxy)pyridin-2-yl]-1,2,4-oxadiazol-5-one (present compound (30)).

Present Compound (30)

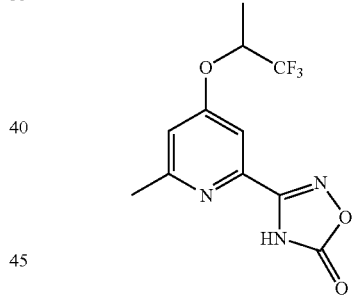

¹H-NMR (DMSO-$d_6$): 1.46 (d, 3H), 2.53 (s, 3H), 5.56-5.63 (m, 1H), 7.29 (d, 1H), 7.47 (d, 1H)

Production Example 37

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 10 minutes, 0.5 g of chloromethyl 2-chlorobenzoate, and the mixture was stirred at 60° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.07 g of [3-(4-trifluoromethylpyridin-2-yl)-1,2,4-oxadiazol-5-on-4-yl]methyl 2-chlorobenzoate (present compound (31)).

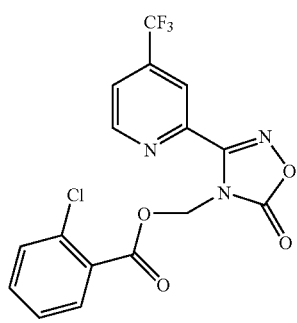

Present Compound (31)

$^1$H-NMR: 6.45 (s, 2H), 7.25-7.29 (m, 1H), 7.39-7.42 (m, 2H), 7.71-7.73 (m, 2H), 8.30 (s, 1H), 8.91 (d, 1H)

Production Example 38

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.23 g of chloromethyl 3-chlorobenzoate was added, ad the mixture was stirred at 60° C. for 3 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.18 g of [3-(4-trifluoromethylpyridin-2-yl)-1,2,4-oxadiazol-5-on-4-yl]methyl 3-chlorobenzoate (present compound (32)).

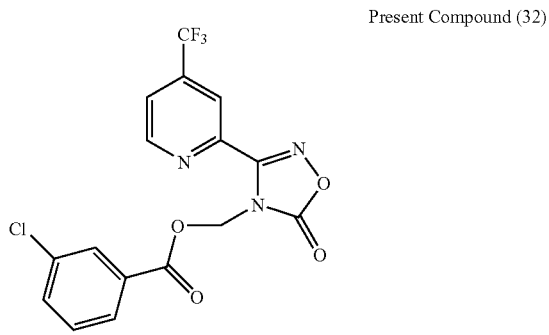

Present Compound (32)

$^1$H-NMR: 6.45 (s, 2H), 7.35 (t, 1H), 7.52-7.54 (m, 1H), 7.73 (d, 1H), 7.80-7.83 (m, 1H), 7.87-7.88 (m, 1H), 8.31 (s, 1H), 8.88 (d, 1H)

Production Example 39

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.16 g of benzyl=chloromethyl=ether was added, and the mixture was stirred at 60° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.24 g of 4-benzyloxymethyl-3-(4-trifluoromethylpyridin-2-yl)-1,2,4-oxadiazol-5-one (Present compound (33)).

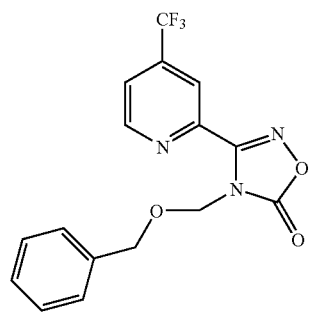

Present Compound (33)

$^1$H-NMR: 4.62 (s, 2H), 5.73 (s, 2H), 7.17-7.20 (m, 2H), 7.27-7.29 (m, 3H), 7.70 (d, 1H), 8.17 (s, 1H), 8.89 (d, 1H)

Production Example 40

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 10 minutes, 0.19 g of chloromethyl 3-methylbenzoate was added, and the mixture was stirred at 70° C. for 3 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.08 g of [3-(4-trifluoromethylpyridin-2-yl)-1,2,4-oxadiazol-5-on-4-yl]methyl 3-methylbenzoate (present compound (34)).

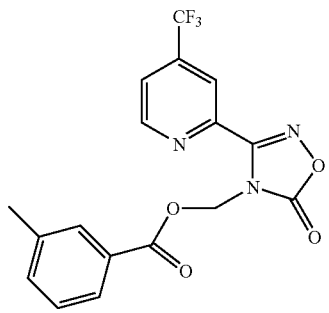

Present Compound (34)

$^1$H-NMR: 2.35 (s, 3H), 6.43 (s, 2H), 7.28 (t, 1H), 7.37 (d, 1H), 7.68-7.72 (m, 3H), 8.29 (s, 1H), 8.87 (d, 1H)

Production Example 41

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 10 minutes, 0.29 g of chloromethyl 4-methylbenzoate was added, and the mixture was stirred at 70° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.25 g of [3-(4-trifluoromethylpyridin-2-yl)-1,2,4-oxadiazol-5-on-4-yl]methyl 4-methylbenzoate (present compound (35)).

Present Compound (35)

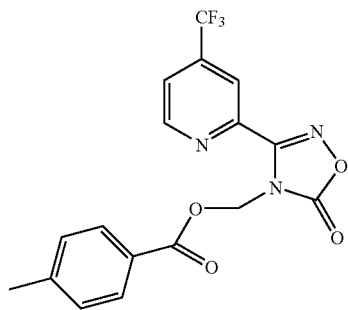

¹H-NMR: 2.38 (s, 3H), 6.42 (s, 2H), 7.19 (d, 2H), 7.69 (d, 1H), 7.79 (d, 2H), 8.29 (s, 1H), 8.86 (d, 1H)

Production Example 42

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.35 g of chloromethyl 4-t-butylbenzoate was added, and the mixture was stirred at 70° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.23 g of [3-(4-trifluoromethylpyridin-2-yl)-1,2,4-oxadiazol-5-on-4-yl]methyl 4-t-butylbenzoate (present compound 36)).

Present Compound (36)

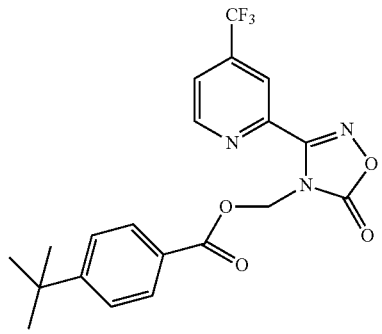

¹H-NMR: 1.30 (s, 9H), 6.42 (s, 2H), 7.40 (dd, 2H), 7.70 (d, 1H), 7.83 (dd, 2H), 8.28 (s, 1H), 8.87 (d, 1H)

Production Example 43

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.35 g of chloromethyl 3-fluorobenzoate was added, and the mixture was stirred at 70° C. for 6 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.12 g of [3-(4-trifluoromethylpyridin-2-yl)-1,2,4-oxadiazol-5-on-4-yl]methyl 3-fluorobenzoate (present compound (37)).

Present Compound (37)

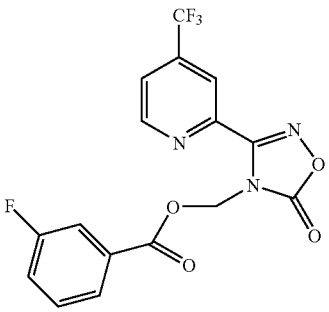

¹H-NMR: 6.45 (s, 2H), 7.26 (tdd, 1H), 7.39 (td, 1H), 7.57-7.61 (m, 1H), 7.71-7.73 (m, 2H), 8.31 (s, 1H), 8.87 (d, 1H)

Production Example 44

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.29 g of chloromethyl 4-fluorobenzoate was added, and the mixture was stirred at 70° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.17 g of [3-(4-trifluoromethylpyridin-2-yl)-1,2,4-oxadiazol-5-on-4-yl]methyl 4-fluorobenzoate (present compound (38)).

Present Compound (38)

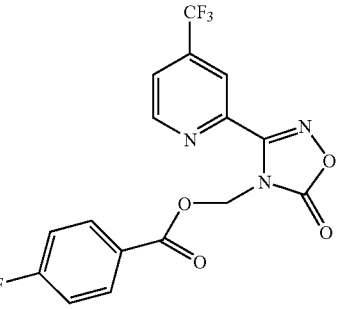

¹H-NMR: 6.43 (s, 2H), 7.08 (t, 2H), 7.71 (d, 1H), 7.94 (dd, 2H), 8.30 (s, 1H), 8.86 (d, 1H)

Production Example 45

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.37 g of chloromethyl 3,5-dichlorobenzoate was added, and the mixture was stirred at 70° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.31 g of [3-(4-trifluoromethylpyridin-2-yl)-1,2,4-oxadiazol-5-on-4-yl]methyl 3,5-dichlorobenzoate (present compound (39)).

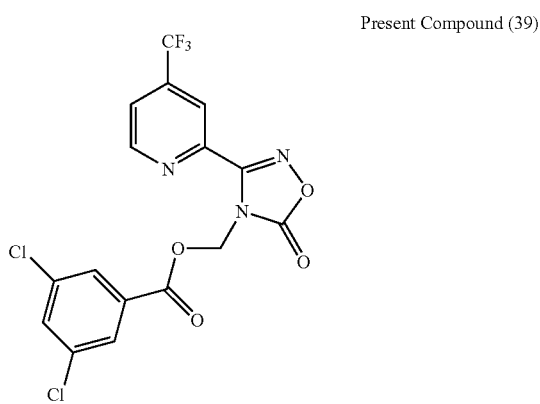

Present Compound (39)

¹H-NMR: 6.46 (s, 2H), 7.53 (t, 1H), 7.74 (d, 1H), 7.78 (d, 2H), 8.32 (s, 1H), 8.88 (d, 1H)

Production Example 46

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.32 g of chloromethyl 3,5-difluorobenzoate was added, and the mixture was stirred at 70° C. for 5 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.23 g of [3-(4-trifluoromethylpyridin-2-yl)-1,2,4-oxadiazol-5-on-4-yl]methyl 3,5-difluorobenzoate (present compound (40)).

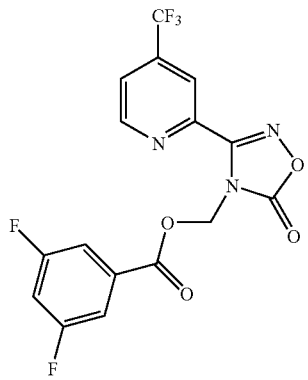

Present Compound (40)

¹H-NMR: 6.45 (s, 2H), 7.02 (tt, 1H), 7.41-7.47 (m, 2H), 7.73 (d, 2H), 8.32 (s, 1H), 8.86 (d, 1H)

Production Example 47

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.32 g of chloromethyl 3,4-dichlorobenzoate was added, and the mixture was stirred at 70° C. for 6 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.23 g of [3-(4-trifluoromethylpyridin-2-yl)-1,2,4-oxadiazol-5-on-4-yl]methyl 3,4-dichlorobenzoate (present compound (41)).

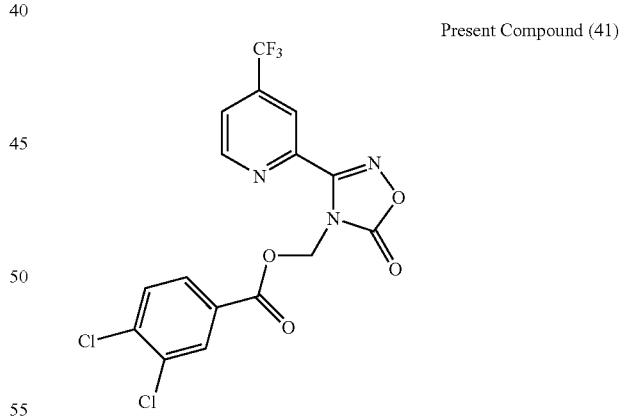

Present Compound (41)

¹H-NMR: 6.44 (s, 2H), 7.50 (d, 1H), 7.72 (d, 1H), 7.76 (dd, 1H), 7.99 (d, 1H), 8.32 (s, 1H), 8.85 (d, 1H)

Production Example 48

Into 2 ml of N,N-dimethylformamide was suspended 0.05 g of sodium hydride (60% oily), and 0.2 g of 3-(4-trifluoromethylpyridin-2-yl)-1,2,4-oxadiazol-5-one was added at room temperature. After stirring for 15 minutes, 0.21 g of chloromethyl-3,4-difluorobenzoate was added, and the mixture was stirred at 70° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.06 g of [3-(4-trifluoromethylpyridin-2-yl)-1,2,4-oxadiazol-5-on-4-yl]methyl 3,4-difluorobenzoate (present compound (42)).

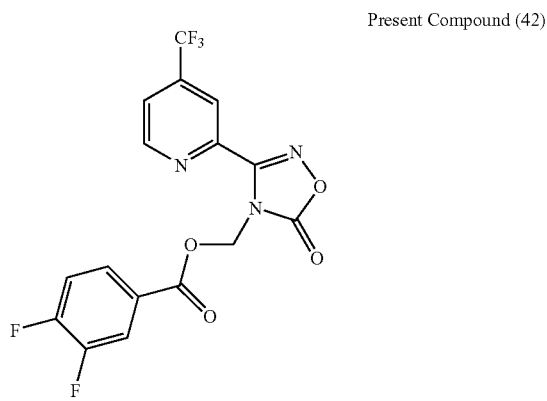

Present Compound (42)

$^1$H-NMR: 6.44 (s, 2H), 7.16-7.23 (m, 1H), 7.71-7.77 (m, 3H), 8.31 (s, 1H), 8.86 (d, 1H)

Production Example 49

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.33 g of chloromethyl 4-trifluoromethylbenzoate was added, and the mixture was stirred at 70° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.1 g of [3-(4-trifluoromethylpyridin-2-yl)-1,2,4-oxadiazol-5-on-4-yl]methyl 4-trifluoromethylbenzoate (present compound (43)).

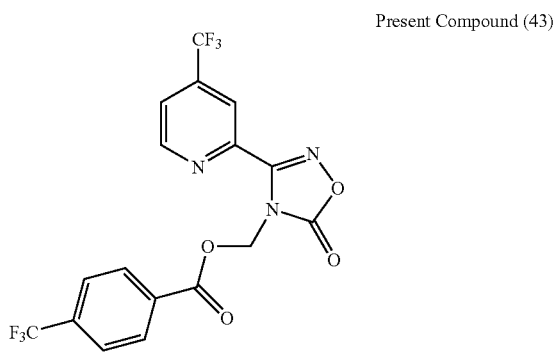

Present Compound (43)

$^1$H-NMR: 6.24 (s, 2H), 7.88 (d, 1H), 8.07-8.11 (m, 3H, involving a doublet at 8.20), 8.30 (s, 1H), 8.98 (d, 1H)

Production Example 50

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.33 g of chloromethyl 3-trifluoromethylbenzoate was added, and the mixture was stirred at 70° C. for 6 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.32 g of [3-(4-trifluoromethylpyridin-2-yl)-1,2,4-oxadiazol-5-on-4-yl]methyl 3-trifluoromethylbenzoate (present compound (44)).

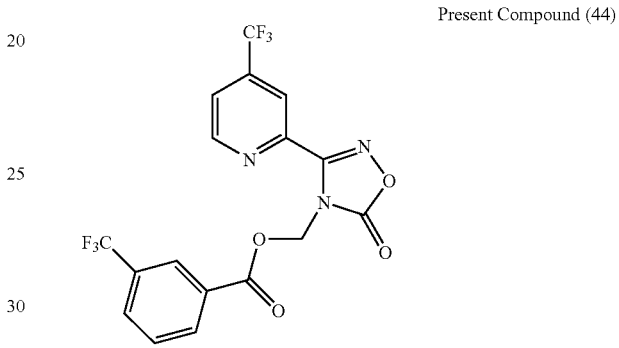

Present Compound (44)

$^1$H-NMR: 6.48 (s, 2H), 7.57 (d, 1H), 7.72 (d, 1H), 7.83 (d, 1H), 8.13 (d, 1H), 8.16 (s, 1H), 8.32 (s, 1H), 8.87 (d, 1H)

Production Example 51

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.40 g of chloromethyl 3-trifluoromethoxybenzoate was added, and the mixture was stirred at 70° C. for 6 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.2 g of [3-(4-trifluoromethylpyridin-2-yl)-1,2,4-oxadiazol-5-on-4-yl]methyl 3-trifluoromethoxybenzoate (present compound (45)).

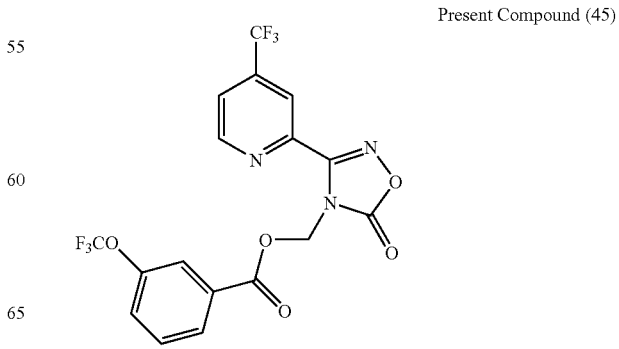

Present Compound (45)

¹H-NMR: 6.46 (s, 2H), 7.41-7.48 (m, 2H), 7.71-7.74 (m, 2H), 7.87 (dt, 1H), 8.31 (s, 1H), 8.86 (d, 1H)

Production Example 52

Into 2 ml of N,N-dimethylformamide was suspended 0.07 g of sodium hydride (60% oily), and 0.3 g of 3-(4-trifluoromethylpyridin-2-yl)-1,2,4-oxadiazol-5-one was added at room temperature. After stirring for 15 minutes, 0.39 g of chloromethyl 3-bromobenzoate was added, and the mixture was stirred at 70° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.25 g of [3-(4-trifluoromethylpyridin-2-yl)-1,2,4-oxadiazol-5-on-4-yl]methyl 3-bromobenzoate (present compound (46)).

Present Compound (46)

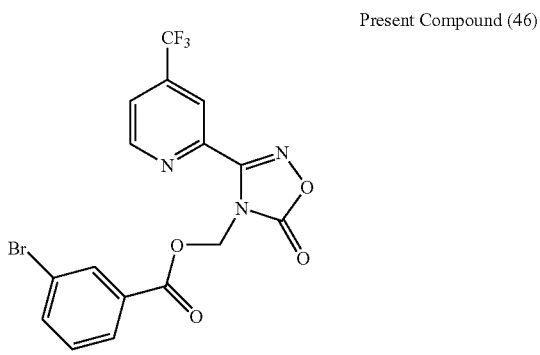

¹H-NMR: 6.45 (s, 2H), 7.29 (t, 1H), 7.69 (ddd, 1H), 7.72 (d, 1H), 7.86 (dt, 1H), 8.03 (t, 1H), 8.31 (s, 1H), 8.87 (d, 1H)

Production Example 53

To 4 ml of tetrahydrofuran were added 0.55 g of 3,5-dichloro-4-(2,2,2-trifluoroethoxy)pyridine-2-carboxamide=oxime and 0.38 g of 1,1'-carbonyldiimidazole, and the mixture was stirred at room temperature for 2 hours. Thereafter, 0.36 g of 1,8-diazabicyclo[5,4,0]undec-7-ene was added at 10° C., and the mixture was stirred for 8 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.56 g of 3-[3,5-dichloro-4-(2,2,2-trifluoroethoxy)pyridin-2-yl]-1,2,4-oxadiazol-5-one (present compound (47)).

Present Compound (47)

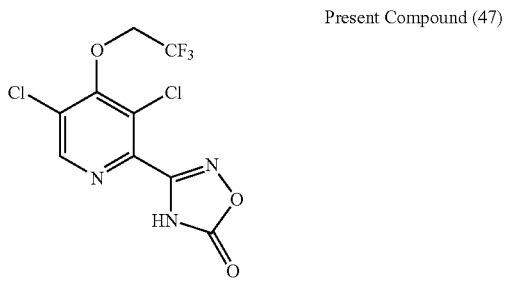

¹H-NMR (DMSO-d₆): 5.03 (q, 2H), 8.89 (s, 1H), 13.18 (bs, 1H)

Production Example 54

To 4 ml of tetrahydrofuran were added 0.55 g of 3,5-dichloro-4-(2,2,2-trifluoro-1-methylethoxy)pyridine-2-carboxamide=oxime and 0.36 g of 1,1'-carbonyldiimidazole, and the mixture was stirred at room temperature for 2 hours. Thereafter, 0.34 g of 1,8-diazabicyclo[5,4,0]undec-7-ene was added, and the mixture was stirred for 16 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.5 g of 3-[3,5-dichloro-4-(2,2,2-trifluoro-1-methylethoxy)pyridin-2-yl]-1,2,4-oxadiazol-5-one (present compound (48)).

Present Compound (48)

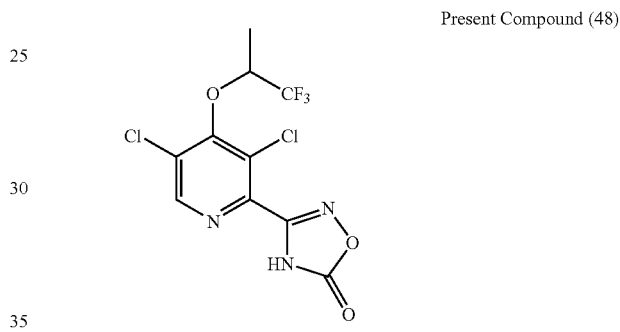

¹H-NMR (DMSO-d₆): 1.56 (d, 3H), 5.31-5.37 (m, 1H), 8.88 (s, 1H), 13.15 (bs, 1H)

Production Example 55

To 4 ml of tetrahydrofuran were added 0.63 g of 4-[2,2,2-trifluoro-1-(triethylsilyloxy)ethyl]pyridine-2-carboxamide=oxime and 0.41 g of 1,1'-carbonyldiimidazole, and the mixture was stirred at room temperature for 2 hours. Thereafter, 0.38 g of 1,8-diazabicyclo[5,4,0]undec-7-ene was added, and the mixture was stirred for 4 hours. To the reaction solution were added water and 10% HCl, the resultant solution was extracted with ethyl acetate three times, and the organic layers were combined, dried with anhydrous magnesium sulfate, and concentrated. The resulting crude product was used in the next reaction without purification.

To 4 ml of tetrahydrofuran was added the crude product, and 2.7 ml of tetrabutylammonium fluoride (1M tetrahydrofuran solution) was added at 0° C. After stirring at room temperature for 4 hours, water and 10% HCl were added to the reaction solution, extracted with ethyl acetate three times. The organic layers were combined, dried with anhydrous magnesium sulfate, and concentrated. The residue was subjected to silica gel column chromatography to obtain 0.35 g of 3-[4-(2,2,2-trifluoro-1-hydroxyethyl)pyridin-2-yl]-1,2,4-oxadiazol-5-one (present compound (55)).

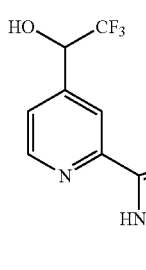

Present Compound (55)

$^1$H-NMR (DMSO-$d_6$): 5.47-5.54 (m, 1H), 7.36 (d, 1H), 7.77 (d, 1H), 8.13 (s, 1H), 8.82 (d, 1H)

Production Example 56

To 2 ml of tetrahydrofuran were added 0.15 g of 4-(2,2,2-trifluoro-1-methoxyethyl)pyridine-2-carboxamide=oxime and 0.14 g of 1,1'-carbonyldiimidazole, and the mixture was stirred at room temperature for 2 hours. Thereafter, 0.13 g of 1,8-diazabicyclo[5,4,0]undec-7-ene was added at 0° C., and the mixture was stirred for 5 hours. To the reaction solution were added water and a 10% aqueous HCl solution, the resultant solution was extracted with ethyl acetate three times, and the organic layers were combined, dried with anhydrous magnesium sulfate, and concentrated. The residue was subjected to silica gel column chromatography to obtain 0.13 g of 3-[4-(2,2,2-trifluoro-1-methoxyethyl)pyridin-2-yl]-1,2,4-oxadiazol-5-one (present compound (56)).

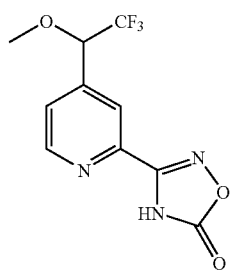

Present Compound (56)

$^1$H-NMR (DMSO-$d_6$): 3.44 (s, 3H), 5.43 (q, 1H), 7.73 (d, 1H), 8.07 (s, 1H), 8.87 (d, 1H), 13.28 (bs, 1H)

Production Example 57

To 2 ml of ethanol were added 0.09 g of sodium bicarbonate and 0.07 g of hydroxylamine hydrochloride, and the mixture was heated to reflux for 1 hour. After allowing to cool, 0.17 g of 4-[2,2,2-trifluoro-1-(2-propenyloxy)ethyl]pyridine-2-carbonitrile was added at 0° C., and the mixture was stirred for 5 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The resulting crude product was used in the next reaction without purification.

To 2 ml of tetrahydrofuran were added the crude product and 0.17 g of 1,1'-carbonyldiimidazole, and the mixture was stirred at room temperature for 2 hours. Thereafter, 0.16 g of 1,8-diazabicyclo[5,4,0]undec-7-ene was added at 0° C., and the mixture was stirred for 4 hours. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.17 g of 3-{4-[2,2,2-trifluoro-1-(2-propenyloxy)ethyl]pyridin-2-yl}-1,2,4-oxadiazol-5-one (present compound (57)).

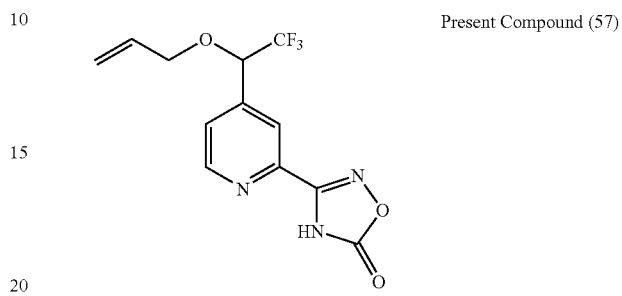

Present Compound (57)

$^1$H-NMR (DMSO-$d_6$): 4.15 (d, 2H), 5.23 (d, 1H), 5.32 (dd, 1H), 5.53 (q, 1H), 5.86-5.94 (m, 1H), 7.76 (d, 1H), 8.09 (s, 1H), 8.87 (d, 1H)

Production Example 58

To 2 ml of dimethyl sulfoxide were added 0.3 g of 3-[4-(2,2,2-trifluoro-1-hydroxyethyl)pyridin-2-yl]-1,2,4-oxadiazol-5-one and 0.48 ml of triethylamine, and 1 ml of a solution of 0.55 g of sulfur-trioxide-pyridine complex in dimethyl sulfoxide was added dropwise. After stirring for 8 hours, 0.17 g of sulfur-trioxide-pyridine complex was added, and the mixture was further stirred for 7 hours. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.18 g of 3-{4-[2,2,2-trifluoro-1,1-dihydroxyethyl]pyridin-2-yl}-1,2,4-oxadiazol-5-one (present compound (58)).

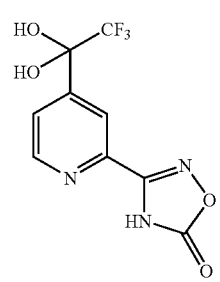

Present Compound (58)

$^1$H-NMR (DMSO-$d_6$): 7.81 (dd, 1H), 8.13 (s, 1H), 8.15 (s, 2H), 8.85 (dd, 1H), 13.24 (bs, 1H)

Production Example 59

To 8 ml of tetrahydrofuran were added 0.9 g of 4-pentafluoroethylpyridine-2-carboxamide=oxime and 0.95 g of 1,1'-carbonyldiimidazole, and the mixture was stirred at room temperature for 2 hours. Thereafter, 0.89 g of 1,8-diazabicyclo[5,4,0]undec-7-ene was added at 0° C., and the mixture was stirred for 2 hours. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.9 g of 3-(4-pentafluoroethylpyridin-2-yl)-1,2,4-oxadiazol-5-one (present compound (59)).

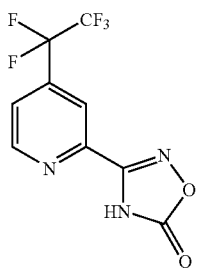

Present Compound (59)

$^1$H-NMR (DMSO-$d_6$): 8.06 (d, 1H), 8.17 (s, 1H), 9.08 (d, 1H), 13.40 (bs, 1H)

Production Example 60

To 3 ml of tetrahydrofuran were added 0.3 g of 4-(2,2,2-trifluoroethyl)pyridine-2-carboxamide=oxime and 0.39 g of 1,1'-carbonyldiimidazole, and the mixture was stirred at room temperature for 2 hours. Thereafter, 0.37 g of 1,8-diazabicyclo[5,4,0]undec-7-ene was added at 0° C., and the mixture was stirred at room temperature for 4 hours. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.33 g of 3-[4-(2,2,2-trifluoroethyl)pyridin-2-yl]-1,2,4-oxadiazol-5-one (present compound (60)).

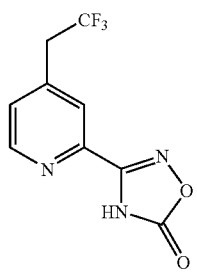

Present Compound (60)

$^1$H-NMR (DMSO-$d_6$): 3.94 (q, 2H), 7.67 (d, 1H), 8.04 (s, 1H), 8.78 (d, 1H)

Production Example 61

To 4 ml of tetrahydrofuran were added 0.5 g of 4-[2,2,2-trifluoro-1-methyl-1-(trimethylsilyloxy)ethyl]pyridine-2-carboxamide=oxime and 0.42 g of 1,1'-carbonyldiimidazole, and the mixture was stirred at room temperature for 1 hour and 30 minutes. Thereafter, 0.4 g of 1,8-diazabicyclo[5,4,0]undec-7-ene was added at 0° C., and the mixture was stirred at room temperature for 4 hours. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.43 g of 3-{4-[2,2,2-trifluoro-1-methyl-1-(trimethylsilyloxy)ethyl]pyridin-2-yl}-1,2,4-oxadiazol-5-one (present compound (61)).

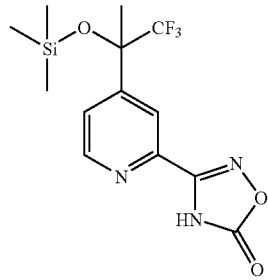

Present Compound (61)

$^1$H-NMR (DMSO-$d_6$): 0.15 (s, 9H), 1.91 (s, 3H), 7.84 (d, 1H), 8.11 (s, 1H), 8.85 (d, 1H), 13.25 (bs, 1H)

Production Example 62

To 3 ml of tetrahydrofuran was added 12 g of 3-{4-[2,2,2-trifluoro-1-methyl-1-(trimethylsilyloxy)ethyl]pyridin-2-yl}-1,2,4-oxadiazol-5-one, and 1.3 ml of tetrabutylammonium=fluoride (1M tetrahydrofuran solution) was added at 0° C. After stirring at room temperature for 4 hours, water and 10% HCl were added to the reaction solution, the resultant solution was extracted with ethyl acetate three times, and the organic layers were combined, dried with anhydrous magnesium sulfate, and concentrated. The residue was subjected to silica gel column chromatography to obtain 0.29 g of 3-[4-(2,2,2-trifluoro-1-methyl-1-hydroxyethyl)pyridin-2-yl]-1,2,4-oxadiazol-5-one (present compound (62)).

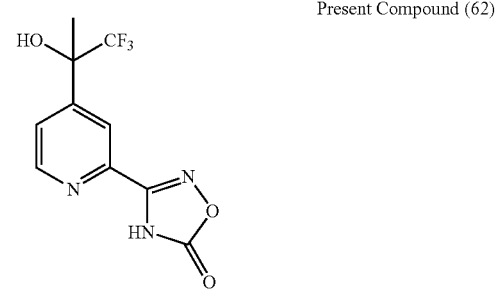

Present Compound (62)

$^1$H-NMR (DMSO-$d_6$): 1.74 (s, 3H), 7.17 (s, 1H), 7.84 (d, 1H), 8.16 (s, 1H), 8.82 (d, 1H), 13.24 (bs, 1H)

Production Example 63

To 2 ml of pyridine were added 0.16 g of 1,8-diazabicyclo[5,4,0]undec-7-ene, and 0.2 g of 3-(4-pentafluoroethylpyridin-2-yl)-1,2,4-oxadiazol-5-one, and 0.14 g of 1-pyrrolidinecarbonyl chloride was added at room temperature. After stirring for 4 hours, the resultant solution was concentrated, and the residue was subjected to silica gel column chromatography to obtain 0.17 g of 4-(1-pyrrolidinecarbonyl)-3-(4-pentafluoroethylpyridin-2-yl)-1,2,4-oxadiazol-5-one (present compound (63)).

Present Compound (63)

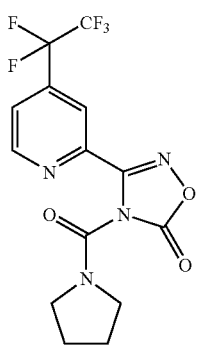

¹H-NMR: 2.03-2.09 (m, 4H), 3.60-3.71 (m, 4H), 7.68 (d, 1H), 8.18 (s, 1H), 8.84 (d, 1H)

Production Example 64

Into 2 ml of N,N-dimethylformamide was suspended 0.04 g of sodium hydride (60% oily), and 0.2 g of 3-(4-pentafluoroethyl)pyridin-2-yl)-1,2,4-oxadiazol-5-one was added at room temperature. After stirring for 10 minutes, 0.16 g of benzyl=chloromethyl=ether was added, and the mixture was stirred at 60° C. for 5 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.19 g of 4-benzyloxymethyl-3-(4-pentafluoroethyl)pyridin-2-yl)-1,2,4-oxadiazol-5-one (present compound (64)).

Present Compound (64)

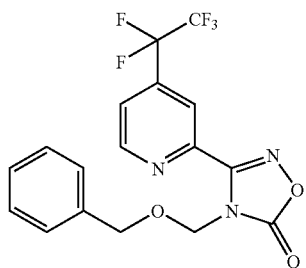

¹H-NMR: 4.63 (s, 2H), 5.74 (s, 2H), 7.17-7.20 (m, 2H), 7.27-7.31 (m, 2H), 7.38 (d, 1H), 7.69 (d, 1H), 8.17 (s, 1H), 8.90 (d, 1H)

Production Example 65

Into 2 ml of N,N-dimethylformamide was suspended 0.04 g of sodium hydride (60% oily), and 0.19 g of 3-(4-pentafluoroethyl)pyridin-2-yl)-1,2,4-oxadiazol-5-one was added at room temperature. After stirring for 10 minutes, 0.14 g of chloromethyl=benzoate was added, and the mixture was stirred at 60° C. for 6 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.12 g of [3-(4-pentafluoroethylpyridin-2-yl)-1,2,4-oxadiazol-5-on-4-yl] methyl=benzoate (present compound (65)).

Present Compound (65)

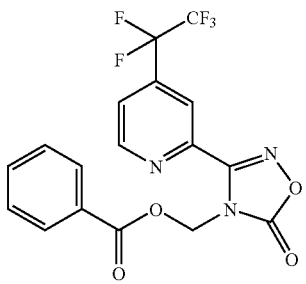

¹H-NMR: 6.44 (s, 2H), 7.40 (t, 2H), 7.54-7.58 (m, 1H), 7.70 (d, 1H), 7.91 (dd, 2H), 8.28 (s, 1H), 8.88 (d, 1H)

Production Example 66

To 6 ml of tetrahydrofuran were added 0.78 g of 4-(2,2,2-trifluoro-1-methyl-ethyl)pyridine-2-carboxamide=oxime and 0.81 g of 1,1'-carbonyldiimidazole, and the mixture was stirred at room temperature for 2 hours. Thereafter, 0.76 g of 1,8-diazabicyclo[5,4,0]undec-7-ene was added at 0° C., and the mixture was stirred at room temperature for 7 hours. To the reaction solution were added water and 10% HCl, the resultant solution was extracted with ethyl acetate three times, and the organic layers were combined, dried with anhydrous magnesium sulfate, and concentrated. The residue was subjected to silica gel column chromatography to obtain 0.7 g of 3-[4-(2,2,2-trifluoro-1-methyl-ethyl)pyridin-2-yl]-1,2,4-oxadiazol-5-one (present compound (66)).

Present Compound (66)

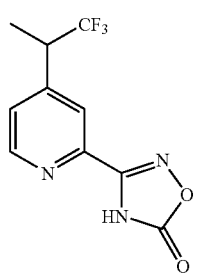

¹H-NMR (DMSO-d₆): 1.50 (d, 3H), 4.08-4.20 (m, 1H), 7.73 (d, 1H), 8.04 (s, 1H), 8.80 (d, 1H), 13.22 (bs, 1H)

Production Example 67

Into 2 ml of N,N-dimethylformamide was suspended 0.05 g of sodium hydride (60% oily), and 0.25 g of 3-[4-(2,2,2-trifluoro-1-methyl-ethyl)pyridin-2-yl]-1,2,4-oxadiazol-5-one was added at room temperature. After stirring for 10 minutes, 0.2 g of chloromethyl=benzoate was added, and the mixture was stirred at 60° C. for 4 hours. The reaction solution was allowed to cool to room temperature, and poured into an aqueous saturated ammonium chloride solution, followed by extraction with ethyl acetate three times. The organic layers were combined, washed with an aqueous saturated sodium chloride solution, dried with anhydrous magnesium sulfate, and concentrated. The residue was subjected to silica gel column chromatography to obtain 0.18 g of {3-[4-(2,2,2-trifluoro-1-methyl-ethyl)pyridin-2-yl]-1,2,4-oxadiazol-5-on-4-yl}methyl=benzoate (present compound (67)).

Present Compound (67)

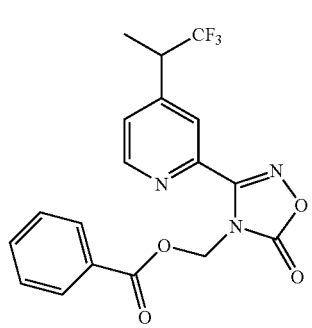

$^1$H-NMR: 1.56 (d, 3H), 3.50-3.58 (m, 1H), 6.44 (s, 2H), 7.37-7.41 (m, 2H), 7.44 (d, 1H), 7.53-7.57 (m, 1H), 7.89-7.91 (m, 2H), 8.01 (s, 1H), 8.65 (dd, 1H)

Then, Reference Production Examples will be shown regarding production of an intermediate for producing the present compound.

Reference Production Example 1

To 68 ml of chloroform were added 5 g of 4-trifluoromethylpyridine and 13.5 g of meta-chloroperbenzoic acid, and the mixture was stirred at 0° C. for 10 hours. Thereafter, the reaction solution was poured into an aqueous saturated sodium sulfite solution, followed by extraction with chloroform three times. The organic layers were combined, washed with an aqueous saturated sodium chloride solution, dried with anhydrous magnesium sulfate, and concentrated. The residue was subjected to silica gel column chromatography to obtain 4.5 g of 4-trifluoromethylpyridine=N-oxide.

4-Trifluoromethylpyridine=N-oxide

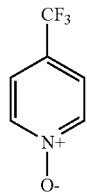

$^1$H-NMR (DMSO-d$_6$): 7.81 (d, 2H), 8.40 (d, 2H)

Reference Production Example 2

To 70 ml of acetonitrile were added 6 g of 4-trifluoromethylpyridine=N-oxide, 10.26 ml of triethylamine, and 10.95 g of trimethylsilyl cyanide, and the mixture was stirred at 90° C. for 20 hours. Thereafter, the reaction solution was allowed to cool to room temperature, and concentrated. The residue was subjected to silica gel column chromatography to obtain 4.5 g of 4-trifluoromethylpyridine-2-carbonitrile.

4-Trifluoromethylpyridine-2-carbonitrile

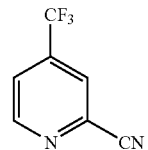

$^1$H-NMR: 7.77 (d, 1H), 7.92 (s, 1H), 8.96 (d, 1H)

Reference Production Example 3

To 72 ml of ethanol were added 6.18 g of sodium bicarbonate and 5.11 g of hydroxylamine hydrochloride, and the mixture was heated to reflux for 45 minutes. After allowing to cool, 6 g of 2-cyano-4-trifluoromethylpyridine was added at 0° C., and the mixture was stirred, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 5 g of 4-trifluoromethylpyridine-2-carboxamide=oxime.

4-Trifluoroemthylpyridine-2-carboxamide=oxime

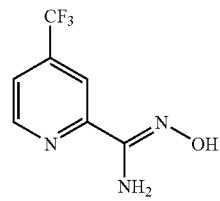

$^1$H-NMR (DMSO-d$_6$): 6.00 (bs, 2H), 7.80 (d, 1H), 8.06 (s, 1H), 8.86 (d, 1H), 10.19 (s, 1H)

Reference Production Example 4

To 22 ml of chloroform were added, 2 g of 2-chloro-4-trifluoromethylpyridine, and 4.39 g of meta-chloroperbenzoic acid, and the mixture was stirred at 60° C. for 12 hours. Thereafter, the reaction solution was poured into an aqueous saturated sodium sulfite solution, followed by extraction with chloroform three times. The organic layers were combined, washed with an aqueous saturated sodium chloride solution, dried with anhydrous magnesium sulfate, and concentrated.

The residue was subjected to silica gel column chromatography to obtain 1.5 g of 2-chloro-4-trifluoromethylpyridine=N-oxide.

2-Chloro-4-trifluoromethylpyridine=N-oxide

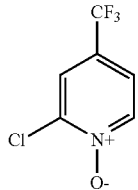

$^1$H-NMR (DMSO-$d_6$): 7.81 (dd, 1H), 8.36 (d, 1H), 8.62 (d, 1H)

Reference Production Example 5

To 16 ml of acetonitrile were added 1.5 g of 2-chloro-4-trifluoromethylpyridine N-oxide, 2.12 ml of triethylamine, and 2.26 g of trimethylsilyl cyanide, and the mixture was heated to reflux for 23 hours. Thereafter, the reaction solution was allowed to cool to room temperature, and concentrated. The residue was subjected to silica gel column chromatography to obtain 0.9 g of 2-chloro-6-cyano-4-trifluoromethylpyridine.

2-Chloro-6-cyano-4-trifluoromethylpyridine

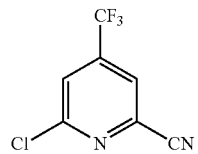

$^1$H-NMR: 7.80 (s, 1H), 7.84 (s, 1H)

Reference Production Example 6

To 9 ml of dimethyl sulfoxide were added 0.9 g of 2-chloro-6-cyano-4-trifluoromethylpyridine, and 0.76 g of potassium fluoride, and the mixture was stirred at 120° C. for 2 hours and 30 minutes. Thereafter, the reaction solution was allowed to cool to room temperature, and poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.7 g of 6-fluoro-4-trifluoromethylpyridine-2-carbonitrile.

6-Fluoro-4-trifluoromethylpyridine-2-carbonitrile

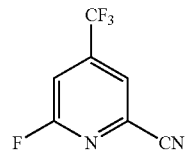

$^1$H-NMR: 7.46 (s, 1H), 7.84 (s, 1H)
$^{19}$F-NMR: −59.41 (s, 1H), −65.27 (s, 3H)

Reference Production Example 7

To 9 ml of ethanol were added 0.73 g of sodium bicarbonate and 0.61 g of hydroxylamine hydrochloride, and the mixture was heated to reflux for 1 hour. After allowing to cool, 0.7 g of 6-fluoro-4-trifluoromethylpyridine-2-carbonitrile was added at 0° C., and the mixture was stirred, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.6 g of 6-fluoro-4-trifluoromethylpyridine-2-carboxamide=oxime.

6-Fluoro-4-trifluoromethylpyridine-2-carboxamide=oxime

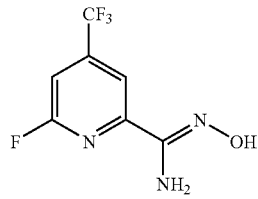

$^1$H-NMR (DMSO-$d_6$): 5.96 (s, 2H), 7.75 (s, 1H), 7.98 (s, 1H), 10.36 (bs, 1H)

Reference Production Example 8

Under an argon atmosphere, 3 g of 2,5-dichloropyridine was added to 40 ml of tetrahydrofuran, and 11.15 ml of lithium diisopropylamide (2M heptane/tetrahydrofuran/ethylbenzene solution) was added at −78° C. After stirring for 2 hours, 5.66 g of iodine was added, and the mixture was further stirred for 3 hours. The reaction solution was poured into an aqueous saturated sodium thiosulfate solution, and the resultant solution was extracted with tert-butyl=methyl=ether three times, washed with an aqueous saturated sodium chloride solution, dried with anhydrous magnesium sulfate, and concentrated. The residue was subjected to silica gel column chromatography to obtain 4 g of 2,5-dichloro-4-iodopyridine.

2,5-Dichloro-4-iodopyridine

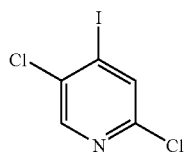

$^1$H-NMR: 7.85 (s, 1H), 8.34 (s, 1H)

Reference Production Example 9

Copper iodide (1.67 g) and potassium fluoride (0.51 g) were subjected to a reduced pressure (1 Torr) using a vacuum pump, and were heated with a heat gun for 20 minutes while stirring slowly. Under the argon atmosphere, 14 ml of N-methylpyrrolidine and 1.25 g of trifluoromethyltrimethylsilane were added, and a temperature was elevated to 50° C. over 20 minutes. After further stirring for 30 minutes, 2 g of 2,5-dichloro-4-iodopyridine was added, and the mixture was stirred for 20 hours. After allowing to cool, the reaction solution was poured into a 12% aqueous ammonia solution, the resultant solution was extracted with diethyl ether three times, washed with an aqueous saturated sodium chloride solution, dried with anhydrous magnesium sulfate, and concentrated. The residue was subjected to silica gel column chromatography to obtain 1 g of 2,5-dichloro-4-trifluoromethylpyridine.

2,5-Dichloro-4-trifluoromethylpyridine

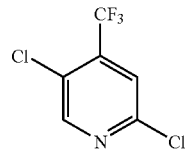

$^1$H-NMR: 7.62 (s, 1H), 8.55 (s, 1H)
$^{19}$F-NMR: −64.53 (s, 3H)

Reference Production Example 10

To 14 ml of N,N-dimethylformamide were added 1 g of 2,5-dichloro-4-trifluoromethylpyridine, 1.71 g of zinc cyanide and 0.34 g of tetrakistriphenylphosphine palladium, and the mixture was stirred at 90° C. for 10 hours. After allowing to cool, the reaction solution was poured into water, and the resultant solution was extracted with diethyl ether three times, washed with an aqueous saturated sodium chloride solution, dried with anhydrous magnesium sulfate, and concentrated. The residue was subjected to silica gel column chromatography to obtain 0.7 g of 5-chloro-4-trifluoromethylpyridine-2-carbonitrile.

5-Chloro-4-trifluoromethylpyridine-2-carbonitrile

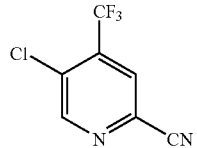

$^1$H-NMR: 7.95 (s, 1H), 8.87 (s, 1H)

Reference Production Example 11

To 7 ml of ethanol were added 0.61 g of sodium bicarbonate and 0.5 g of hydroxylamine hydrochloride, and the mixture was heated to reflux for 1 hour. After allowing to cool, 0.74 g of 5-chloro-4-trifluoromethylpyridine-2-carbonitrile was added at 0° C., and the mixture was stirred for 5 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.6 g of 5-chloro-4-trifluoromethylpyridine-2-carboxamide=oxime.

5-Chloro-4-trifluoromethylpyridine-2-carboxamide=oxime

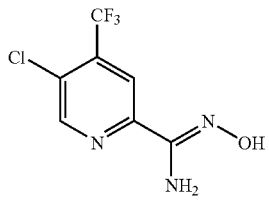

$^1$H-NMR (DMSO-d$_6$): 6.02 (s, 2H), 8.14 (s, 1H), 8.93 (s, 1H), 10.31 (s, 1H)

Reference Production Example 12

Under the argon atmosphere, 3 g of 2-bromo-4-fluoropyridine was added to 35 ml of tetrahydrofuran, and 9.38 ml of lithium diisopropylamide (2 mol/l heptaneketrahydrofuran/ethylbenzene solution) was added at −78° C. After stirring for 2 hours, 5.66 g of iodine was added, and the mixture was further stirred for 4 hours. The reaction solution was poured into an aqueous saturated sodium thiosulfate solution, the resultant solution was extracted with tert-butyl=methyl=ether three times, washed with an aqueous saturated sodium chloride solution, dried with anhydrous magnesium sulfate, and concentrated. The residue was subjected to silica gel column chromatography to obtain 4.1 g of 2-bromo-5-fluoro-4-iodopyridine.

2-Bromo-5-fluoro-4-iodopyridine

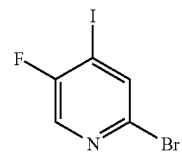

$^1$H-NMR: 7.91 (d, 1H), 8.13 (s, 1H)

Reference Production Example 13

Copper iodide (1.51 g) and potassium fluoride (0.46 g) were subjected to a reduced pressure (1 Ton) using a vacuum pump, and were heated with a heat gun for 20 minutes while stirring slowly. Under the argon atmosphere, 13 ml of N-methylpyrrolidine and 1.13 g of trifluoromethyltrimethylsilane were added at room temperature, and a temperature was elevated to 50° C. over 20 minutes. After further stirring for 1 hour, 2 g of 2-bromo-5-fluoro-4-iodopyridine was added, and the mixture was stirred for 23 hours. After allowing to cool; the reaction solution was poured into a 12% aqueous ammonia solution, and the resultant solution was extracted with diethyl ether three times, washed with an aqueous saturated sodium chloride solution, dried with anhydrous magnesium sulfate, and concentrated. The residue was subjected to silica gel column chromatography to obtain 0.8 g of 2-bromo-5-fluoro-4-trifluoromethylpyridine.

2-Bromo-5-fluoro-4-trifluoromethylpyridine

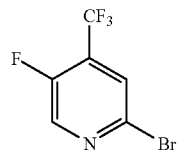

$^1$H-NMR: 7.71 (d, 1H), 8.45 (s, 1H)
$^{19}$F-NMR: −63.58 (d, 3H), −131.87-131.82 (m, 1H)

Reference Production Example 14

To 12 ml of N,N-dimethylformamide were added 0.8 g of 2-bromo-5-fluoro-4-trifluoromethylpyridine, 1.41 g of zinc cyanide and 0.28 g of tetrakistriphenylphosphinepalladium, and the mixture was stirred at 95° C. for 14 hours. After allowing to cool, the reaction solution was poured into water, and the resultant solution was extracted with diethyl ether three times, washed with an aqueous saturated sodium chloride solution, dried with anhydrous magnesium sulfate, and concentrated. The residue was subjected to silica gel column chromatography to obtain 0.5 g of 5-fluoro-4-trifluoromethylpyridine-2-carbonitrile.

5-Fluoro-4-trifluoromethylpyridine-2-carbonitrile

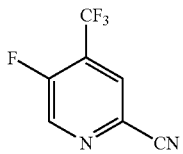

$^1$H-NMR: 7.96 (d, 1H), 8.79 (s, 1H)

Reference Production Example 15

To 12 ml of ethanol were added 1.01 g of sodium bicarbonate and 0.83 g of hydroxylamine hydrochloride, and the mixture was heated to reflux for 1 hour. After allowing to cool, 0.6 g of 5-fluoro-4-trifluoromethylpyridine-2-carbonitrile was added at 0° C., and the mixture was stirred for 2 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.4 g of 5-fluoro-4-trifluoromethylpyridine-2-carboxamide=oxime.

5-Fluoro-4-trifluoromethylpyridine-2-carboxamide=oxime

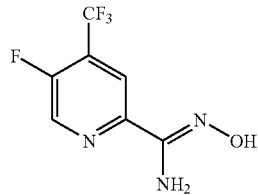

$^1$H-NMR (DMSO-$d_6$): 6.01 (s, 2H), 8.09 (d, 1H), 8.91 (s, 1H), 10.20 (s, 1H)

Reference Production Example 16

To 21 ml of toluene were added 1.9 g of 2-chloro-4-trifluoromethylpyridine, 1 g of cyclopropyl borate, 2.92 g of potassium carbonate and 0.26 g of [1,1′-bis(diphenylphosphino)ferrocene]dichloropalladium (II) dichloromethane complex (1:1), and the mixture was stirred at 100° C. for 10 hours. After allowing to cool, the reaction solution was poured into an aqueous saturated ammonium chloride solution, and the resultant solution was extracted with diethyl ether three times, washed with an aqueous saturated sodium chloride solution, dried with anhydrous magnesium sulfate, and concentrated. The residue was subjected to silica gel column chromatography to obtain 1 g of 2-cyclopropyl-4-trifluoromethylpyridine.

2-Cyclopropyl-4-trifluoromethylpyridine

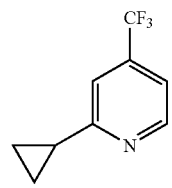

$^1$H-NMR: 0.97-1.05 (m, 4H), 2.25-2.32 (m, 1H), 7.47 (d, 1H), 7.71 (s, 1H), 8.66 (d, 1H)

Reference Production Example 17

To 10 ml of chloroform were added 1 g of 2-cyclopropyl-4-trifluoromethylpyridine, and 1.4 g of meta-chloroperbenzoic and, the mixture was stirred at 0° C. for 16 hours. Thereafter, the reaction solution was poured into an aqueous saturated sodium sulfite solution, followed by extraction with chloroform three times. The organic layers were combined, washed with an aqueous saturated sodium chloride solution, dried with anhydrous magnesium sulfate, and concentrated.

The residue was subjected to silica gel column chromatography to obtain 0.7 g of 2-cyclopropyl-4-trifluoromethylpyridine=N-oxide.

2-Cyclopropyl-4-trifluoromethylpyridine=N-oxide

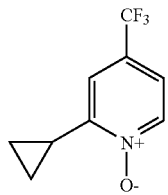

¹H-NMR: 0.82-0.87 (m, 2H), 1.23-1.28 (m, 2H), 2.67-2.74 (m, 1H), 7.09 (d, 1H), 7.30 (dd, 1H), 8.33 (d, 1H)

Reference Production Example 18

To 7 ml of acetonitrile were added 0.7 g of 2-cyclopropyl-4-trifluoromethylpyridine N-oxide, 0.96 ml of triethylamine, and 1 g of trimethylsilyl cyanide, and the mixture was heated to reflux for 20 hours. Thereafter, the reaction solution was allowed to cool to room temperature, and concentrated. The residue was subjected to silica gel column chromatography to obtain 0.6 g of 6-cyclopropyl-4-trifluoromethylpyridine-2-carbonitrile.

6-Cyclopropyl-4-trifluoromethylpyridine-2-carbonitrile

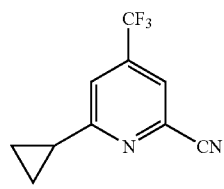

¹H-NMR: 1.13-1.21 (m, 4H), 2.11-2.17 (m, 1H), 7.59 (s, 1H), 7.61 (s, 1H)

Reference Production Example 19

To 7 ml of ethanol were added 0.58 g of sodium bicarbonate and 0.48 g of hydroxylamine hydrochloride, and the mixture was heated to reflux for 1 hour. After allowing to cool, 0.6 g of 6-cyclopropyl-4-trifluoromethylpyridine-2-carbonitrile was added at 0° C., and the mixture was stirred for 4 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.6 g of 6-cyclopropyl-4-trifluoromethylpyridine-2-carboxamide=oxime.

6-Cyclopropyl-4-trifluoromethylpyridine-2-carboxamide=oxime

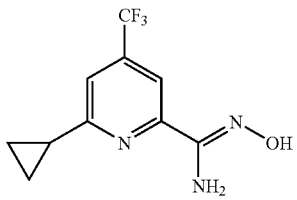

¹H-NMR (DMSO-d₆): 1.02-1.15 (m, 4H), 2.28-2.34 (m, 1H), 5.90 (s, 2H), 7.72 (s, 1H), 7.76 (s, 1H), 10.11 (s, 1H)

Reference Production Example 20

To 10 ml of N,N-dimethylformamide were added 1 g of 2-chloro-6-methyl-4-trifluoromethylpyridine, 1.2 g of zinc cyanide and 0.24 g of tetrakistriphenylphosphinepalladium, and the mixture was stirred at 90° C. for 10 hours. After allowing to cool, the reaction solution was poured into water, and the resultant solution was extracted with diethyl ether three times, washed with an aqueous saturated sodium chloride solution, dried with anhydrous magnesium sulfate, and concentrated. The residue was subjected to silica gel column chromatography to obtain 0.8 g of 6-methyl-4-trifluoromethylpyridine-2-carbonitrile.

6-Methyl-4-trifluoromethylpyridine-2-carbonitrile

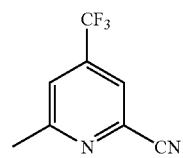

¹H-NMR: 2.72 (s, 3H), 7.60 (s, 1H), 7.72 (s, 1H)

Reference Production Example 21

To 10 ml of ethanol were added 0.86 g of sodium bicarbonate and 0.71 g of hydroxylamine hydrochloride, and the mixture was heated to reflux for 1 hour. After allowing to cool, 0.8 g of 6-methyl-4-trifluoromethylpyridine-2-carbonitrile was added at room temperature, and the mixture was stirred for 12 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.74 g of 6-methyl-4-trifluoromethylpyridine-2-carboxamide=oxime.

6-Methyl-4-trifluoromethylpyridine-2-carboxamide=oxime

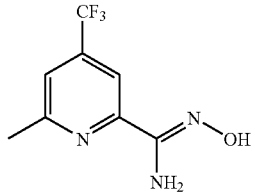

$^1$H-NMR (DMSO-$d_6$): 2.63 (s, 3H), 5.94 (s, 2H), 7.68 (s, 1H), 7.85 (s, 1H), 10.13 (s, 1H)

Reference Production Example 22

Into 7 ml of N,N-dimethylformamide was suspended 0.2 g of sodium hydride (60% oily), and 0.43 g of trifluoroethyl alcohol was added at 10° C. After stirring for 10 minutes, 0.5 g of 4-chloropyridine-2-carbonitrile was added, the mixture was stirred for 1 hour, and the reaction solution was poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.65 g of 4-(2,2,2-trifluoroethoxy)pyridine-2-carbonitrile.

4-(2,2,2-Trifluoroethoxy)pyridine-2-carbonitrile

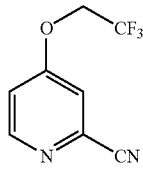

$^1$H-NMR: 4.47 (q, 2H), 7.07 (d, 1H), 7.30 (s, 1H), 8.61 (d, 1H)

Reference Production Example 23

To 6 ml of ethanol were added 0.54 g of sodium bicarbonate and 0.45 g of hydroxylamine hydrochloride, and the mixture was heated to reflux for 1 hour. After allowing to cool, 0.65 g of 4-(2,2,2-trifluoroethoxy)pyridine-2-carbonitrile was added at room temperature, and the mixture was stirred for 10 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was washed with hexane three times to obtain 0.7 g of 4-(2,2,2-trifluoroethoxy)pyridine-2-carboxamide=oxime.

4-(2,2,2-Trifluoroethoxy)pyridine-2-carboxamide=oxime

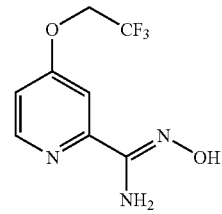

$^1$H-NMR (DMSO-$d_6$): 4.95 (q, 2H), 5.83 (s, 2H), 7.14 (dd, 1H), 7.42 (d, 1H), 8.45 (d, 1H), 9.91 (s, 1H)

Reference Production Example 24

Into 6 ml of N,N-dimethylformamide was suspended 0.16 g of sodium hydride (60% oily), and 0.52 g of 2,2,3,3,3-pentafluoro-1-propanol was added at 10° C. After stirring for 25 minutes, 0.4 g of 4-chloropyridine-2-carbonitrile was added, the mixture was stirred for 3 hours, and the reaction solution was poured into an aqueous saturated sodium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.55 g of 4-(2,2,3,3,3-pentafluoropropoxy)pyridine-2-carbonitrile.

4-(2,2,3,3,3-Pentafluoropropoxy)pyridine-2-carbonitrile

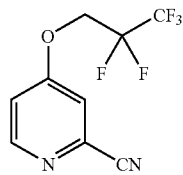

$^1$H-NMR: 4.53 (t, 2H), 7.08 (dd, 1H), 7.30 (d, 1H), 8.61 (d, 1H)

Reference Production Example 25

To 6 ml of ethanol were added 0.49 g of sodium bicarbonate and 0.4 g of hydroxylamine hydrochloride, and the mixture was heated to reflux for 1 hour. After allowing to cool, 0.55 g of 4-(2,2,3,3,3-pentafluoropropoxy)pyridine-2-carbonitrile was added at room temperature, and the mixture was stirred for 6 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated.

The residue was washed with hexane three times to obtain 0.6 g of 4-(2,2,3,3,3-pentafluoropropoxy)pyridine-2-carboxamide=oxime.

4-(2,2,3,3,3-Pentafluoropropoxy)pyridine-2-carboxamide=oxime

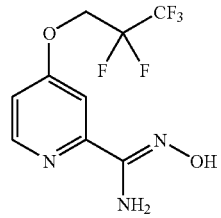

$^1$H-NMR (DMSO-$d_6$): 5.04 (t, 2H), 5.83 (s, 2H), 7.16 (dd, 1H), 7.44 (d, 1H), 8.45 (d, 1H), 9.90 (s, 1H)

Reference Production Example 26

Into 6 ml of N,N-dimethylformamide was suspended 0.16 g of sodium hydride (60% oily), and 0.4 g of 1,1,1-trifluoro-2-propanol was added at 10° C. After stirring for 40 minutes, 0.4 g of 4-chloropyridine-2-carbonitrile was added, the mixture was stirred for 2 hours, and the reaction solution was poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.49 g of 4-(2,2,2-trifluoro-1-methylethoxy)pyridine-2-carbonitrile.

4-(2,2,2-Trifluoro-1-methylethoxy)pyridine-2-carbonitrile

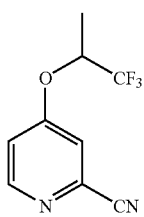

$^1$H-NMR: 1.60 (d, 3H), 4.88-4.98 (m, 1H), 7.14 (d, 1H), 7.34 (s, 1H), 8.59 (d, 1H)

Reference Production Example 27

To 4 ml of ethanol were added 0.38 g of sodium bicarbonate and 0.32 g of hydroxylamine hydrochloride, and the mixture was heated to reflux for 1 hour. After allowing to cool, 0.49 g of 4-(2,2,2-trifluoro-1-methylethoxy)pyridine-2-carbonitrile was added at room temperature, and the mixture was stirred for 8 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated.

The residue was washed with hexane three times to obtain 0.5 g of 4-(2,2,2-trifluoro-1-methylethoxy)pyridine-2-carboxamide=oxime.

4-(2,2,2-Trifluoro-1-methylethoxy)pyridine-2-carboxamide=oxime

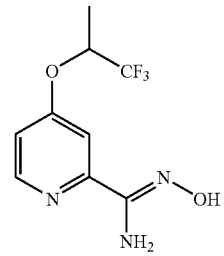

$^1$H-NMR (DMSO-$d_6$): 1.44 (d, 3H), 5.49-5.56 (m, 1H), 5.83 (s, 2H), 7.18 (dd, 1H), 7.43 (d, 1H), 8.44 (d, 1H), 9.91 (s, 1H)

Reference Production Example 28

Into 8 ml of N,N-dimethylformamide was suspended 0.22 g of sodium hydride (60% oily), and 0.47 g of trifluoroethyl alcohol was added at 10° C. After stirring for 10 minutes, 0.6 g of 4-chloro-6-methylpyridine-2-carbonitrile was added at 0° C., the mixture was stirred for 1 hour, and the reaction solution was poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.79 g of 6-methyl-4-(2,2,2-trifluoroethoxy)pyridine-2-carbonitrile.

6-Methyl-4-(2,2,2-trifluoroethoxy)pyridine-2-carbonitrile

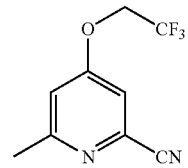

$^1$H-NMR: 2.59 (s, 3H), 4.43 (q, 2H), 6.91 (d, 1H), 7.12 (d, 1H)

Reference Production Example 29

To 6 ml of ethanol were added 0.54 g of sodium bicarbonate and 0.44 g of hydroxylamine hydrochloride, and the mixture was heated to reflux for 1 hour. After allowing to cool, 0.69 g of 6-methyl-4-(2,2,2-trifluoroethoxy)pyridine-2-carbonitrile was added at room temperature, and the mixture was stirred for 2 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was washed with hexane three times to obtain 0.76 g of 6-methyl-4-(2,2,2-trifluoroethoxy)pyridine-2-carboxamide=oxime.

6-Methyl-4-(2,2,2-trifluoroethoxy)pyridine-2-carboxamide=oxime

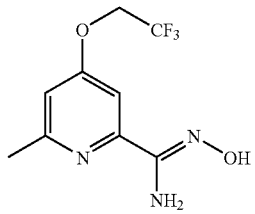

$^1$H-NMR (DMSO-d$_6$): 2.47 (s, 3H), 4.91 (q, 2H), 5.78 (s, 2H), 7.02 (d, 1H), 7.24 (d, 1H), 9.86 (s, 1H)

Reference Production Example 30

Into 6 ml of N,N-dimethylformamide was suspended 0.18 g of sodium hydride (60% oily), and 0.44 g of 1,1,1-trifluoro-2-propanol was added at 10° C. After stirring for 10 minutes, 0.49 g of 4-chloro-6-methylpyridine-2-carbonitrile was added, the mixture was stirred for 1 hour, and the reaction solution was poured into an aqueous saturated ammonium chloride solution, followed by extraction with tert-butyl=methyl=ether. The organic layers were combined, washed with an aqueous saturated sodium chloride solution, dried with anhydrous magnesium sulfate, and concentrated. The residue was subjected to silica gel column chromatography to obtain 0.72 g of 6-methyl-4-(2,2,2-trifluoro-1-methylethoxy)pyridine-2-carbonitrile.

6-Methyl-4-(2,2,2-trifluoro-1-methylethoxy)pyridine-2-carbonitrile

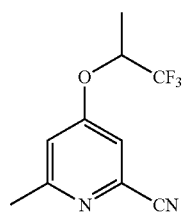

$^1$H-NMR: 1.56 (d, 3H), 2.57 (s, 3H), 4.76-4.82 (m, 1H), 6.91 (d, 1H), 7.10 (d, 1H)

Reference Production Example 31

To 6 ml of ethanol were added 0.53 g of sodium bicarbonate and 0.44 g of hydroxylamine hydrochloride, and the mixture was heated to reflux for 1 hour. After allowing to cool, 0.72 g of 6-methyl-4-(2,2,2-trifluoro-1-methylethoxy)pyridine-2-carbonitrile was added at room temperature, and the mixture was stirred for 8 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was washed with hexane three times to obtain 0.73 g of 6-methyl-4-(2,2,2-trifluoro-1-methylethoxy)pyridine-2-carboxamide=oxime.

6-Methyl-4-(2,2,2-trifluoro-1-methylethoxy)pyridine-2-carboxamide=oxime

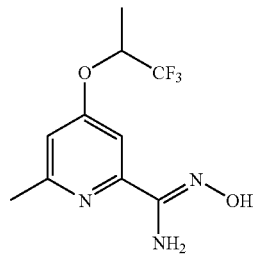

$^1$H-NMR (DMSO-d$_6$): 1.43 (d, 3H), 2.46 (s, 3H), 5.44-5.50 (m, 1H), 5.78 (s, 2H), 7.05 (d, 1H), 7.25 (d, 1H), 9.86 (s, 1H)

Reference Production Example 32

To 10 ml of dichloroethane were added 1.36 g of zirconium tetrachloride and 1 g of 4-methylbenzoyl chloride, and the mixture was stirred at room temperature for 20 minutes. The mixture was cooled to 0° C., 0.22 g of trioxane was added, and the mixture was stirred at room temperature for 1 hour. Water was added slowly at 0° C., the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 0.7 g of chloromethyl 4-methylbenzoate.

Chloromethyl 4-methylbenzoate

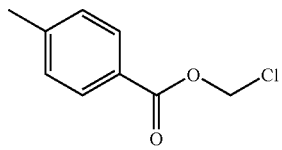

$^1$H-NMR: 2.43 (s, 3H), 5.95 (s, 2H), 7.27 (d, 2H), 7.79 (d, 2H)

Reference Production Example 33

To 10 ml of dichloroethane were added 1.1 g of zirconium tetrachloride and 1 g of 4-t-butylbenzoyl chloride, and the mixture was stirred at room temperature for 20 minutes. The mixture was cooled to 0° C., 0.19 g of trioxane was added, and the mixture was stirred at room temperature for 1 hour. Water was added slowly at 0° C., the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 0.65 g of chloromethyl 4-t-butylbenzoate.

Chloromethyl 4-t-butylbenzoate

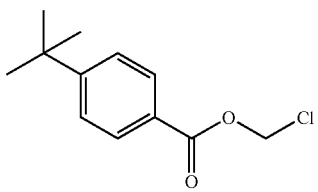

$^1$H-NMR: 1.35 (s, 9H), 5.95 (s, 2H), 7.49 (d, 2H), 8.01 (d, 2H)

Reference Production Example 34

To 10 ml of dichloroethane were added 1.32 g of zirconium tetrachloride and 1 g of 3-fluorobenzoyl chloride, and the mixture was stirred at room temperature for 20 minutes. The mixture was cooled to 0° C., 0.21 g of trioxane was added, and the mixture was stirred for 1 hour, and further stirred at room temperature for 1 hour. Water was added slowly at 0° C., the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 0.65 g of chloromethyl 3-fluorobenzoate.

Chloromethyl 3-fluorobenzoate

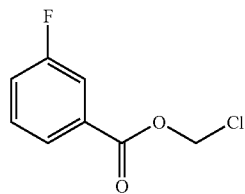

$^1$H-NMR: 5.95 (s, 2H), 7.33 (tdd, 1H), 7.46 (td, 2H), 7.76 (ddd, 1H), 7.88 (td, 1H)

Reference Production Example 35

To 10 ml of dichloroethane were added 1.32 g of zirconium tetrachloride and 1 g of 4-fluorobenzoyl chloride, and the mixture was stirred at room temperature for 20 minutes. The mixture was cooled to 0° C., 0.21 g of trioxane was added, and the mixture was stirred for 1 hour, and further stirred at room temperature for 1 hour. Water was added slowly at 0° C., the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 0.89 g of chloromethyl 4-fluorobenzoate.

Chloromethyl 4-fluorobenzoate

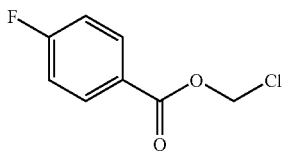

$^1$H-NMR: 5.95 (s, 2H), 7.15 (t, 2H), 8.11 (dd, 2H)

Reference Production Example 36

To 10 ml of dichloroethane were added 1 g of zirconium tetrachloride and 1 g of 3,5-dichlorobenzoyl chloride, and the mixture was stirred at room temperature for 15 minutes. The mixture was cooled to 0° C., 0.16 g of trioxane was added, and the mixture was stirred for 1 hour, and further stirred at room temperature for 2 hours. Water was added slowly at 0° C., the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated. The residue was subjected to silica gel chromatography to obtain 1 g of chloromethyl 3,5-dichlorobenzoate.

Chloromethyl 3,5-dichlorobenzoate

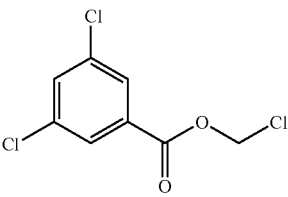

$^1$H-NMR: 5.94 (s, 2H), 7.67 (t, 1H), 7.99 (d, 2H)

Reference Production Example 37

To 10 ml of dichloroethane were added 1.2 g of zirconium tetrachloride and 1 g of 3,5-difluorobenzoyl chloride, and the mixture was stirred at room temperature for 15 minutes. The mixture was cooled to 0° C., 0.19 g of trioxane was added, and the mixture was stirred for 10 minutes, and further stirred at room temperature for 1 hour. Water was added slowly at 0° C., the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 1 g of chloromethyl 3,5-difluorobenzoate.

Chloromethyl 3,5-difluorobenzoate

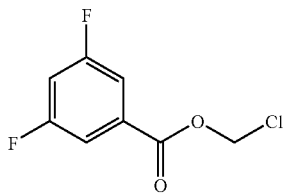

¹H-NMR: 5.94 (s, 2H), 7.08 (tt, 1H), 7.57-7.63 (m, 1H)

Reference Production Example 38

To 10 ml of dichloroethane were added 1 g of zirconium tetrachloride and 1 g of 3,4-dichlorobenzoyl chloride, and the mixture was stirred at room temperature for 15 minutes. The mixture was cooled to 0° C., 0.16 g of trioxane was added, and the mixture was stirred for 10 minutes, and further stirred at room temperature for 1 hour. Water was added slowly at 0° C., the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 0.85 g of chloromethyl 3,4-dichlorobenzoate.

Chloromethyl 3,4-dichlorobenzoate

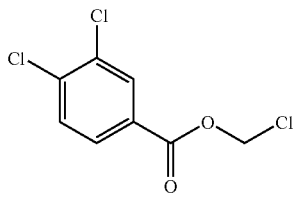

¹H-NMR: 5.94 (s, 2H), 7.57 (d, 1H), 7.91 (dd, 1H), 8.16 (d, 1H)

Reference Production Example 39

To 10 ml of dichloroethane were added 1.2 g of zirconium tetrachloride and 1 g of 3,4-difluorobenzoyl chloride, and the mixture was stirred at room temperature for 30 minutes. The mixture was cooled to 0° C., 0.19 g of trioxane was added, and the mixture was stirred for 30 minutes, and further stirred at room temperature for 1 hour. Water was added slowly at 0° C., the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 1.1 g of chloromethyl 3,4-difluorobenzoate.

Chloromethyl 3,4-difluorobenzoate

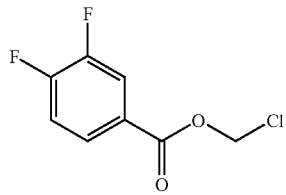

¹H-NMR: 5.94 (s, 2H), 7.24-7.30 (m, 1H), 7.86-7.93 (m, 2H)

Reference Production Example 40

To 10 ml of dichloroethane were added 1 g of zirconium tetrachloride and 1 g of 4-trifluoromethylbenzoyl chloride, and the mixture was stirred at room temperature for 30 minutes. The mixture was cooled to 10° C., 0.16 g of trioxane was added, and the mixture was stirred for 30 minutes, and further stirred at room temperature for 1 hour. The mixture was cooled to 0° C., water was added slowly, the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 0.92 g of chloromethyl 4-trifluoromethylbenzoate.

Chloromethyl 4-trifluoromethylbenzoate

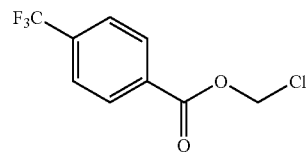

¹H-NMR: 5.98 (s, 2H), 7.75 (d, 2H), 8.20 (d, 2H)

Reference Production Example 41

To 10 ml of dichloroethane were added 1 g of zirconium tetrachloride and 1 g of 3-trifluoromethylbenzoyl chloride, and the mixture was stirred at room temperature for 30 minutes. At 10° C., 0.16 g of trioxane was added, and the mixture was stirred for 30 minutes, and further stirred at room temperature for 2 hours. The mixture was cooled to 0° C., water was added slowly, the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated.

The residue was subjected to silica gel column chromatography to obtain 0.4 g of chloromethyl 3-trifluoromethylbenzoate.

Chloromethyl 3-trifluoromethylbenzoate

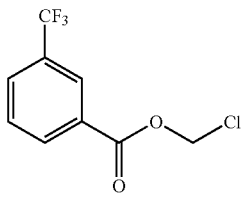

¹H-NMR: 5.90 (s, 2H), 7.64 (t, 1H), 7.88 (d, 1H), 8.28 (d, 1H), 8.35 (s, 1H)

Reference Production Example 42

To 10 ml of dichloroethane were added 0.93 g of zirconium tetrachloride and 1 g of 3-trifluoromethoxybenzoyl chloride, and the mixture was stirred at room temperature for 20 minutes. At 10° C., 0.15 g of trioxane was added, and the mixture was stirred for 30 minutes, and further stirred at room temperature for 1 hour. Water was added slowly under ice-cooling, the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 1 g of chloromethyl 3-trifluoromethoxybenzoate.

Chloromethyl 3-trifluoromethoxybenzoate

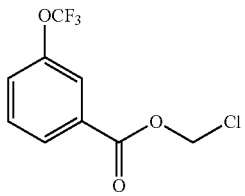

¹H-NMR: 5.96 (s, 2H), 7.47-7.55 (m, 2H), 7.93 (s, 1H), 8.03 (d, 1H)

Reference Production Example 43

To 10 ml of dichloroethane were added 0.96 g of zirconium tetrachloride and 1 g of 3-bromobenzoyl chloride, and the mixture was stirred at room temperature for 20 minutes. At 10° C., 0.15 g of trioxane was added, and the mixture was stirred for 10 minutes, and further stirred at room temperature for 2 hours. Water was added slowly under ice-cooling, the resultant solution was extracted with chloroform three times, and the organic layers were combined, washed with an aqueous saturated sodium bicarbonate solution and an aqueous saturated sodium chloride solution, dried with anhydrous magnesium sulfate, and concentrated to obtain 0.95 g of chloromethyl 3-bromobenzoate.

Chloromethyl 3-bromobenzoate

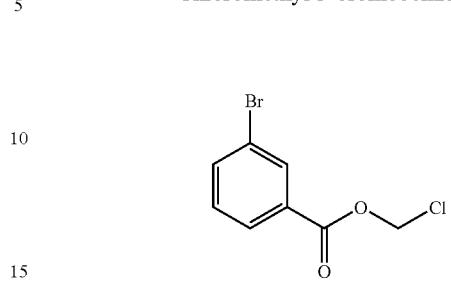

¹H-NMR: 5.95 (s, 2H), 7.36 (t, 1H), 7.75 (d, 1H), 8.02 (dt, 1H), 8.22 (t, 1H)

Reference Production Example 44

Into 5 ml of tetrahydrofuran was suspended 0.12 g of sodium hydride (60% oily), and 0.27 g of trifluoroethyl alcohol was added at 10° C. After stirring for 10 minutes, 0.5 g of 3,4,5-trichloropyridine-2-carbonitrile was added at 0° C., the mixture was stirred for 20 hours, and the reaction solution was poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.6 g of 3,5-dichloro-4-(2,2,2-trifluoroethoxy)pyridine-2-carbonitrile. 3,5-Dichloro-4-(2,2,2-trifluoroethoxy)pyridine-2-carbonitrile

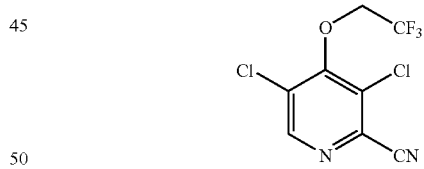

¹H-NMR: 4.62 (q, 2H), 8.58 (s, 1H)

Reference Production Example 45

To 5 ml of ethanol were added 0.41 g of sodium bicarbonate and 0.34 g of hydroxylamine hydrochloride, and the mixture was heated to reflux for 1 hour. After allowing to cool, 0.6 g of 3,5-dichloro-4-(2,2,2-trifluoroethoxy)pyridine-2-carbonitrile was added at room temperature, and the mixture was stirred for 2 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated.

The residue was washed with hexane three times to obtain 0.64 g of 3,5-dichloro-4-(2,2,2-trifluoroethoxy)pyridine-2-carboxamide=oxime.

3,5-Dichloro-4-(2,2,2-trifluoroethoxy)pyridine-2-carboxamide=oxime

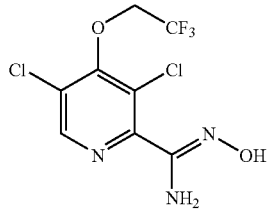

$^1$H-NMR (DMSO-$d_6$): 4.95 (q, 2H), 5.87 (s, 2H), 8.69 (s, 1H), 9.91 (s, 1H)

Reference Production Example 46

Into 5 ml of tetrahydrofuran was suspended 0.12 g of sodium hydride (60% oily), and 0.3 g of 1,1,1-trifluoro-2-propanol was added at 10° C. After stirring for 10 minutes, 0.5 g of 3,4,5-trichloropyridine-2-carbonitrile was added, the mixture was stirred for 1 hour, and the reaction solution was poured into an aqueous saturated ammonium chloride solution, followed by extraction with tert-butyl=methyl=ether three times. The organic layers were combined, washed with an aqueous saturated sodium chloride solution, dried with anhydrous magnesium sulfate, and concentrated. The residue was subjected to silica gel column chromatography to obtain 0.67 g of 3,5-dichloro-4-(2,2,2-trifluoro-1-methylethoxy)pyridine-2-carbonitrile.

3,5-Dichloro-4-(2,2,2-trifluoro-1-methylethoxy)pyridine-2-carbonitrile

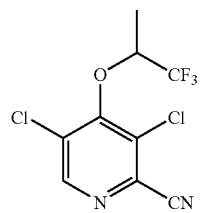

$^1$H-NMR: 1.65 (d, 3H), 4.94-5.00 (m, 1H), 8.56 (s, 1H)

Reference Production Example 47

To 5 ml of ethanol were added 0.4 g of sodium bicarbonate and 0.33 g of hydroxylamine hydrochloride, and the mixture was heated to reflux for 1 hour. After allowing to cool, 0.67 g of 3,5-dichloro-4-(2,2,2-trifluoro-1-methylethoxy)pyridine-2-carbonitrile at room temperature, and the mixture was stirred for 4 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated.

The residue was washed with hexane three times to obtain 0.65 g of 3,5-dichloro-4-(2,2,2-trifluoro-1-methylethoxy)pyridine-2-carboxamide=oxime.

3,5-Dichloro-4-(2,2,2-trifluoro-1-methylethoxy)pyridine-2-carboxamide=oxime

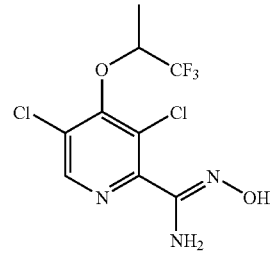

$^1$H-NMR (DMSO-$d_6$): 1.53 (d, 3H), 5.22-5.28 (m, 1H), 5.88 (s, 2H), 8.69 (s, 1H), 9.85 (s, 1H)

Reference Production Example 48

To 60 ml of tetrahydrofuran were added 4.98 ml of trifluoromethyltrimethylsilane and 3 g of isonicotinealdehyde, and 0.09 g of tetrabutylammonium fluoride trihydrate was added at 0° C., and the mixture was stirred for 1 hour. Thereafter, 10% hydrochloric acid was added at 0° C., and the mixture was stirred for 3 hours, and poured into an aqueous saturated sodium bicarbonate solution. After extraction with ethyl acetate three times, the organic layers were combined, washed with an aqueous saturated sodium chloride solution, dried with anhydrous magnesium sulfate, and concentrated. The residue was subjected to silica gel column chromatography to obtain 4.7 g of 2,2,2-trifluoro-1-pyridin-4-yl-ethanol.

2,2,2-Trifluoro-1-pyridin-4-yl-ethanol $^1$H-NMR: 4.34 (brs, 1H), 5.07 (brs, 1H), 7.46 (d, 2H), 8.62 (d, 2H)

Reference Production Example 49

To 20 ml of pyridine were added 3.4 g of 2,2,2-trifluoro-1-pyridin-4-yl-ethanol and 1.17 g of 4-dimethylaminopyridine, and 3.76 g of triethylsilyl chloride was added at 0° C. After stirring at room temperature for 4 hours, the mixture was poured into an aqueous saturated ammonium chloride solution, followed by extraction with t-butyl methyl ether three times. The organic layers were combined, washed with an aqueous saturated sodium chloride solution, dried with anhydrous magnesium sulfate, and concentrated. The residue was subjected to silica gel column chromatography to obtain 5.5 g of 4-[2,2,2-trifluoro-1-(triethylsilyloxy)ethyl]pyridine.

4-[2,2,2-Trifluoro-1-(triethylsilyloxy)ethyl]pyridine

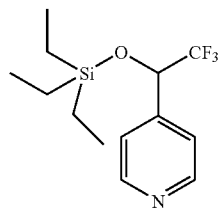

$^1$H-NMR: 0.56-0.67 (m, 6H), 0.91 (t, 9H), 4.92 (q, 1H), 7.39 (d, 2H), 8.65 (d, 2H)

Reference Production Example 50

To 40 ml of chloroform were added 5.5 g of 4-[2,2,2-trifluoro-1-(triethylsilyloxy)ethyl]pyridine, and 7.5 g of meta-chloroperbenzoic acid, and the mixture was stirred at 0° C. for 2 hours, and at room temperature for 3 hours. Thereafter, the reaction solution was poured into an aqueous saturated sodium sulfite solution, followed by extraction with chloroform three times. The organic layers were combined, washed with an aqueous saturated sodium chloride solution, dried with anhydrous magnesium sulfate, and concentrated. The residue was subjected to silica gel column chromatography to obtain 5 g of 4-[2,2,2-trifluoro-1-(triethylsilyloxy)ethyl]pyridine N-oxide.

4-[2,2,2-Trifluoro-1-(triethylsilyloxy)ethyl]pyridine N-oxide

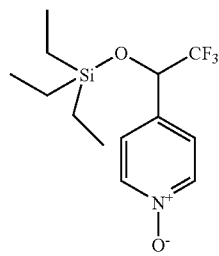

$^1$H-NMR: 0.59-0.67 (m, 6H), 0.92 (t, 9H), 4.91 (q, 1H), 7.38 (d, 2H), 8.21-8.24 (m, 2H)

Reference Production Example 51

To 40 ml of acetonitrile were added 5 g of 4-[2,2,2-trifluoro-1-(triethylsilyloxy)ethyl]pyridine N-oxide, 5.26 ml of triethylamine, and 5.62 g of trimethylsilyl cyanide, and the mixture was stirred at 90° C. for 20 hours. Thereafter, the reaction solution was allowed to cool to room temperature, and concentrated. The residue was subjected to silica gel column chromatography to obtain 3 g of 4-[2,2,2-trifluoro-1-(triethylsilyloxy)ethyl]pyridine-2-carbonitrile.

4-[2,2,2-Trifluoro-1-(triethylsilyloxy)ethyl]pyridine-2-carbonitrile

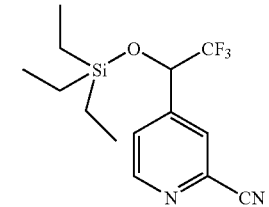

$^1$H-NMR: 0.57-0.68 (m, 6H), 0.97 (t, 9H), 4.99 (q, 1H), 7.62 (d, 1H), 7.81 (s, 1H), 8.76 (d, 1H)

Reference Production Example 52

To 4 ml of ethanol were added 0.24 g of sodium bicarbonate and 0.2 g of hydroxylamine hydrochloride, and the mixture was heated to reflux for 1 hour. After allowing to cool, 0.6 g of 4-[2,2,2-trifluoro-1-(triethylsilyloxy)ethyl]pyridne-2-carbonitrile was added at 0° C., and the mixture was stirred for 4 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.6 g of 4-[2,2,2-trifluoro-1-(triethylsilyloxy)ethyl]pyridine-2-carboxamide=oxime.

4-[2,2,2-Trifluoro-1-(triethylsilyloxy)ethyl]pyridine-2-carboxamide=oxime

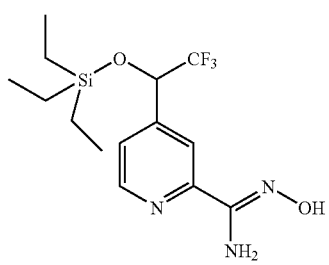

$^1$H-NMR (DMSO-d$_6$): 0.53-0.66 (m, 6H), 0.84 (t, 9H), 5.63 (q, 1H), 5.89 (s, 2H), 7.54 (d, 1H), 8.05 (s, 1H), 8.63 (d, 1H), 10.00 (s, 1H)

Reference Production Example 53

To 40 ml of tetrahydrofuran was added 12 g of 4-[2,2,2-trifluoro-1-(triethylsilyloxy)ethyl]pyridine-2-carbonitrile, and 15 ml of tetrabutylammonium fluoride (1M tetrahydrofuran solution) was added at 0° C. After the mixture was stirred at room temperature for 5 hours, water was added to the reaction solution, the resultant solution was extracted with ethyl acetate three times, and the organic layers were combined, dried with anhydrous magnesium sulfate, and concentrated. The residue was subjected to silica gel column chromatography to obtain 5.6 g of 4-(2,2,2-trifluoro-1-hydroxyethyl)pyridine-2-carbonitrile.

4-(2,2,2-trifluoro-1-hydroxyethyl)pyridine-2-carbonitrile

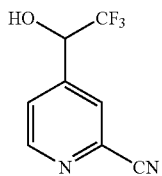

$^1$H-NMR: 3.84 (bs, 1H), 5.12-5.18 (m, 1H), 7.69 (d, 1H), 7.89 (s, 1H), 8.78 (d, 1H)

Reference Production Example 54

To 4 ml of dimethylformamide were added 0.4 g of 4-(2,2,2-trifluoro-1-hydroxyethyl)pyridine-2-carbonitrile, 0.33 g of potassium carbonate and 0.34 g of methyl iodide, and the mixture was stirred at room temperature for 20 hours. Thereafter, an aqueous saturated ammonium chloride solution was added to the reaction solution, the resultant solution was extracted with ethyl acetate three times, the organic layers were combined, dried with anhydrous magnesium sulfate, and concentrated. The residue was subjected to silica gel column chromatography to obtain 0.2 g of 4-(2,2,2-trifluoro-1-methoxyethyl)pyridine-2-carbonitrile.

4-(2,2,2-Trifluoro-1-methoxyethyl)pyridine-2-carbonitrile

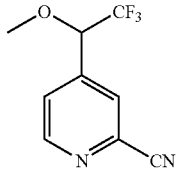

$^1$H-NMR: 3.56 (s, 3H), 4.58 (q, 1H), 7.60 (d, 1H), 7.79 (s, 1H), 8.79 (d, 1H)

Reference Production Example 55

To 2 ml of ethanol were added 0.12 g of sodium bicarbonate and 0.1 g of hydroxylamine hydrochloride, and the mixture was heated to reflux for 1 hour. After allowing to cool, 0.2 g of 4-(2,2,2-thfluoro-1-methoxyethyl)pyridine-2-carbonitrile was added at 0° C., and the mixture was stirred for 3 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.15 g of 4-(2,2,2-trifluoro-1-methoxyethyl)pyridine-2-carboxamide=oxime.

4-(2,2,2-Trifluoro-1-methoxyethyl)pyridine-2-carboxamide=oxime

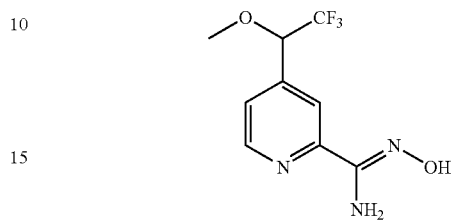

$^1$H-NMR (DMSO-d$_6$): 3.40 (s, 3H), 5.30 (q, 1H), 5.90 (s, 2H), 7.48 (d, 1H), 7.96 (s, 1H), 8.66 (d, 1H), 10.00 (s, 1H)

Reference Production Example 56

To 5 ml of dimethylformamide were added 0.5 g of 4-(2,2,2-trifluoro-1-hydroxyethyl)pyridine-2-carbonitrile, 0.45 g of potassium carbonate and 0.39 g of 3-bromo-1-propene, and the mixture was stirred at room temperature for 20 hours. Thereafter, an aqueous saturated ammonium chloride solution was added to the reaction solution, the resultant solution was extracted with ethyl acetate, and the organic layers were combined, dried with anhydrous magnesium sulfate, and concentrated. The residue was subjected to silica gel column chromatography to obtain 0.17 g of 4-[2,2,2-trifluoro-1-(2-propenyloxy)ethyl]pyridine-2-carbonitrile.

4-[2,2,2-Trifluoro-1-(2-propenyloxy)ethyl]pyridine-2-carbonitrile

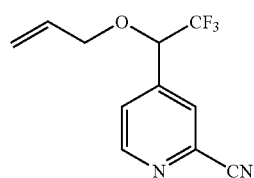

$^1$H-NMR: 4.12-4.23 (m, 2H), 4.74 (q, 1H), 5.30 (s, 1H), 5.34 (dd, 1H), 5.82-5.92 (m, 1H), 7.61 (d, 1H), 7.80 (s, 1H), 8.78 (d, 1H)

Reference Production Example 57

Copper iodide (0.91 g) and potassium fluoride (0.3 g) were subjected to a reduced pressure (1 Torr) using a vacuum pump, and were heated with a heat gun for 20 minutes while stirring slowly. Under the argon atmosphere, 8 ml of N-methylpyrrolidine and 1 g of pentafluoroethyltrimethylsilane were added at room temperature, and a temperature was elevated to 50° C. over 30 minutes. After further stirring for 1 hour, 1 g of 4-iodopyridine-2-carbonitrile was added, and the mixture was stirred for 20 hours. After allowing to cool, the reaction solution was poured into a 12% aqueous ammonia solution, the resultant solution was extracted with diethyl ether three times, and this was washed with an aqueous saturated sodium chloride solution, dried with anhydrous magnesium sulfate, and concentrated. The crude product was used in the next reaction without purification.

To 8 ml of ethanol were added 0.55 g of sodium bicarbonate and 0.45 g of hydroxylamine hydrochloride, and the mixture was heated to reflux for 1 hour. After allowing to cool, the crude product was added at 0° C., and the mixture was stirred for 3 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.9 g of 4-pentafluoroethylpyridine-2-carboxamide=oxime.

4-Pentafluoroethylpyridine-2-carboxamide=oxime

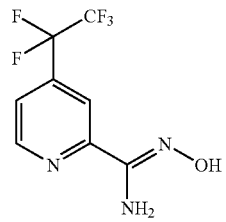

$^1$H-NMR (DMSO-$d_6$): 6.03 (s, 2H), 7.78 (d, 1H), 8.05 (s, 1H), 8.88 (d, 1H), 10.22 (s, 1H)

Reference Production Example 58

To 5 ml of acetonitrile were added 1 g of 4-(2,2,2-trifluoro-1-hydroxyethyl)pyridine-2-carbonitrile, 1 ml of pyridine and 0.12 g of N,N-dimethylaminopyridine, subsequently, 1.2 g of phenyl chlorothionoformate was added dropwise at room temperature. After stirring for 7 hours, water was added to the reaction solution, the resultant solution was extracted with ethyl acetate three times, and the organic layers were combined, and dried with anhydrous magnesium sulfate. After concentration, the crude product was used in the next reaction without purification.

To 10 ml of toluene were added 1.73 g of tri-n-butyltin=hydride, 0.16 g of azobisisobutyronitrile, and the crude product, and the mixture was heated to reflux for 2 hours. After allowing to cool, this was poured into an aqueous potassium fluoride solution, the resultant solution was extracted with diethyl ether three times, washed with an aqueous saturated sodium chloride solution, dried with anhydrous magnesium sulfate, and concentrated. The residue was subjected to silica gel column chromatography to obtain 0.3 g of 4-(2,2,2-trifluoroethyl)pyridine-2-carbonitrile.

4-(2,2,2-Trifluoroethyl)pyridine-2-carbonitrile

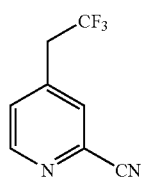

$^1$H-NMR: 3.48 (q, 2H), 7.49 (d, 1H), 7.67 (s, 1H), 8.74 (d, 1H)

Reference Production Example 59

To 3 ml of ethanol were added 0.2 g of sodium bicarbonate and 0.17 g of hydroxylamine hydrochloride, and the mixture was heated to reflux for 1 hour. After allowing to cool, 0.3 g of 4-(2,2,2-trifluoroethyl)pyridine-2-carbonitrile was added at 0° C., and the mixture was stirred for 4 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.3 g of 4-(2,2,2-trifluoroethyl)pyridine-2-carboxamide=oxime.

4-(2,2,2-Trifluoroethyl)pyridine-2-carboxamide=oxime

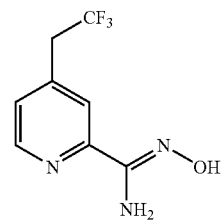

$^1$H-NMR (DMSO-$d_6$): 3.82 (q, 2H), 5.86 (s, 2H), 7.41 (d, 1H), 7.88 (s, 1H), 8.57 (d, 1H), 9.97 (s, 1H)

Reference Production Example 60

To 34 ml of toluene were added 3.13 ml of trifluoromethyltrimethylsilane and 2.13 g of 4-acetylpyridine, 0.27 g of tetrabutylammonium acetate was added at 0° C., and the mixture was stirred for 2 hours. Thereafter, this was poured into an aqueous saturated ammonium chloride solution. After extraction with t-butyl=methyl=ether three times, the organic layers were combined, washed with an aqueous saturated sodium chloride solution, dried with anhydrous magnesium sulfate, and concentrated. The residue was subjected to silica gel column chromatography to obtain 4.2 g of 4-[2,2,2-trifluoro-1-methyl-1-(trimethylsilyloxy)ethyl]pyridine.

4-[2,2,2-Trifluoro-1-methyl-1-(trimethylsilyloxy) ethyl]pyridine

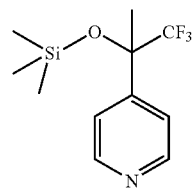

$^1$H-NMR: 0.19 (s, 9H), 1.81 (s, 3H), 7.44 (d, 2H), 8.64 (d, 2H)

Reference Production Example 61

To 30 ml of chloroform were added 4.2 g of 4-[2,2,2-trifluoro-1-methyl-1-(trimethylsilyloxy)ethyl]pyridine and 5.4 g of meta-chloroperbenzoic acid, and the mixture was stirred at 0° C. for 2 hours, and at room temperature for 6 hours. Thereafter, the reaction solution was poured into an aqueous saturated sodium sulfite solution, followed by extraction with chloroform three times. The organic layers were combined, washed with an aqueous saturated sodium chloride solution, dried with anhydrous magnesium sulfate, and concentrated. The residue was subjected to silica gel column chromatography to obtain 4 g of 4-[2,2,2-trifluoro-1-methyl-1-(trimethylsilyloxy)ethyl]pyridine=N-oxide.

4-[2,2,2-Trifluoro-1-methyl-1-(trimethylsilyloxy)ethyl]pyridine=N-oxide

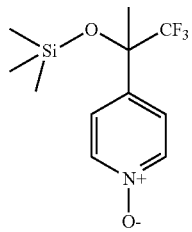

$^1$H-NMR: 0.21 (s, 9H), 1.80 (s, 3H), 7.42 (d, 2H), 8.21 (d, 2H)

Reference Production Example 62

To 30 ml of acetonitrile were added 4 g of 4-[2,2,2-trifluoro-1-methyl-1-(trimethylsilyloxy)ethyl]pyridine=N-oxide, 4.45 ml of triethylamine, and 4.75 g of trimethylsilyl cyanide, and the mixture was stirred at 90° C. for 20 hours. Thereafter, the reaction solution was allowed to cool to room temperature, and concentrated. The residue was subjected to silica gel column chromatography to obtain 4.3 g of 4-[2,2,2-trifluoro-1-methyl-1-(trimethylsilyloxy)ethyl]pyridine-2-carbonitrile.

4-[2,2,2-Trifluoro-1-methyl-1-(trimethylsilyloxy)ethyl]pyridine-2-carbonitrile

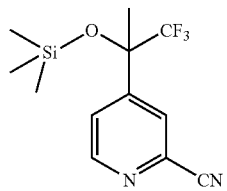

$^1$H-NMR: 0.23 (s, 9H), 1.82 (s, 3H), 7.66 (d, 1H), 7.85 (s, 1H), 8.75 (d, 1H)

Reference Production Example 63

To 4 ml of ethanol were added 0.22 g of sodium bicarbonate and 0.18 g of hydroxylamine hydrochloride, and the mixture was heated to reflux for 1 hour. After allowing to cool, 0.5 g of 4-[2,2,2-trifluoro-1-methyl-1-(trimethylsilyloxy)ethyl]pyridine-2-carbonitrile was added at 0° C., and the mixture was stirred for 2 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.5 g of 4-[2,2,2-trifluoro-1-methyl-1-(trimethylsilyloxy)ethyl]pyridine-2-carboxamide=oxime.

4-[2,2,2-Trifluoro-1-methyl-1-(trimethylsilyloxy)ethyl]pyridine-2-carboxamide=oxime

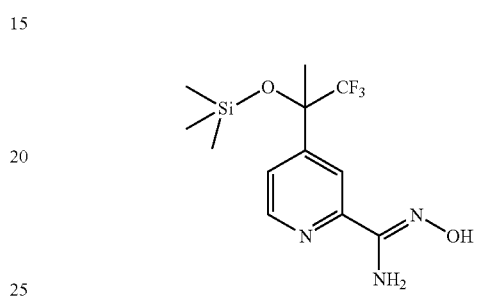

$^1$H-NMR (DMSO-$d_6$): 0.15 (s, 9H), 1.85 (s, 3H), 5.90 (s, 2H), 7.57 (d, 1H), 8.06 (s, 1H), 8.63 (d, 1H), 10.01 (s, 1H)

Reference Production Example 64

To 1,4-dioxane were added 3.22 g of 4-iodopyridine, 10.87 g of potassium carbonate, 0.036 g of tetrakis(triphenylphosphinepalladium) and 5.5 g of 1-(trifluoromethyl)vinylboronic acid, and the mixture was stirred at 110° C. for 8 hours. Thereafter, this solution was poured into an aqueous saturated ammonium chloride solution, followed by extraction with diethyl ether three times. The organic layers were combined, washed with an aqueous saturated sodium chloride solution, dried with anhydrous magnesium sulfate, and concentrated. The residue was subjected to silica gel column chromatography to obtain 2.0 g of 4-[1-(trifluoromethyl)ethenyl]pyridine.

4-[1-(Trifluoromethyl)ethenyl]pyridine

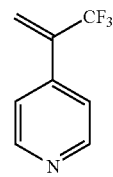

$^1$H-NMR: 5.98 (s, 1H), 6.12 (s, 1H), 7.37 (d, 2H), 8.66 (d, 2H)

Reference Production Example 65

To 20 ml of ethyl acetate were added 1.5 g of 4-[1-(trifluoromethyl)ethenyl]pyridine and 0.15 g of 10% Pd/C, and the mixture was stirred under the hydrogen atmosphere for 7 hours. The mixture was filtered, the filtrate was concentrated, and the residue was subjected to silica gel column chromatography to obtain 1.3 g of 4-(2,2,2-trifluoro-1-methyl-ethyl)pyridine.

4-(2,2,2-Trifluoro-1-methyl-ethyl)pyridine

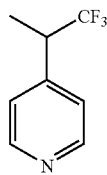

$^1$H-NMR: 1.52 (d, 3H), 3.37-3.49 (m, 1H), 7.25 (d, 2H), 8.60-8.62 (m, 2H)

Reference Production Example 66

To 15 ml of chloroform were added 1.3 g of 4-(2,2,2-trifluoro-1-methyl-ethyl)pyridine, and 2.91 g of meta-chloroperbenzoic acid, and the mixture was stirred at 0° C. for 2 hours, and at room temperature for 5 hours. Thereafter, the reaction solution was poured into an aqueous saturated sodium sulfite solution, followed by extraction with chloroform three times. The organic layers were combined, washed with an aqueous saturated sodium chloride solution, dried with anhydrous magnesium sulfate, and concentrated. The residue was subjected to silica gel column chromatography to obtain 0.9 g of 4-(2,2,2-trifluoro-1-methyl-ethyl)pyridine=N-oxide.

4-(2,2,2-Trifluoro-1-methyl-ethyl)pyridine=N-oxide

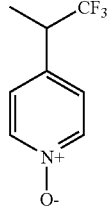

$^1$H-NMR: 1.52 (d, 3H), 3.41-3.49 (m, 1H), 7.23-7.26 (m, 2H), 8.20-8.21 (m, 2H)

Reference Production Example 67

To 8 ml of acetonitrile were added 0.9 g of 4-(2,2,2-trifluoro-1-methyl-ethyl)pyridine=N-oxide, 1.31 ml of triethylamine and 1.4 g of trimethylsilyl cyanide, and the mixture was stirred at 90° C. for 16 hours. Thereafter, the reaction solution was allowed to cool to temperature, and concentrated. The residue was subjected to silica gel column chromatography to obtain 0.7 g of 4-(2,2,2-trifluoro-1-methyl-ethyl)pyridine-2-carbonitrile.

4-(2,2,2-Trifluoro-1-methyl-ethyl)pyridine-2-carbonitrile

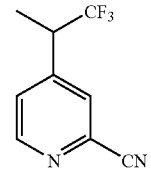

$^1$H-NMR: 1.56 (d, 3H), 3.48-3.56 (m, 1H), 7.49 (d, 1H), 7.66 (s, 1H), 8.73 (d, 1H)

Reference Production Example 68

To 7 ml of ethanol were added 0.44 g of sodium bicarbonate and 0.37 g of hydroxylamine hydrochloride, and the mixture was heated to reflux for 1 hour. After allowing to cool, 0.7 g of 4-(2,2,2-trifluoro-1-methyl-ethyl)pyridine-2-carbonitrile was added at 0° C., and the mixture was stirred for 4 hours, and concentrated. To the residue was added water, the resultant solution was extracted with ethyl acetate three times, and the organic layers were combined, washed with an aqueous saturated sodium chloride solution, dried with anhydrous magnesium sulfate, and concentrated. The residue was subjected to silica gel column chromatography to obtain 0.78 g of 4-(2,2,2-trifluoro-1-methyl-ethyl)pyridine-2-carboxamide=oxime.

4-(2,2,2-Trifluoro-1-methyl-ethyl)pyridine-2-carboxamide=oxime

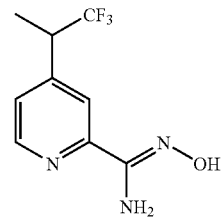

$^1$H-NMR (DMSO-d$_6$): 1.45 (d, 3H), 3.94-4.06 (m, 1H), 5.87 (s, 2H), 7.46 (dd, 1H), 7.89 (s, 1H), 8.58 (dd, 1H), 9.97 (s, 1H)

Then, Preparation Examples will be shown. Part represents part by weight.

Preparation Example 1

Ten parts of any one of the present compounds (1) to (67) is dissolved in a mixture of 35 parts of xylene and 35 parts of N,N-dimethylformamide, 14 parts of polyoxyethylene styryl phenyl ether and 6 parts of calcium dodecylbenzenesulfonate are added, and the mixture is stirred and mixed well to obtain each 10% emulsifiable concentrate.

Preparation Example 2

Twenty parts of any one of the present compounds (1) to (67) is added to a mixture of 4 parts of sodium laurylsulfate, 2 parts of calcium ligninsulfonate, 20 parts of a synthetic hydrous silicon oxide fine power and 54 parts of diatomaceous earth, and the mixture is stirred and mixed well to obtain each 20% wettable powder.

Preparation Example 3

To 2 parts of any one of the present compounds (1) to (67) are added 1 part of a synthetic hydrous silicon oxide fine powder, 2 parts of calcium ligninsulfonate, 30 parts of bentonite and 65 parts of kaolin clay, and the mixture is sufficiently stirred and mixed. Then, an appropriate amount of water is added to the mixture of them, the mixture is further stirred, and particles are made with a granulator, and dried by ventilation to obtain each 2% granule.

Preparation Example 4

One part of any one of the present compounds (1) to (67) is dissolved in an appropriate amount of acetone, to this are added 5 parts of a synthetic hydrous silicon oxide fine powder, 0.3 part of PAP and 93.7 parts of fubasami clay, the mixture is sufficiently stirred and mixed, and acetone is removed by evaporation to obtain each 1% dust.

Preparation Example 5

Ten parts of any one of the present compounds (1) to (67); 35 parts of white carbon containing 50 parts of a polyoxyethylene alkyl ether sulfate ammonium salt; and 55 parts of water are mixed, and finely-divided by a wet grinding method to obtain each 10% flowable.

Preparation Example 6

Into 5 parts of xylene and 5 parts of trichloroethane is dissolved 0.1 part of any one of the present compounds (1) to (67), and this is mixed with 89.9 parts of deodorized kerosene to obtain each 0.1% oil solution.

Preparation Example 7

Into 0.5 ml of acetone is dissolved 10 mg of any one of the present compounds (1) to (67), and this solution is mixed uniformly with 5 g of a solid feed powder for an animal (solid feed powder for breeding CE-2, commercial article of Clea Japan, Inc.). Then, acetone is evaporated and dried to obtain each bait poison.

Then, the harmful arthropod controlling effect of the present compound will be demonstrated by Test Examples.

Test Example 1

Each of preparations of the present compounds (1), (2), (4), (7), (8), (10) to (13), (19), (21) to (27), (29), (30), (32), (38) to (40), (46), (50), (51), (53), (54), (59) to (63), (65) and (66) obtained by Preparation Example 5 was diluted with water so that an active ingredient concentration became 500 ppm, to prepare a spray solution for a test.

Then, a cucumber was planted in a polyethylene cup, and grown until a first true leaf developed, and about 30 cotton aphids (*Aphis gossypii*) were parasitized therein. One day after, the spray solution for a test was sprayed to the cucumber at a ratio of 20 ml/cup. Six days after spraying, the number of cotton aphids was investigated, and a controlling value was obtained according to the following equation.

Controlling value (%)={1−(*Cb*×*Tai*)/(*Cai*×*Tb*)}×100

Letters in the equation represent the following meanings.
Cb: number of worms before treatment of non-treated section
Cai: number of worms at observation of non-treated section
Tb: number of worms before treatment of treated section
Tai: number of worms at observation of treated section As a result, the controlling value of 90% or higher was shown in any treated section of the spray solution for a test in the present compounds.

When the controlling value was obtained regarding preparations of the present compounds (1), (2), (4), (7) to (13), (15), (19), (21) to (27), (29), (30), (32), (35), (38) to (40), (45), (46), (48), (50), (51), (53), (54), (59) to (63), (65) and (66) obtained by Preparation Example 5, the controlling value of 60% or higher was shown in any section treated with the respective spray solutions.

Test Example 2

Each of the present compounds (1), (2), (4), (6) to (17), (19) to (28), (31) to (33), (36) to (40), (42) to (46), (49), (53), (56), (59), (60), (63) to (65) and (66) was formulated into a preparation according to Preparation Example 1. This preparation was diluted with water so that a concentration of the present compound became 500 ppm.

Then, about 60 female imagoes of *tetranychus urticae* koch were released on bush bean seedling (7 days after seeding, primary leaf development phase) planted in a plastic cup, and allowed to stand for a day. This seedling was spraying-treated with 30 ml of each of the diluted solutions.

Eight days and thirteen days after spraying, the number of alive mites on the leaf of bush bean was investigated, and the controlling rate was calculated according to the following equation.

Controlling rate (%)=100×{1−(number of alive mites of treated section)/(number of alive mites of non-treated section)}

As a result, the controlling rate of 90% or higher was shown after eight days and thirteen days from treatment in any section treated with the present compounds.

On the other hand, when the compound described in Japanese Patent Application National Publication (Laying-Open) No. 2001-520666 represented by the following formula (A) and the compound described in Japanese Patent Laying-Open No. 2002-205991 represented by the formula (B):

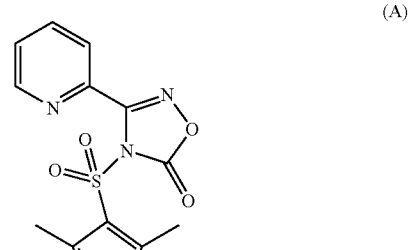

(A)

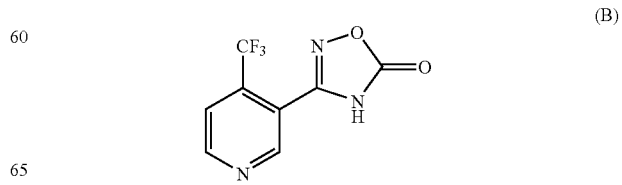

(B)

(hereinafter, referred to as comparative compound (A), and comparative compound (B)) were subjected to a test under the same conditions as those of Test Example 2, any section treated with the respective spray solutions had the controlling value of less than 30%.

INDUSTRIAL APPLICABILITY

Since the present compound has the excellent effect in controlling a pest, it is useful as an active ingredient of a pesticidal composition.

The invention claimed is:

1. A pyridine compound represented by the general formula (1):

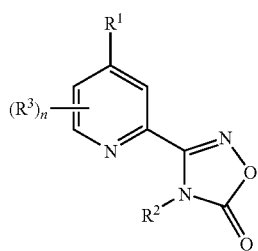

wherein $R^1$ represents a C1-C7 haloalkyl group, or a C1-C7 haloalkoxy group, the C1-C7 haloalkyl group and the C1-C7 haloalkoxy group being optionally substituted with a group selected from the group consisting of C1-C3 alkoxy groups, C1-C3 haloalkoxy groups, C3-C7 alkenyloxy groups, C3-C7 haloalkenyloxy groups, C3-C7 alkynyloxy groups, C3-C7 haloalkynyloxy groups, tri(C1-C4 alkyl)silyloxy groups and a hydroxyl group;

$R^2$ represents a cyanomethyl group; a hydrogen atom; a C1-C7 chain hydrocarbon group optionally substituted with a halogen atom; a (C3-C7 cycloalkyl)methyl group optionally substituted with a group selected from the group consisting of halogen atoms, C1-C3 alkyl groups and C1-C3 haloalkyl groups; a benzyl group optionally substituted with a group selected from the group consisting of halogen atoms, a cyano group, a nitro group, C1-C3 alkyl groups, C1-C3 haloalkyl groups and C1-C3 alkoxy groups; or a group represented by any one of the formulae $Q^1$ to $Q^5$:

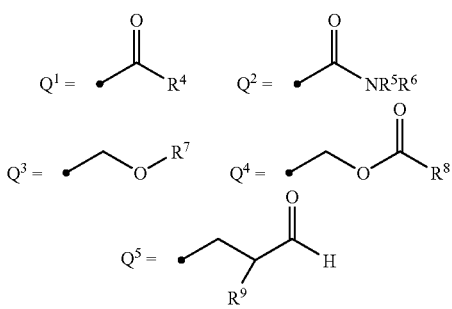

wherein $R^4$ represents a hydrogen atom; a C1-C7 chain hydrocarbon group optionally substituted with a halogen atom; or a C3-C7 cycloalkyl group optionally substituted with a group selected from the group consisting of halogen atoms, C1-C3 alkyl groups and C1-C3 haloalkyl groups;

$R^5$ and $R^6$ may be the same or different, and each represents a C1-C7 chain hydrocarbon group optionally substituted with a halogen atom; a C1-C7 alkoxy group; or a C3-C7 cycloalkyl group optionally substituted with a group selected from the group consisting of halogen atoms, C1-C3 alkyl groups and C1-C3 haloalkyl groups, or $R^5$ and $R^6$ may be taken together with a nitrogen atom constituting —$NR^5R^6$ to represent a pyrrolidin-1-yl group, a piperidino group, a hexamethyleneimin-1-yl group, a morpholino group or a thiomorpholin-4-yl group, where the pyrrolidin-1-yl group, the piperidino group, the hexamethyleneimin-1-yl group, the morpholino group and the thiomorpholin-4-yl group may be each substituted with a group selected from the group consisting of halogen atoms, C1-C3 alkyl groups and C1-C3 haloalkyl groups;

$R^7$ represents a C1-C7 chain hydrocarbon group optionally substituted with a halogen atom; a phenyl group optionally substituted with a group selected from the group consisting of halogen atoms, a cyano group, a nitro group, C1-C3 alkyl groups, C1-C3 haloalkyl groups and C1-C3 alkoxy groups; a benzyl group optionally substituted with a group selected from the group consisting of halogen atoms, a cyano group, a nitro group, C1-C3 alkyl groups, C1-C3 haloalkyl groups and C1-C3 alkoxy groups; or a C3-C7 cycloalkyl group optionally substituted with a group selected from the group consisting of halogen atoms, C1-C3 alkyl groups and C1-C3 haloalkyl groups;

$R^8$ represents a C1-C7 chain hydrocarbon group optionally substituted with a halogen atom; a phenyl group optionally substituted with a group selected from the group consisting of halogen atoms, a cyano group, a nitro group, C1-C3 alkyl groups, C1-C3 haloalkyl groups, C1-C3 alkoxy groups and C1-C3 haloalkoxy groups; or a C3-C7 cycloalkyl group optionally substituted with a group selected from the group consisting of halogen atoms, C1-C3 alkyl groups and C1-C3 haloalkyl groups; and $R^9$ represents a hydrogen atom, or a C1-C7 chain hydrocarbon group optionally substituted with a halogen atom;

$R^3$ represents a C1-C7 chain hydrocarbon group optionally substituted with a halogen atom; a C1-C7 alkoxy group; a C1-C3 haloalkoxy group; a halogen atom; a C3-C7 cycloalkyl group optionally substituted with a group selected from the group consisting of halogen atoms, C1-C3 alkyl groups and C1-C3 haloalkyl groups; or a C3-C7 cycloalkoxy group optionally substituted with a group selected from the group consisting of halogen atoms, C1-C3 alkyl groups and C1-C3 haloalkyl groups; and n represents an integer of 0 to 3.

2. The pyridine compound according to claim 1, wherein $R^1$ is a C1-C3 haloalkyl group optionally substituted with a group selected from the group consisting of C1-C3 alkoxy groups, C3-C7 alkenyloxy groups, tri(C1-C4 alkyl)silyloxy groups and a hydroxyl group, or a C1-C3 haloalkoxy group optionally substituted with a group selected from the group consisting of C1-C3 alkoxy groups, C3-C7 alkenyloxy groups, tri(C1-C4 alkyl)silyloxy groups and a hydroxyl group.

3. The pyridine compound according to claim 1, wherein $R^1$ is a C1-C3 haloalkyl group optionally substituted with a C1-C3 alkoxy group, or a C1-C3 haloalkoxy group.

4. The pyridine compound according to claim 1, wherein $R^1$ is a C1-C3 fluoroalkyl group optionally substituted with a C1-C3 alkoxy group, or a C1-C3 fluoroalkoxy group.

5. The pyridine compound according to claim 1, wherein $R^1$ is a C1-C3 fluoroalkyl group or a C1-C3 fluoroalkoxy group, $R^7$ is a C1-C7 chain hydrocarbon group optionally substituted with a halogen atom; a benzyl group optionally substituted with a group selected from the group consisting of halogen atoms, a cyano group, a nitro group, C1-C3 alkyl groups, C1-C3 haloalkyl groups and C1-C3 alkoxy groups; or a C3-C7 cycloalkyl group optionally substituted with a group selected from the group consisting of halogen atoms, C1-C3 alkyl groups and C1-C3 haloalkyl groups.

6. The pyridine compound according to claim 1, 2, 3, 4 or 5, wherein $R^2$ is a cyclopropylmethyl group optionally substituted with a C1-C3 alkyl group; a cyanomethyl group; a C1-C7 alkyl group; a hydrogen atom; a benzyl group optionally substituted with a group selected from the group consisting of halogen atoms, a cyano group, a nitro group, C1-C3 alkyl groups, C1-C3 haloalkyl groups and C1-C3 alkoxy groups; or a group represented by any one of the formulae $Q^{1a}$ to $Q^{5a}$:

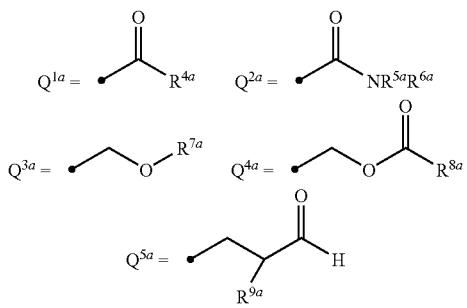

wherein $R^{4a}$ represents a C1-C7 alkyl group, a C1-C7 haloalkyl group, or a C3-C7 cycloalkyl group optionally substituted with a group selected from the group consisting of halogen atoms, C1-C3 alkyl groups and C1-C3 haloalkyl groups;

$R^{5a}$ and $R^{6a}$ may be the same or different, and each represents a C1-C7 alkyl group, a C1-C7 haloalkyl group, a C3-C7 alkenyl group or a C1-C7 alkoxy group, or $R^{5a}$ and $R^{6a}$ may be taken together with a nitrogen atom constituting —$NR^{5a}R^{6a}$ to represent a pyrrolidin-1-yl group, a piperidino group, a hexamethyleneimin-1-yl group, a morpholino group or a thiomorpholin-4-yl group, where the pyrrolidin-1-yl group, the piperidino group, the hexamethyleneimin-1-yl group, the morpholino group and the thiomorpholin-4-yl group may be each substituted with a group selected from the group consisting of halogen atoms, C1-C3 alkyl groups and C1-C3 haloalkyl groups;

$R^{7a}$ represents a phenyl group optionally substituted with a group selected from the group consisting of halogen atoms, a cyano group, a nitro group, C1-C3 alkyl groups, C1-C3 haloalkyl groups and C1-C3 alkoxy groups; a benzyl group optionally substituted with a group selected from the group consisting of halogen atoms, a cyano group, a nitro group, C1-C3 alkyl groups, C1-C3 haloalkyl groups and C1-C3 alkoxy groups; or a C3-C7 cycloalkyl group optionally substituted with a group selected from the group consisting of halogen atoms, C1-C3 alkyl groups and C1-C3 haloalkyl groups;

$R^{8a}$ represents a phenyl group optionally substituted with a group selected from the group consisting of halogen atoms, a cyano group, a nitro group, C1-C3 alkyl groups, C1-C3 haloalkyl groups, C1-C3 alkoxy groups and C1-C3 haloalkoxy groups; or a C3-C7 cycloalkyl group optionally substituted with a group selected from the group consisting of halogen atoms, C1-C3 alkyl groups and C1-C3 haloalkyl groups; and $R^{9a}$ represents a hydrogen atom or a C1-C3 alkyl group; and $R^3$ is a C3-C7 cycloalkyl group optionally substituted with a group selected from the group consisting of halogen atoms, C1-C3 alkyl groups and C1-C3 haloalkyl groups; a C3-C7 cycloalkoxy group optionally substituted with a group selected from the group consisting of halogen atoms, C1-C3 alkyl groups and C1-C3 haloalkyl groups; a halogen atom; a C1-C7 alkyl group; a C1-C7 haloalkyl group; a C1-C7 alkoxy group; or a C1-C3 haloalkoxy group.

7. The pyridine compound according to claim 1, 2, 3, 4 or 5, wherein $R^2$ is a hydrogen atom.

8. The pyridine compound according to claim 1, 2, 3, 4 or 5, wherein $R^2$ is a group represented by $Q^1$.

9. The pyridine compound according to claim 1, 2, 3, 4 or 5, wherein $R^2$ is a group represented by $Q^2$.

10. The pyridine compound according to claim 1, 2, 3, 4 or 5, wherein $R^2$ is a group represented by $Q^3$.

11. The pyridine compound according to claim 1, 2, 3, 4 or 5, wherein $R^2$ is a group represented by $Q^4$.

12. A pesticidal composition containing the pyridine compound according to claim 1 as an active ingredient.

13. A method of controlling a pest comprising applying an effective amount of the pyridine compound according to claim 1 to the pest or a place where the pest inhabits.

* * * * *